United States Patent
Davis et al.

(10) Patent No.: US 9,089,151 B2
(45) Date of Patent: Jul. 28, 2015

(54) ENZYME PRODUCING BACILLUS STRAINS

(75) Inventors: Mari Ellen Davis, Waukesha, WI (US); Justin Sawall, Waukesha, WI (US); Anthony Neumann, Wauwatosa, WI (US); Greg Siragusa, Waukesha, WI (US); Luis Fernando Romero Millan, Swindon (GB)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 0 days.

(21) Appl. No.: 13/594,594

(22) Filed: Aug. 24, 2012

(65) Prior Publication Data

US 2013/0064927 A1    Mar. 14, 2013

Related U.S. Application Data

(60) Provisional application No. 61/526,881, filed on Aug. 24, 2011, provisional application No. 61/527,371, filed on Aug. 25, 2011.

(51) Int. Cl.
| | |
|---|---|
| A23K 1/00 | (2006.01) |
| A23K 1/18 | (2006.01) |
| C12N 1/20 | (2006.01) |
| C12R 1/07 | (2006.01) |
| C12R 1/125 | (2006.01) |

(52) U.S. Cl.
CPC .............. *A23K 1/184* (2013.01); *A23K 1/009* (2013.01); *A23K 1/1826* (2013.01); *C12N 1/20* (2013.01); *C12R 1/07* (2013.01); *C12R 1/125* (2013.01)

(58) Field of Classification Search
CPC ........... A21D 8/042; A21D 2/16; A21D 2/26; C11D 3/386; C11D 3/38645; C11D 3/3869; C11B 3/003; C12N 9/2437; C12N 9/1029; C12N 9/20; C12N 9/18; C12N 11/00; C12N 11/08; C12N 11/16; C12N 1/20; C12N 9/16; C12N 9/248
See application file for complete search history.

(56) References Cited

U.S. PATENT DOCUMENTS

| | | |
|---|---|---|
| 2,906,622 A | 9/1959 | Lewis |
| 2,942,977 A | 6/1960 | Lewis |
| 3,892,846 A | 7/1975 | Wortham |
| 3,932,670 A | 1/1976 | Sakurai |
| 3,984,575 A | 10/1976 | Farr |
| 4,394,399 A | 7/1983 | Keyser et al. |
| 4,449,968 A | 5/1984 | Peterson |
| 4,579,734 A | 4/1986 | Hata et al. |
| 4,591,499 A | 5/1986 | Linn et al. |
| 4,820,531 A | 4/1989 | Tomes |
| 4,850,997 A | 7/1989 | DuBose |
| 4,919,936 A | 4/1990 | Iwanami |
| 4,981,705 A | 1/1991 | Tomes |
| 5,026,647 A | 6/1991 | Tomes et al. |
| 5,068,104 A | 11/1991 | Bhogal et al. |
| 5,073,367 A | 12/1991 | Nguyen |
| 5,139,777 A | 8/1992 | Ott et al. |
| 5,140,949 A | 8/1992 | Chu et al. |
| 5,186,962 A | 2/1993 | Hutkins et al. |
| 5,262,187 A | 11/1993 | Hahn et al. |
| 5,296,221 A | 3/1994 | Mitsuoka et al. |
| 5,311,841 A | 5/1994 | Thaxton |
| 5,314,700 A | 5/1994 | Barnes et al. |
| 5,401,501 A | 3/1995 | Pratt |
| 5,478,557 A | 12/1995 | Nisbet |
| 5,478,559 A | 12/1995 | Yabiki et al. |
| 5,482,723 A | 1/1996 | Susaki |
| 5,501,857 A | 3/1996 | Zimmer |
| 5,507,250 A | 4/1996 | Reddy |
| 5,529,793 A | 6/1996 | Garner et al. |
| 5,534,271 A | 7/1996 | Ware et al. |
| 5,540,924 A | 7/1996 | Onishi |
| 5,547,692 A | 8/1996 | Iritani et al. |
| 5,674,495 A | 10/1997 | Bowersock et al. |
| 5,703,040 A | 12/1997 | Landolo |
| 5,705,152 A | 1/1998 | Plummer |
| 5,718,894 A | 2/1998 | Mann |
| 5,725,853 A | 3/1998 | Dennis et al. |
| 5,785,990 A | 7/1998 | Langrehr |
| 5,795,602 A | 8/1998 | Craig et al. |
| 5,830,993 A | 11/1998 | Biecha |
| 5,840,318 A | 11/1998 | Marshall |
| 5,849,289 A | 12/1998 | Dobrogosz et al. |
| 5,876,990 A | 3/1999 | Reddy et al. |

(Continued)

FOREIGN PATENT DOCUMENTS

| | | |
|---|---|---|
| CA | 2169987 | 2/1996 |
| CN | 1766088 | 5/2006 |

(Continued)

OTHER PUBLICATIONS

Bernet, N. and F. Beline. 2009. Challenges and innovations on biological treatment of livestock effluents. Bioresource Technology 100:5431-5436.

Brumm, M. 2009. Brumm Speaks Out blog located at www.mnpork.com/forum/index.php accessed on Oct. 20, 2009.

Davis, M.E., et al., "Effect of a *Bacillus*-based direct-fed microbial feed supplement on growth performance and pen cleaning characteristics of growing-finishing pigs" J. Anim Sci 2008, 86: 1459-1467.

Gonzalez-Fernandez, C. and P. A. Garcia-Encina. 2009. Impact of substrate to inoculum ratio in anaerobic digestion of swine slurry. Biomass and Bioenergy 33:1065-1069.

(Continued)

*Primary Examiner* — Debbie K Ware
(74) *Attorney, Agent, or Firm* — Whyte Hirschboeck Dudek S.C.

(57) ABSTRACT

The disclosure relates to enzyme producing *Bacillus* strains that provide benefits to animals and methods of using these strains. In one embodiment, the disclosure relates compositions comprising the enzyme producing *Bacillus* strains. In yet another embodiment, the disclosure relates to a feed for an animal comprising enzyme producing *Bacillus* strains.

17 Claims, 17 Drawing Sheets

(56) References Cited

U.S. PATENT DOCUMENTS

| | | | |
|---|---|---|---|
| 5,879,719 | A | 3/1999 | Valentine |
| 5,910,306 | A | 6/1999 | Alving et al. |
| 5,945,333 | A | 8/1999 | Rehberger |
| 5,948,431 | A | 9/1999 | Lavery |
| 5,964,187 | A | 10/1999 | Willis |
| 5,965,128 | A | 10/1999 | Doyle |
| 5,976,580 | A | 11/1999 | Ivey et al. |
| 5,980,898 | A | 11/1999 | Glenn et al. |
| 6,008,195 | A | 12/1999 | Selsted |
| 6,060,050 | A | 5/2000 | Brown et al. |
| 6,090,416 | A | 7/2000 | Iritani et al. |
| 6,120,810 | A | 9/2000 | Rehberger et al. |
| 6,132,710 | A | 10/2000 | Panigrahi et al. |
| 6,156,355 | A | 12/2000 | Shields, Jr. |
| 6,177,012 | B1 | 1/2001 | Lawler et al. |
| 6,207,210 | B1 | 3/2001 | Bender et al. |
| 6,207,411 | B1 | 3/2001 | Ross |
| 6,221,650 | B1 | 4/2001 | Rehberger |
| 6,306,385 | B1 | 10/2001 | Lee |
| 6,346,422 | B1 | 2/2002 | Butty et al. |
| 6,410,016 | B2 | 6/2002 | Maruta |
| 6,455,063 | B1 | 9/2002 | Rehberger et al. |
| 6,537,544 | B1 | 3/2003 | Johansson et al. |
| 6,608,222 | B2 | 8/2003 | Bonsignore et al. |
| 6,733,759 | B2 | 5/2004 | Ivey et al. |
| 6,797,276 | B1 | 9/2004 | Glenn et al. |
| 6,887,489 | B2 | 5/2005 | Rehberger et al. |
| 6,896,883 | B2 | 5/2005 | Bergstrom et al. |
| 6,908,620 | B2 | 6/2005 | McDougald et al. |
| 6,910,446 | B2 | 6/2005 | Johnston, Jr. |
| 6,951,643 | B2 | 10/2005 | Rehberger et al. |
| 7,141,255 | B2 | 11/2006 | Glassberg et al. |
| 7,247,299 | B2 | 7/2007 | Lin et al. |
| 7,354,757 | B2 | 4/2008 | Rehberger et al. |
| 7,384,628 | B2 | 6/2008 | Rehberger et al. |
| 7,470,531 | B2 | 12/2008 | Rehberger et al. |
| 7,618,640 | B2 | 11/2009 | Rehberger et al. |
| 7,754,469 | B2 | 7/2010 | Baltzley et al. |
| 8,021,654 | B2 | 9/2011 | Rehberger et al. |
| 8,021,655 | B2 | 9/2011 | Rehberger et al. |
| 8,025,874 | B2 | 9/2011 | Bellot et al. |
| 8,221,742 | B2 | 7/2012 | Rehberger et al. |
| 8,404,227 | B2 | 3/2013 | Bellot et al. |
| 8,420,074 | B2 | 4/2013 | Rehberger et al. |
| 8,444,966 | B2 | 5/2013 | Rehberger et al. |
| 2001/0031276 | A1 | 10/2001 | Shelford et al. |
| 2002/0018770 | A1 | 2/2002 | Maruta |
| 2002/0104485 | A1 | 8/2002 | Lewis et al. |
| 2003/0021874 | A1 | 1/2003 | Nunes et al. |
| 2003/0099624 | A1 | 5/2003 | Porubcan |
| 2004/0047872 | A1 | 3/2004 | Glenn et al. |
| 2004/0170617 | A1 | 9/2004 | Finegold |
| 2005/0226897 | A1 | 10/2005 | Lee |
| 2005/0255092 | A1 | 11/2005 | Rehberger |
| 2006/0067924 | A1 | 3/2006 | Lee et al. |
| 2007/0048432 | A1 | 3/2007 | Holzgraefe et al. |
| 2007/0071738 | A1 | 3/2007 | Rehberger et al. |
| 2007/0202088 | A1 | 8/2007 | Baltzley et al. |
| 2008/0014290 | A1 | 1/2008 | Jones et al. |
| 2008/0118472 | A1 | 5/2008 | Rode et al. |
| 2008/0190373 | A1 | 8/2008 | Lee |
| 2008/0195064 | A1 | 8/2008 | Correa et al. |
| 2008/0233104 | A1 | 9/2008 | Farmer |
| 2009/0074725 | A1 | 3/2009 | Watson |
| 2009/0136622 | A1 | 5/2009 | Rehberger et al. |
| 2009/0275109 | A1 | 11/2009 | Bellot et al. |
| 2009/0280090 | A1 | 11/2009 | Rehberger |
| 2010/0172873 | A1 | 7/2010 | Mertz et al. |
| 2010/0183574 | A1 | 7/2010 | Davis et al. |
| 2013/0045185 | A1 | 2/2013 | Davis et al. |
| 2013/0064927 | A1 | 3/2013 | Davis et al. |

FOREIGN PATENT DOCUMENTS

| | | |
|---|---|---|
| CN | 101244088 | 8/2008 |
| DE | 2253426 | 10/1971 |
| EP | 0203586 A3 | 12/1986 |
| EP | 0287699 | 7/1993 |
| EP | 2336294 | 6/2011 |
| WO | 9824327 | 6/1998 |
| WO | 9953775 | 10/1999 |
| WO | 2004104175 | 12/2004 |
| WO | WO 2004104175 | 12/2004 |
| WO | 2005027829 | 3/2005 |
| WO | 2005112658 | 12/2005 |
| WO | 2009015478 | 2/2009 |
| WO | 2009142755 | 11/2009 |
| WO | 2010139726 | 12/2010 |
| WO | 2011011872 | 2/2011 |
| WO | 2012149159 | 11/2012 |

OTHER PUBLICATIONS

Hoff, S. J., D. S. Bundy, M. A. Nelson, B. C. Zelle, L. D. Jacobson, A. J. Heber, N. I. Jinqin; Y. Zhang, J. A. Koziel, and D. B. Beasley. 2006. Emissions of ammonia, hydrogen sulfide, and odor before, during, and after slurry removal from a deep-pit swine finisher. Journal of the Air & Waste Management Association 56:581-590.

Moody, L. et al., "Deep Pit Swine Facility Flash Fires and Explosions: Sources, Occurrences, Factors, and Management", Department of Agricultural and Biosystems Engineering Iowa State University, Dec. 21, 2009.

Peu, P., H. Brugere, A. Pourcher, M. Kerouredan, J. Godon, J. Delgenes, and P. Dabert. 2006. Dynamics of a pig slurry microbial community during anaerobic storage and management. Applied and Environmental Microbiology 72:3578-3585.

Rehberger, J., E. Davis, A. Baker, T. Parrott, A. Veldkamp, and T. Rehberger. 2009. A preliminary comparison of bacterial communities of foaming and non-foaming swine manure pits. Journal of Animal Science 87(Suppl. 2):492.

Stein, H. H. and G. C. Shurson. 2009. Board Invited Review: The use and application of distillers dried grains with solubles in swine diets. Journal of Animal Science 87:1292-1303.

Shurson, J. 2009. Analysis of current feeding practices of distiller's grains with soluble in livestock and poultry feed relative to land use credits associated with determining the low carbon fuel standard for ethanol. Accessed at: www.ethanolrfa.org/objects/documents/2288/rfa.analysis_of_current_feeding_practices_of_distiller_final_3-25-09.pdf on Oct. 23, 2009.

Snell-Castro, R., J. Godon, J. Delgenes, and P. Dabert. 2005. Chracterization of the microbial diversity in a pig manure storage pit using small subunit rDNA sequence analysis. FEMS Microbiology Ecology 52:229-242.

Soddell, J. A. and R. J. Seviour. 1990. Microbiology of foaming in activated sludge plants. Journal of Applied Bacteriology 69:145-176.

Zhu, J. 2000. A review of microbiology in swine manure odor control. Agriculture, Ecosystems, and Environment 78:93-106.

Bitton, G. 1994. Bulking and foaming in activated sludge plants. In Wastewater Microbiology. John Wiley & Sons, Inc., New York: pp. 167-187.

Fu, S. X., M. Johnston, R. W. Fent, D. C. Kendall, J. L. Usry, R. D. Boyd, and G. L. Allee. 2004. Effect of corn distiller's dried grains with soluble (DDGS) on growth, carcass characteristics and fecal volume in growing-finishing pigs. Journal of Animal Science 82 (Suppl. 2):80.

Pagilla, K., K. Craney, and W. Kido. 1997. Causes and effects of foaming in anaerobic sludge digesters. Water Science Technology 36:463-470.

Pagilla, K. R., A. Sood, and H. Kim. 2002. *Gordonia* (Nocoardia) amarae foaming due to biosurfactant production. Water Science and Technology 46:519-524.

Whitehead, T. R. and M. A. Cotta. 2001. Characterization and comparison of microbial populations in swine faeces and manure storage pits by 16S rDNA gene sequence analyses. Anaerobe 7:181-187.

Wolfe, R. S. 1971. Microbial formation of methane. Adv. Microbiol. Physiol. 6: 107-145.

(56) References Cited

OTHER PUBLICATIONS http://www.alekn-murray.com/EZ4pib.htm, accessed Jan. 15, 2013.
International Search Report for PCT App. No. PCT/US2012/035211 mailed on Aug. 1, 2012.
Seo, J.K, "Direct-ref Microbials for Ruminant Animals", Asian-Aust. J. Anim. Sci. vol. 23, No. 12 : 1657-1667, Dec. 2010.
Krehbiel, C.R., "Bacterial direct-fed microbials in ruminant diets: Performance response and mode of action", J. Anim. Sci. 81(E. Suppl. 2): E120-132, Oct. 1, 2002.
Johnson, K.A., "Methane emissions from cattle", J. Anim. Sci. 1995, 73:2483-2492.
Power, E. G., "RAPD typing in microbiology—a technical review," J. Hosp. Infect. (1996) 34(4):247-265.
T. Hino (1993) J. Gen. Appl. Microbiol., 39, 35-45.
Lehloenya, K. V., Krehbiel, C. R., Mertz, K. J., Rehberger, T. G., Spicer, L. J. (2008) Effects of propionibacteria and yeast culture fed to steers on nutrient intake and site and extent of digestion. V 92 (2):653.
Stein, D. R., Allen, D. T., Perry, E. B., Bruner, J. C., Gates, K. W., Rehberger, T. G., Mertz, K. J., Jones, D., Spicer, L. J. (2006) Effects of feeding propionibacteria to dairy cows on milk yield, milk components, and reproduction. J Dairy Sci 89 (1):111.
Thorpe, A. (2009) Enteric fermentation and ruminant eructation: the role (and control?) of methane in the climate change debate. Climatic Change 93 (3):407.
Aleman, M. M. D. R. Stein, D.T. Allen, E. Perry, K. V. Lehloenya, T. G. Rehberger, K. J. Mertz, D. A. Jones, and L. J. Spicer. 2007. Effects of feeding two levels of propionibacteria to dairy cows on plasma hormones and metabolities. Journal of Dairy Research 74:146-53.
De Ondarza, M. B., and W. M. Seymour. 2008. Case study: effect of propionibacteria supplementation on yield of milk and milk components of dairy cows. The Professional Animal Scientist 24:254-259.
Francisco, C. C., C. S. Chamberlain, D. N. Waldner, R. P. Wettemann, and L. J. Spicer. 2002. Propionibacteria fed to dairy cows: effects on energy balance, plasma metabolites and hormones and reproduction. Journal of Dairy Science 85:1738-51.
Lehloenya, K. V., D. R. Stein, D. T. Allen, G. E. Selk, D. A. Jones, M. M. Aleman, T. G. Rehberger, K. J. Mertz, and L. J. Spicer. 2007. Effects of feeding yeast and propionibacteria to dairy cows on milk yield and components, and reproduction. Journal of Animal Physiology and Animal Nutrition 92:190-202.
Weiss, W. P., D. J. Wyatt and T. R. McKelvey. 2008. Effect of feeding propionibacteria on milk production by early lactation dairy cows. Journal of Dairy Science 91:646-52.
Teo et al., "Applied & Environmental Microbiology," (Aug. 2005) vol. 71, 8:4185-4190.
Timmerman, H. M. et al, "Health and growth of veal calves fed milk replacers with or without probiotics," J. Dairy Sci. (2005) 88:2154-2165.
Torrallardona, D. et al, "Effect of fishmeal replacement with spray-dried plasma and colistin on intestinal structure, intestinal microbiology, and performance of weanling pigs challenged with *Escherichia coli* K99," J. Anim. Sci. (2003) 81:1220-1226.
Van Dijk, A. et al, "Growth performance of weanling pigs fed spray-dried animal plasma: a review," Livestock Production Science (2001a) 68:263-274.
Van Dijk, A. et al, "Growth performance and health status in weanling piglets fed spray-dried porcine plasmas under typical Northern European conditions," J. Anim. Physiol. Anim. Nutr. (Berl). (2002b) 86:17-25.
Vance, H. N., "A survey of the alimentary tract of cattle for *Clostridium perfringens*," Can. J. Comp. Med. Vet. Sci. (1967) 31:260-264.
"Watt Feed E-News Feb. 8, 2005" 'Online! Feb. 8, 2005, pp. 1-6, XP002342563, retrieved from the Internet: URL:http://www.wattnet.com/Newsletters/feed/htm/FEBFEED05.htm> [source: PCT/US05/017141 ISR].
Wattiau, P et al, "A PCR test to identify *Bacillus subtilis* and closely related species and its application to the monitoring of wastewater biotreatment," Appl Microbiol Biotechnol 56:816-819, 2001.
Wattiau et al, Appl. Microbiol Biotechnol 2001, vol. 56, p. 816-819.
Wiard, T et al, "The effect of a biological litter treatment on *Salmonella* prevalence in turkey breeder flock litter," Poultry Science 80:127 (Suppl. 1):1-4, 2001.
Casey, P. G. et al, "A five-strain probiotic combination reduces pathogen shedding and alleviates disease signs in pigs challenged with *Salmonella enterica* serovar *Typhimurium*," Appl. Environ. Microbiol, (2007) 73:1858-1863.
Wiard, T et al, Application of plating enumerations and denaturing gradient gel electrophoresis to study turkey poult gastrointestinal tract bacterial diversity, (4 pgs) presented at the Poultry Science Assoc meeting, Madison, WI 2003.
Wiard, T et al, "Application of plating enumerations and denaturing gradient gel electrophoresis to study turkey poult gastrointestinal tract bacterial diversity," Poster #244 and its abstract, presented at the Poultry Science Assoc meeting, Madison, WI 2003.
Williams, J. G. et al, "DNA polymorphisms amplified by arbitrary primers are useful as genetic markers," Nucleic Acids Res. (1990) 18:6531-6535.
Willoughby, D H et al, "Periodic recurrence of gangrenous dermatitis associated with *Clostridium speticum* in a broiler chicken operation," J Vet Diagn Invest 8:259-261, 1996.
Wills, "*Escherichia coli* postweaning diarrhea," Vet Clinics N Am, pp. 138-140, 2000.
Wilson, M, "Segregated early weaning," Pig Lett. (1995) 15:17-20.
Wistuba et al, "Influence of fish oil supplementation on growth and immune system characteristics of cattle," J. Anim. Sci. (2005) 83:1097-1101.
Wu, X. Y. et al, "Characterization of *Mesophilic bacilli* in feces of feedlot cattle," J. Appl. Microbiol. (2007) 102:872-879.
Yang, H. et al, "Effect of adding a *Bacillus* based direct fed microbial on performance of nursery pigs fed diets with or without antibiotics," J. Anim. Sci. (2003).
Yang, W., "Effects of direct-fed microbial supplementation on ruminal acidosis, digestibility, and bacterial protein synthesis in continuous culture," Animal Feed Science and Technology, (2004) 114(4): 179-193.
Zhu, X Y, "16S rRNA-based analysis of microbiota from the cecum of broiler chickens," Applied and Environmental Microbiology, 68(1):124-137, Jan. 2002.
Zoetendal, E G et al, Molecular ecological analysis of the gastrointestinal microbiota: a review, J of Nutrition pp. 465-472, 2004.
International Search Report and the Written Opinion of the International Searching Authority, or the Declaration mailed Dec. 9, 2005 for PCT/US2005/017141, filed on May 13, 2005.
International Search Report and the Written Opinion of the International Searching Authority, or the Declaration mailed Dec. 6, 2009 for PCT/US2009/40920, filed on Apr. 17, 2009.
Non-Final Office Action mailed May 13, 2009 for U.S. Appl. No. 11/565,474, filed Nov. 30, 2006.
Notice of Allowance, mailed Apr. 10, 2009 for U.S. Appl. No. 11/129,767, filed May 13, 2005.
Final Office Action mailed Jan. 22, 2009 for U.S. Appl. No. 11/129,767, filed May 13, 2005.
Non-Final Office Action mailed Feb. 5, 2008 for U.S. Appl. No. 11/129,767, filed May 13, 2005.
Gyles, C., Workshop #4: Enteric Diseases of Nursery Pigs, pp. 29-41, AASV 32nd Annual Meeting (2001), Nashville, Tenn.
Sale: Agtech Products, Inc. purchased strain *Bacillus subtilis* 2084 from a third party. At least as early as Sep. 10, 2004.
Sale: Agtech Products, Inc. purchased strain *Bacillus licheniformis* 21 from a third party. At least as early as Jan. 30, 2007.
Office Action mailed Dec. 10, 2010 for U.S. Appl. No. 12/404,149, filed Mar. 13, 2009.
Office Action mailed Dec. 22, 2010 for U.S. Appl. No. 12/573,390, filed Oct. 5, 2009.
Canadian Office Action mailed Jan. 27, 2011 for Canadian App. No. 2566617.
Office Action mailed Mar. 11, 2010 for Canadian App. No. 2,566,617.
Kim et al, "Aerobic nitrification-denitrification by heterothrophic *Bacillus* strains". Bioresource Technology. 2005, 96, pp. 1897-1906.

(56) References Cited

OTHER PUBLICATIONS

Hofacre, C L et al, "Subcutaneous Clostridial infection in broilers," Case Report, Avian Diseases vol. 30(3):620-622, 1986.
Hong, H. A. et al, "The use of bacterial spore formers as probiotics," FEMs Microbiol. Rev. (2005) 29:813-835.
Hungate, R. E. et al, "Microbiological and physiological changes associated with acute indigestion in sheep," Cornell Vet. (1952) 42:423.
Janstova, B. et al, "Heat Resistance of *Bacillus* spp. Spores Isolated form Cow's Milk and Farm Environment," Acta Vet.. BRNO (2001) 70:179-184.
Jenny, B. F. et al, "Performance and fecal flora of calves fed a *Bacillus subtilis* concentrate," J. Dairy Sci. (1991) 74:1968-1973.
Jost B. H. et al, "Atypical cpb2 genes, encoding beta2-toxin in *Clostridium perfringens* isolates of nonporcine origin," Infect. Immun. (2005) 73:652-656.
/K/ "A multiple-strain product containing *Bacillus* strain BS 27 and other strains has been sold, at least as early as Jan. 1, 2000."
Karunakaran, D et al, "Use of antibiotics and its impact on gut microflora in turkeys," Am Avian Path, Philadelphia, PA, Aug. 2004.
Karunakaran, D, "Microbioligical challenges of commercial turkey flocks and methods of control," Poster #PP51 presented at AAAP Symposium on Poultry Vaccines and Vaccination Practices, Jul. 15-17, 2002.
Kennedy, C et al, "The A-toxin of *Clostridium septicum* is essential for virulence," Molecular Microbiology, 57(5): 1357-1366, 2005.
King, M. et al, "Terminal restriction fragment length polymorphism analysis of gastrointestinal bacteria from conventional and segregated early weaned pigs: colonization and succession of putative pathogens and potential direct fed microbials," J. Anim Sci. (2005) 83 (Suppl. 1): 197.
Kyriakis, S. C. et al, "The effect of probiotic LSP 122 on the control of post-weaning diarrhea syndrome of piglets," Res. Vet. Sci. (1999) 67:223-228.
La Ragione R M et al, "*Bacillus subtilis* spores competitively exclude *Escherichia coli* 078:K80 in poultry," Vet Microbiol 79:133-142, 2001.
La Ragione, R. M. et al, "Competitive exclusion by *Bacillus subtilis* spores of *Salmonella enterica* serotype Enteritidis and *Clostridium perfringens* in young chickens," Vet. Microbiol, (2003) 94:245-256.
Lu, J et al, "Diversity and succession of the intestinal bacterial community of the maturing broiler chicken," Applied and Environmental Microbiology, 69(11):6816-6824, Nov. 2003.
Marquardt, R et al, "Passive protective effect of egg-yolk antibodies against enterotoxigenic *Escherichia coli* K88+ infection in neonatal and early-weaned piglets," FEMS Immunology and Med Microbiology 23:283-288, 1999.
Marsh, T. et al, "Terminal restriction fragment length polymorphism analysis web-based research tool for microbial community analysis," Appl Environ Microbiol (2000) 66:3616-3620.
Maxwell, Jr., C. V. et al, "Feeding Weanling Pigs. In: Austin J. Lewis and Lee L. Southern (Ed.)," Swine Nutrition 2nd Edition. (2001) p. 691-717.
McCracken, B. A. et al, "Diet-dependent and diet-independent metabolic responses underlie growth stasis of pigs at weaning," J. Nutr. (1995) 125, 2838-2845.
McDonough, S. P., "Enteric pathogens in intensively reared veal calves," Am. J. Vet. Res. (1994) 55(11):1516-1520.
McMillan, K., "Foal pneumonia: An Illinois survey," An Health and Nutrit 34 (1986).
Morrill, J. L. et al, "Plasma proteins and a probiotic as ingredients in milk replacer," J. Dairy Sci. (1995) 78:902-907.
Mouricout, M. A. et al, "Inhibition of mannose-resistant haemagglutination of sheep erythrocytes by enterotoxigenic *Escherichia coli* in the presence of plasma glycoprotein glycans," FEMS Microbiol. Lett. (1986) 37:145-149.
Muir, L.A. et al, "Prevention of induced lactic acidosis in cattle by thiopeptin," J. Anim. Sci. (1981) 52:635.
Muyzer, G et al, "Profiling of complex microbial populations by denaturing gradient gel electrophoresis analysis of polymerase chain reaction-amplified genes coding for 16S rRNA," Applied and Environmental Microbiology, 59 (3):695-700, Mar. 1993.
Nagy, G et al, "Genetic diversity among *Escherichia coli* isolates carrying f18 genes from pigs with porcine postweaning diarrhea and edema disease," J Clinical Microbiology 37:5:1642-1645, May 1999.
Nagy, G et al, "Genetic diversity among *Escherichia coli* isolates carrying f18 genes from pigs with porcine postweaning diarrhea and edema disease," J Clinical Microbiology 37:5:1642-1645, May 1999.
NCBI gene bank accession #M59107.
NCBI gene bank accession #X73447.
Niilo, L., "*Clostridium perfringens* in animal disease: a review of current knowledge," Can. Vet. J. (1980) 21:141-148.
Nollet, H. et al, "Protection of just weaned pigs against infection with F18+ *Escherichia coli* by non-immune plasma powder," Vet. Microbiol. (1999) 65:37-45.
"Nonruminant Nutrition: weanling Pigs-additives" Online! 2004, pp. 25-28 XP002342561, Retrieved from the Internet: URL:http//www.fass.org/2004/abstracts/25.PDF>p. 26, col. 2, paragraph 3-5 [source: PCT US2005/017141 ISR].
Owens, F. N. et al, "Acidosis in cattle: a review," J. Anim. Sci. (1998) 76:275-286.
Parrott, D et al, "Molecular typing of hemolytic *Escherichia coli* isolated from swine," Paper 385 (1 pg), Intl Pig Vet Soc, 2002.
Patterson, J A et al, "Application of prebiotics and probiotics in poultry production," Poultry Science 82:626-631, 2003.
Perez-Bosque, A. et al, "Dietary plasma protein affects the immune response of weaned rats challenged with *S. aureus*," Superantigen B. J. Nutr. (2004) 134:2667-2672.
Pyne, E et al, Prevalence and genetic diversity of *Clostridum perfringens* isolated from commercial turkey houses, Abstract #432 in Abstracts of papers.
Rehberger, T, "Genome analysis of *Propionibacterium freudenreichii* by pulsed-field gel electrophoresis," Current Microbiology 27(1):21-25 Jul. 1993 (abstract).
Roche, K. C. et al, "Transforming growth factor beta-1 ameliorates intestinal epithelial barrier disruption by *Cryptosporidium parvum* in the absence of mucosal T lymphocytes," Infect. Immun. (2000) 68:5635-5644.
Roe, S, "Protein purification techniques," 2d Ed. Oxford U. Press, 172-175 (2001).
Sambrook, 3d Ed, 2001 (reference book, no specific pages cited or copy provided).
Slyter, L.L, "Influence of acidosis on rumen function," J. Anim. Sci. (1976) 43:910.
Snoeyenbos, G H, "Protecting chicks and poults from *Salmonellae* by oral administration of "normal" gut microflora," Avian Diseases 22(2):273-287, 1977.
Songer, J. G., "Clostridial enteric diseases of domestic animals," Clinical Microbiology Reviews (1996) 9(2):216-234.
Stable Fresh TM 1:3 concentrate, "An all natural USDA approved concentrate that eliminates stall odors for just pennies per day, per stall," Sterling Creek Enterprises (2 pgs).
"Table of Contents" Online! 2004, p. 1-4, XP002342560, retrieved from the Internet: URL:http://www.fass.org/2004/abstracts/>, p. 1, lines 1-14 [source: PCT/US05/017141 ISR].
Tam, N. K. M. et al, "The intestinal life cycle of *Bacillus subtilis* and close relatives," J. Bacteriol. (2006) 188:2692-2700.
Tang, M. et al, "Effect of segregated early weaning on postweaning small intestinal development in pigs," J. Anim. Sci. (1999) 77:3191.
Tanner, M. K. et al. "Respiratory and environmental effects of recycled phone book paper versus sawdust as bedding for horses," J Eq Vet Sci (1998) 468-476.
Tannock, G. W., "A special fondness for *Lactobacilli*," Appl. Environ, Microbiol. (2004) 70:3189-3194.
Banach, S. et al, "Influence of *Lactobacillus brevis* 1E-1 on the gastrointestinal microflora of pre-weaning and weaning pigs," J. Animal Sci., V. 80, Supp 1/J. Dairy Sci., V. 85, Supp 1, p. 248 (abstract Jul. 21, 2002).
Benoit, V. et al, "Characterization of Brevicin 27, a bacteriocin synthesized by *Lactobacillus brevis* SB27," Current Microbiol. 28:53-61 (1994).

(56) References Cited

OTHER PUBLICATIONS

Brown, D. C. et al, "Effect of milk supplementation with *Lactobacillus brevis* 1E-1 on intestinal microflora, intestinal morphology and pig performance," J. Anim. Sci. 81(supp 2): p. 76 (2003).
Coventry, M. J. et al, "Production of Brevicin 286 by *Lactobacillus brevis* VB286 and partial characterization," J. Applied Bacteriology, 80:91-98 (1996).
Davis, M. E. et al, "Influence of *Lactobacillus brevis* 1E-1 on the gastrointestinal microflora, gut morphology, and pig performance pre- and post-weaning," 9th Intl Symposium on Digestive Physiology in Pigs, Banff, AG, Canada 2:265-267 (May 14-17, 2003).
Kraus, D. O. et al, "Ribotyping of Adherent *Lactobacillus* from weaning pigs: a basis for probiotic selection based on diet and gut compartment," Anaerobe 3:317-325 (1997).
Lewus, C. B. and Montville, T. J., "Detection of bacteriocins produced by lactic acid bacteria," J. Microbiological Methods 13:145-150 (1991).
Parrott, T. D. et al, "Characterization of the predominant *Lactobacilli* isolated form the gastrointestinal tract of post-weaned pigs," presented at the Am Soc for Microbiology Annual General Meeting, (May 23-27, 1994).
Schutz, H. et al, "Anaerobic reduction of glycerol to propanediol-1.3 by *Lactobacillus brevis* and *Lactobacillus buchneri*," System Appl Microbiol., 5:169-178 (1984).
Tannock, G. W. et al, "*Lactobacillus* succession in the piglet digestive tract demonstrated by plasmid profiling," Appl and Environmental Microbial, 56(5): 1310-1316 (May 1990).
EP Supplemental Search Report for related EP 03765947 (Feb. 22, 2006).
PCT International Search Report for related PCT/US03/22948 (Jul. 22, 2003).
Office Action mailed Jul. 7, 2006 for U.S. Appl. No. 10/624,443, filed Jul. 22, 2003.
Final Office Action mailed Feb. 22, 2007 for U.S. Appl. No. 10/624,443, filed Jul. 22, 2003.
EP Office Action mailed Feb. 3, 2011 for EP Application No. 03765947.1.
CA Office Action mailed Mar. 17, 2011 for CA Application 2,493,121.
Gebert, S., "*Lactobacillus brevis* strain 1E1 administered to piglets through milk supplementation prior to weaning maintains intestinal integrity after the weaning event", Beneficial Microbes, XXX 2011, Wageningen Academic Publishers.
Barrow, P.A., "Changes in the micro flora and physiology of the anterior intestinal tract of pigs weaned at 2 days, with special reference to the pathogenesis of diarrhea", Infection and Immunity, Dec. 1977, p. 586-595.
Savage, D.C., "The ecological digestive system and its colonisation", Rev. Sci. Tech. Off. Int. Epiz., 1989, 8 (2), 259-273.
Savage, D.C, "Factors influencing biocontrol of bacterial pathogens in the intestine", Food technology, vol. 41, 1987, p. 82-87.
Allison, M.J. et al., 1975. Grain overload in cattle and sheep: Changes in microbial populations in the cecum and rumen. Amer. J. Vet Res. 36:181.
Dunlop, R.H.. 1972. Pathogenesis of ruminant lactic acidosis. Adv. Vet Sci. Comp Med. 16:259.
Elam, C.J. 1976. Acidosis in feedlot cattle: Practical observations. J. Anim. Sci. 43:898.
Hungate, R.E., et al. 1952. Microbiological and physiological changes associated with acute indigestion in sheep. Cornell Vet. 42:423.
Muir, L.A., et al. 1981. Prevention of induced lactic acidosis in cattle by thiopeptin. J. Anim. Sci. 52:635.
Owens, F.N., et al. 1998. Acidosis in cattle: a review. J. Anim. Sci. 76:275-286.
Slyter, L.L. 1976. Influence of acidosis on rumen function. J. Anim. Sci. 43:910.

Yang, W., 2004. Effects of direct-fed microbial supplementation on ruminal acidosis, digestibility, and bacterial protein synthesis in continuous culture. Animal Feed Science and Technology, 114(4): 179-193.
Rolfe, K., et al. "Impact of a New Direct-Fed Microbial on Intake and Ruminal pH." Nebraska Beef Cattle Reports, Animal Science Department, University of Nebraska—Lincoln, 2009.
Galbraith, E.A., et al. "T382 Effect of direct-fed microbial (DFM) products on rumen bacterial communities in Holstein cows at 2 and 6 weeks postcalving." J. Anim. Sci. vol. 88, E-Suppl. 2 / J. Dairy Sci. vol. 93, E-Suppl. 1 / Poult. Sci. vol. 89, E-Suppl. 1 (2010) pp. 431.
Ferguson, J.D., et al. "1134 the influence of *Bacillus pumilus* 8G-134 on milk production of dairy cows in early lactation." J. Anim. Sci. vol. 88, E-Suppl. 2 / J. Dairy Sci. vol. 93, E-Suppl. 1 / Poult. Sci. vol. 89, E-Suppl. 1 (2010) pp. 871.
Smith, X., et al. "Selection of rumen bacteria to modulate rumen function in cattle fed readily-fermentable carbohydrates." Rowett-INRA 2010: Gut Microbiology, in Aberdeen, Scotland, Jun. 23-25, 2010.
Dong, S.H., et al. "T344 the survival of *Bacillus subtilis* natto in rumen and douodenum of Holstein dairy cows" J. Anim. Sci. vol. 89, E-Suppl. 1 / J. Dairy Sci. vol. 94, E-Suppl. 1 pp. 382-383.
Kang, H.Y., et al. "T348 Effect of feeding *Bacillus subtilis* natto fermentation production on hindgut fermentation and microbiota of Holstein dairy cows." J. Anim. Sci. vol. 89, E-Suppl. 1 / J. Dairy Sci. vol. 94, E-Suppl. 1 pp. 384.
Peng, H., et al. "T350 Effect of feeding *Bacillus subtilis* natto fermentation production on milk production and composition, blood metabolites and rumen fermentation in early lactation dairy cows." J. Anim. Sci. vol. 89, E-Suppl. 1 / J. Dairy Sci. vol. 94, E-Suppl. 1 pp. 384-385.
Henning, P.H., et al. "Effect of ruminal administration of the lactate-utilizing strain *Megasphaera elsdenii* (Me) NCIMB 41125 on abrupt or gradual transition from forage to concentrate diets." Animal Feed Science and Technology 157 (2010) 20-29.
Henning, P.H., et al. "The potential of *Megasphaera elsdenii* islolates to control ruminal acidosis." Animal Feed Science and Technology 157 (2010) 13-19.
AU office action mailed on Jul. 19, 2011 for Pat. App. No. 2009322439.
International Search Report and written Opinion mailed on Mar. 4, 2010 for PCT App. No. PCT/US09166392.
From U.S. Dept. of Agriculture, http://nrrl.ncaur.usda.gov/cgi-bin/usda/.
ATCC Advanced Ctalog Search on Jun. 18, 2012.
International Preliminary Report on Patentability issued Jun. 7, 2011 for PCT App. No. PCT/US2009/066392.
Kim, S.W. et al. "Potential Use of *Propionibacterium acidipropionici*, strain DH42 as a direct-fed microbial for cattle", Michigan State University—Beef Cattle, Sheep and Forage Systems Research and Demonstration Report, 2001.
Office Action mailed Nov. 17, 2009 for Canadian App. No. 2,455,399.
Beam, S.W. and W. R. Butler. 1998. Energy Balance, metabolic hormones, and early postpartum follicular development in dairy cows fed prilled lipid. J. Dairy Sci. 81:121-131.
Canfield, R.W. and W.R. Butler. 1991. Energy balance, first ovulation and the effects of naloxone on LH secretion in early postpartum dairy cattle. J. Anim. Sci. 69: 740-746.
Carrol, D.J., M.J. 'erred, R.R. Grummer, D.K..Combs, R.A. Pierson, and E.R. Hauser. 1990. Effect of fat supplementation and immature alfalfa to concentrate ratio on plasma progesterone, energy balance, and reproductive traits of cattle. J. Dairy Sci 73:2855-2863.
Amaral-Phillips, D.M., A.D. McGilliaid, G.L. Lindberg, J.J. Veenhuizen, J.J.,. and J. W. Young. 1993. Effects of decreased availability of glucose for dairy cows. J. Dairy Sci. 76:752-761.
Grummer, R.R. and D.J. Carroll. 1991. Effects of dietary fat on metabolic disorders and reproductive performance of dairy cattle. J. Anim. Sci. 69: 3838-3852.
Grurnmer, R.R. and D.J. Carroll. 1988. A review of lipoprotein cholesterol metabolism: importance to ovarian function. J. Anim. Sci. 66:3160-3173.

(56) References Cited

OTHER PUBLICATIONS

Hawkins, G.E., K.A. Cummins, M. Silverio and J.J. Jilek. 1985. Physiological effects of whole cottonseed in the diet of lactating dairy cows. J. Dairy Sci. 68:2608-2614.

Huhtanen, P., H. Miettinen, and M. Ylinen. 1993. Effect of increasing ruminal butyrate on milk yield and blood constituents in dairy cows fed a grass silage-based diet. J. Dairy Sci. 76:1114-1124.

Kronfeld, D.S., S. Donoghue, J.M.Naylor, K. Johnson and C.A. Bradley. 1980. Metabolic effects of feeding protected tallow to dairy cows. J. Dairy Sci. 63:545552.

Sklan, D., U. Moallem and Y. Folman. 1991. Effect of feeding calcium soaps of fatty acids on production and reproductive responses in high producing lactating cows. J. Dairy Sci. 74:510-517.

Smith, et al. 1978. Effects of feeding protected tallow to dairy cows in early lactation. J. Dairy Sci. 61:747-756.

Spicer, L.J., A. Alpizar, and S.E. Ecternkamp. 1993. Effects of insulin, insulin-like growth factor 1, and gonadotropins on bovine granulosa cell proliferation, progesterone production, estradiol production, and (or) insulin-like growth factor I production in vitro. J. Anim. Sci.

Spicer, L.J., W.B. Tucker. and G.D. Adams. 1990. Insulin-like growth factor-I in dairy cows: Relationships among energy balance, body condition score, ovarian activity, and estrous behavior. J. Dairy Sci. 73:929-937.

Spicer, L.J., R.K. Vernon, W.B. Tucker, R.P. Wettemann, J.F. Hogue, and G.D. Adams. 1993. Effects of inert fat on energy balance, plasma concentrations of hormones and reproduction in dairy cows. J. Dairy Sci. 76:2664-2673.

Staples, C.R. and W.W. Thatcher. 1990. Relationship between ovarian activity and energy status during the early postpartum period of high producing dairy cows. J. Dairy Sci.73:938-947.

Talavera, F., C.S. Park and G.L. Williams. 1985. Relationships among dietary lipid intake, serum cholesterol and ovarian function in Holstein heifers. J. Anim. Sci. 60:1045-1051.

Villa-Godoy, A., T.L. Hughes, R.S. Emery, L.T. Chapin and R.L. Fogwell. 1988. Association between energy balance and luteal function in lactating cows. J. Dairy Sci. 71:1063-1072.

Johnson J L et al: "Cell wall composition and deoxyribonucleic acid similarities among the anaerobic coryneforms, classical propionibacteria, and strains of *Arachnia propionica*" Journal of Bacteriology, Mar. 1972, vol. 109, No. 3, Mar. 1972, pp. 1047-1066, XP002348691, ISSN: 0021-9193, abstract; tables 1, 3, 5.

Bennett, J. W. and M. Klich. 2003. Mycotoxins. Clin. Microbiol. Rev. 16(3):497-516.

He, P., L. G. Young, and C. Forsberg. 1993. Microbially detoxified vomitoxin-contaminated corn for young pigs. J. Anim. Sci. 71:963-967.

Spurlock, M. E. 1997. Regulation of metabolism and growth during immune challenge: an overview of cytokine function. J. Anim. Sci. 75:1773-1783.

Metzler-Zebeli, B. U., Hooda, S., Pieper, R., Zijlstra, R. T., Van Kessel, A. G., Mosenthin, R. and G. Gänzle (2010). Polysaccharides Modulate Bacterial Microbiota, Pathways for Butyrate Production, and Abundance of Pathogenic *Escherichia coli* in the Pig Gastrointestinal Tract; J Appl Env Microbiol 76(11), 3692-3701.

Stein, H. H., B. Seve, M. F. Fuller, P. J. Moughan, and C. F. M. de Lange. 2007. Invited review: Amino acid bioavailability and digestibility in pig feed ingredients: Terminology and application. J. Anim. Sci. 85:172-180.

Spence, C., Whitehead, T. R. and M. A. Cotta (2008). Development and comparison of SYBR Green quantitative real-time PCR assays for detection and enumeration of sulfate reducing bacteria in stored swine manure. J Appl Microbiol 105, 2143-2152.

Yegani M., and D. R. Korver. 2008. Factors affecting intestinal health in poultry. Poult. Sci 87:2052-2063.

Abe, F et al, "Effect of administration of Bifidobacteria and lactic acid bacteria to newborn calves and piglets," J. Dairy Sci. (1995) 78:2838-2846.

Adami, A. et al, "Piglets fed from birth with the probiotic *Bacillus coagulans* as additive: zootechnical and microbiological aspects," Ann Microbiol Enzimol (1997) 47: 139-149.

Allison, M. J. et al, "Grain overload in cattle and sheep: Changes in microbial populations in the cecum and rumen," Amer. J. Vet Res. (1975) 36:181.

Awad, M M et al, "Synergistic effects of alpha-toxin and perfringolysin O in *Clostridium perfringens*-mediated gas gangrene," Infection & Immunity, 69(12):7904-7910, 2001.

Baker, A. et al, "Development of a *Bacillus subtilis* product for a large commercial swine farm to reduce *Clostridium perfringens* and *Clostridium difficile* in neonatal pigs," J. Anim. Sci. (2007) 85(suppl. 1):102.

Baker, G. C. et al, "Review and re-analysis of domain-specific 16S primers," Journal of Microbiological Methods (2003) 55:541-555.

Banach, S et al, "Prevalence, distribution and diversity of pathogenic *E. coli* in commercial turkey poult production," Presented at the Poultry Science Association Annual Meeting, Madison, WI, Jul. 2003.

Banach, S et al, "Prevalence, distribution and diversity of pathogenic *E. coli* in commercial turkey poult production," Poster #337, presented at the Poultry Science Association Annual Meeting, Madison, WI, Jul. 2003.

Barbosa, et al, "Applied and Environmental Microbiology," (Feb. 2005) vol. 71, 2:968-978.

Bembridge et al. "CD45RO expression on bovine T cells: relation to biological function," Immunology,(1995) 86:537-544.

Bertschinger, H U, "*Escherichia coli* infections," Diseases of Swine 8th Ed., Chap. 32, pp. 431-454, 1999.

Bikker, P. et al, "The influence of diet composition and an antimicrobial growth promoter on the growth response of weaned piglets to spray dried animal plasma." Livestock Prod. Sci. (2004) 86:201-208.

Billington et al., "*Clostridium perfringens* Type E animal enteritis isolates with highly conserved, silent enterotoxin gene sequences," Infect. Immun. (1998) 66(9):4531-4536.

Blood, D C, "Diseases caused by bacteria," Veterinary Medicine, 7th Ed., Bailliere, pp. 637-640, 1989.

Bosi, P. et al, "Effect of different spray dried plasmas on growth, ileal digestibility, nutrient deposition, immunity and health of early-weaned pigs challenged with *E. coli* K88," Asian-Aust. J. Anim. Sci. (2001) 14:1138-1143.

Bosi, P. et al, "Spray-dried plasma improves growth performance and reduces inflammatory status of weaned pigs challenged with enterotoxigenic *Escherichia coli* K88," J. Anim. Sci. (2004) 82:1764-1772.

Bosworth, B T et al. "Identification of toxin and pilus genes in porcine *Escherichia coli* using Polymerase Chain Reaction (PCR) with multiple primer pairs," Abstracts of the 97th General Meeting of the Am Society for Microbiology, May 4-8, 1997.

Brosius, J et al, "Complete nucleotide sequence of a 16S ribosomal RNA gene from *Escherichia coli*," Proc Natl Acad Sci USA 75(10:4801-4805, Oct. 1978.

Brown, D. C. et al, "The influence of different management systems and age on intestinal morphology, immune cell numbers and mucin production from goblet cells in post-weaning pigs," Vet. Immunol. Immunopath (2006a) 111:187-198.

Brown, D. C. et al, "Ontogeny of T lymphocytes and intestinal morphological characteristics in neonatal pigs at different ages in the postnatal period," J. Anim. Sci. (2006b) 84:567-578.

Carr, D et al, "Excessive mortality in market-age turkeys associated with cellulitis," Avian Disease 40:736-741, 1996.

Cera, K. R. et al, "Effect of age, weaning and post-weaning diet on small intestinal growth and small intestinal morphology in young swine," J. Anim. Sci. (1988) 66:574.

Clean Air "HM Composter and Odor Eliminator," (1 pg).

Coffey, R. et al, "The impact of environment and antimicrobial agents on the growth response of early weaned pigs to spray-dried porcine plasma," J. Anim. Sci. (1995) 73:2532-2539.

Cooper, V, "Diagnosis of neonatal pig diarrhea, "Vet Clinics N Am Food Animal Practice, 16(1):117-161 (2000).

"Copy for immediate release" 'Online! Jan. 13, 2005, pp. 1-2 XP002342562, retrieved from the Internet: URL: http://www.

(56) References Cited

OTHER PUBLICATIONS agtechproducts.com/press/DSM_Market_Microsource.pdf>, p. 1, line 1-line 15, p. 2, paragraph 4-last paragraph. [source: PCT/US05/017141 ISR].

Cromwell, G. L., "Antimicrobial and promicrobial agents. In: A. J. Lewis and L. L. Southern (eds.)," Swine Nutrition. p. 611. CRC Press, Boca Raton, FL (2001).

Cruywagen, C. W. et al, "Effect of *Lactobacillus acidophilus* supplementation of milk replacer on preweaning performance of calves," J. Dairy Sci. (1996) 79:483-486.

Davis. M. E. et al, "Effect of direct-fed microbial and antibiotic supplementation on gastrointestinal microflora, mucin histochemical characterization, and immune populations of weanling pigs," Livestock. Sci. (2007) 108:249-253.

Davis, M.E. et al, "Comparison of direct-fed microbial and antibiotic supplementation on innate and adaptive immune characteristics of weaning pigs," Reprod. Nutr. Dev. (2006) 46(Suppl.1):S63.

Davis, M. E. et al, "Rearing environment affects T lymphocyte populations within the systemic circulation and the gastrointestinal tract of young pigs.," Experimental Biology meeting abstracts [on CD ROM]. (2005) The FASEB Journal, 19, Abstract #43.7.

Davis, M.E. et al. "Dietary supplementation with phosphorylated mannans improves growth response and modulates immune function in weanling pigs," J. Anim. Sci. (2004) 82:1882-1891.

Davis, M. E. et al, "Inhalation Toxicology in the Equine Respiratory Tract," In: Equine Respiratory Diseases, P. Lekeux. International Veterinary Information Service (2002).

Dean-Nystrom, E et al, "Edema disease: a re-emerging problem?," Am Assoc of Swine Veterinarians, pp. 223-224, 2001.

Donald, J, "Treating poultry house floors to improve performance," The Poultry Engineering, Economics & Management Newsletter, Issue No. 23, 4 pgs, May 2003.

Donovan, D. C., "Growth and health of Holstein calves fed milk replacers supplemented with antibiotics or enteroguard," J. Dairy Sci. (2002) 85:947-950.

Dritz, S. et al, "Growth and microbial flora of nonmedicated, segregated, early weaned pigs from a commercial swine operation," JAVMA (1996) 208:711.

Dunlop, R. H., "Pathogenesis of ruminant lactic acidosis," Adv. Vet Sci. Comp Med. (1972) 16:259.

Ecological Laboratories, "Microbe-Lift equine products," EQ1, EQ2 and EQ3 (May 2001) (1 pg).

Elam, C. J. "Acidosis in feedlot cattle: Practical observations," J. Anim. Sci. (1976) 43:898.

Fangman, T. et al, "Segregated early weaning," Swine Health Prod. (1997) 5:195.

Francis, D, "Post-weaning *E. coli*-diagnosis, treatment, control, and its effect on subsequent growth performance," Am Assoc of Swine Veterinarians, 495-499, 2004.

Fritts, C A et al, "*Bacillus subtilis* C-3102 (Calsporin) improves live performance and microbioligical status of broiler chickens," Applied Poultry Science, Inc., 9:149-155, 2000.

Fuller, R., "Introduction. In: R. Fuller (Ed.). Probiotics 2: applications and practical aspects," Chapman and Hall, New York. (1997) p. 1.

Gaskins, H. R., "Intestinal bacteria and their influence on swine growth In: Austin J. Lewis and Lee L. Southern (Ed.)," Swine Nutrition 2nd Edition. (2001) p. 585-608.

Gebert, S. et al, "Development of a direct fed microbial to control pathogens associated with turkey poult production," Poult. Sci. (2006) 85(suppl. 1):71.

Gebert, S. et al, "Effect of a *Bacillus*-based direct-fed microbial on turkey poult performance and changes within the gastrointestinal microflora," J. Anim. Sci. (2007) 85(suppl. 1):249.

Grimes, J L et al, "Heat treatment of turkey litter for reuse as bedding," Int J of Poultry Science 2(5):287-292, 2003.

Hammer, C. et al, "Characterization of a colostrum replacer and a colostrum supplement containing IgG concentrate and growth factors," J. Dairy. Sci. (2004) 87:106-111.

Hatheway, C. L. "Toxigenic Clostridia," Clinical Microbiology Reviews (1990) 3(1):66-98.

Fernandez, D. "A Longitudinal Study Evaluating Effects of the Probiotic (Microtreat-P) on the Incidence of *Escherichia coli*", Department of Population Health and pathobiology, NC State University (date unknown).

Dasgupta, T., "A gel delivery system for coccidiosis vaccine: Uniformity of distribution of oocysts", Can Vet J vol. 41, Aug. 2000. pp. 613-616.

Barefoot, S. F., and T. R. Klaenhammer. 1983. Detection and activity of lactacin B, a bacteriocin produced by *Lactobacillus acidophilus*. Applied and Environmental Microbiology 45:1808-1815.

Berg, R. D., and W. E. Owens. 1979. Inhibition of translocation of viable *Escherichia coli* from the gastrointestinal tract of mice by bacterial antagonism. Infection and Immunity 25:820-827.

Cintas, L. M., M. P. Casaus, C. Herranz, I. F. Nes, and P. E. HernÃindez. 2001. Review: Bacteriocins of Lactic Acid Bacteria. Food Science and Technology International 7:281-305.

Fang, W., M. Shi, L. Huang, J. Chen, and Y. Wang. 1996. Antagonism of lactic acid bacteria towards *Staphylococcus aureus* and *Escherichia coli* on agar plates and in milk. Vet Res 27:3-12.

Gebert, S., E. Davis, T. Rehberger, and C. Maxwell. *Lactobacillus brevis* strain 1E1 administered to piglets through milk supplementation prior to weaning maintains intestinal integrity after the weaning event Beneficial Microbes 2:35.

Hugo, A. A., E. Kakisu, G. L. De Antoni, and P. F. Pérez. 2008. *Lactobacilli* antagonize biological effects of enterohaemorrhagic *Escherichia coli* in vitro. Letters in Applied Microbiology 46:613.

Jin, L.-Z., R. R. Marquardt, and S. K. Baidoo. 2000. Inhibition of enterotoxigenic *Escherichia coli* K88, K99 and 987P by the *Lactobacillus* isolates from porcine intestine. Journal of the Science of Food and Agriculture 80:619.

Jin L. Z. Y. W. Ho, N. Abdullah, M. A. Ali, and S. Jalaludin. 1996. Antagonistic effects of intestinal *Lactobacillus* isolates on pathogens of chicken. Letters in Applied Microbiology 23:67.

Lewus, C. B., A. Kaiser, and T. J. Montville. 1991. Inhibition of food-borne bacterial pathogens by bacteriocins from lactic acid bacteria isolated from meat. Applied and Environmental Microbiology 57:1683-1688.

Reid, G., and J. Burton. 2002. Use of *Lactobacillus* to prevent infection by pathogenic bacteria. Microbes and Infection 4:319.

Vold, L., A. Hoick, Y. Wasteson, and H. Nissen. 2000. High levels of background flora inhibits growth of *Escherichia coli* O157:H7 in ground beef. International Journal of Food Microbiology 56:219.

Galina_Pantoja, L. et al., "Relationship between immune cell phenotypes and pig growth in a commercial farm," Animal Biotechnology, (2006) 17: 81-98.

Kegg. Nucleotide Codes, Amino Acid Codes, and Genetic Codes, May 13, 2006 [online]. [Retrieved Apr. 27, 2010.] Retrieved from internet: <URL; http://web.archive.org/web/20060823201312/http://www.genome.jp/kegg/catalog/codes1.html>.

Zhou, T., "Microbial transformation of trichothecene mycotoxins", World Mycotoxin Journal, Feb. 2008; 1(1): 23-30.

Young, C.J., "Degradation of trichothecene mycotoxins by chicken intestinal microbes", Food and Chemical Toxicology 45 (2007) 136-143.

Kollarczik, B., "In Vitro Transformation of the Fusarium Mycotoxins Deoxynivalenol and Zearalenone by the Normal Gut Microflora of Pigs", natural Toxins 2:105-110 (1994).

Yan, F., "Soluble Proteins Produced by Probiotic Bacteria Regulate Intestinal Epithelial Cell Survival and Growth", Gastroenterology (2207) 132:562-575.

Marin, D.E., "Effect of *Lactobacillus* feed supplement in deoxynivalenol intoxicated piglets", Archive Zootechnica 13:1, 12-22, (2010).

Cheng, B., "Detoxification of Deoxynivalenol by *Bacillus* Strains", Journal of Food Safety, vol. 30 May 1, 2010, 599-614.

Skjolaas, K.A., "Effects of *Salmonella enterica* serovar *Typhimurium*, or serovar *Choleraesuis*, *Lactobacillus reuteri* and *Bacillus licheniformis* on chemokine and cytokine expression in the swine jejunal epithelial cell line, IPEC-J2", Vet. Immunology and Immunopathology, Elsevier BV, vol. 115, No. 3-4, Jan. 20, 2007.

(56) References Cited

OTHER PUBLICATIONS

International Search Report for PCT. App. No. PCT/US2012/051452 mailed on Apr. 26, 2013.

International Search Report for PCT App. No. PCT/US2012/052360 mailed Jan. 16, 2013.

First Office action (and English translation of pertinent portion) for Chinese patent application No. 201280052430.7 received Mar. 24, 2015, 12 pages.

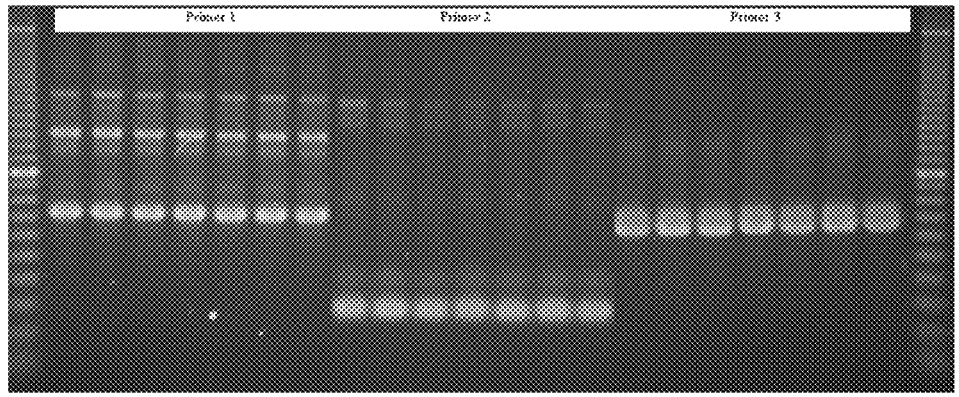

Figure 1

```
                    CTATACNTGCNAGTCGAGCGGACAGATGGGAGCTTGCTCCCTGA
TGTTAGCGGCGGACGGGTGAGTAACACGTGGGTAACCTGCCTGTAAGACTGGGATAACTC
CGGGAAACCGGGGCTAATACCGGATGGTTGTTTGAACCGCATGGTTCAAACATAAAAGGT
GGCTTCGGCTACCACTTACAGATGGACCCGCGGCGCATTAGCTAGTTGGTGAGGTAACGG
CTCACCAAGGCAACGATGCGTAGCCGACCTGAGAGGGTGATCGGCCACACTGGGACTGAG
ACACGGCCCAGACTCCTACGGGAGGCAGCAGTAGGGAATCTTCCGCAATGGACGAAAGTC
TGACGGAGCAACGCCGCGTGACTGATGAAGGTTTTCGGATCGTAAAGCTCTGTTGTTAGG
GAAGAACAAGTACCGTTCGAATAGGGCGGTACCTTGACGGTACCTAACCAGAAAGCCACG
GCTAACTACGTGCCAGCAGCCGCGGTAATACGTAGGTGGCAAGCGTTGTCCGGAATTATT
GGGCGTAAAGGGCTCGCAGGCCGGTTTCTTAAGTCTGATGTGAAAGCCCCCGGCTCAACCG
GGGAGGGTCATTGGAAACTGGGGAACTTGAGTGCAGAAGAGGAGAGTGGAATTCCACGTG
TAGCGGTGAAATGCGTAGAGATGTGGAGGAACACCAGTGGCGAAGGCGACTCTCTGGTCT
GTAACTGACGCTGAGGAGCGAAAGCGTGGGGAGCGAACAGGATTAGATACCCTGGTAGTC
CACGCCGTAAACGATGAGTGCTAAGTGTTAGGGGGTTTCCGCCCCTTAGTGCTGCAGCTA
ACGCATTAAGCACTCCGCCTGGGGAGTACGGTCGCAAGACTGAAACTCAAAGGAATTGAC
GGGGGCCCGCACAAGCGGTGGAGCATGTGGTTTAATTCGAAGCAACGCGAAGAACCTTAC
CAGGTCTTGACATCCTCTGACAATCCTAGAGATAGGACGTCCCCTTCGGGGGCAGAGTGA
CAGGTGGTGCATGGTTGTCGTCAGCTCGTGTCGTGAGATGTTGGGTTAAGTCCCGCAACG
AGCGCAACCCTTGATCTTAGTTGCCAGCATTCAGTTGGGCACTCTAAGGTGACTGCCGGT
GACAAACCGGAGGAAGGTGGGGATGACGTCAAATCATCATGCCCCTTATGACCTGGGCTA
CACACGTGCTACAATGGACAGAACAAAGGGCAGCGAAACCGCGAGGTTAAGCCAATCCCA
CAAATCTGTTCTCAGTTCGGATCGCAGTCTGCAACTCGACTGCGTGAAGCTGGAATCGCT
AGTAATCGCGGATCAGCATGCCGCGGTGAATACGTTCCCGGGCCTTGTACACACCGCCCG
TCACACCACGAGAGTTTGTAACACCCGAAGTCGGTGAGGTAACCTTTTAGGAGCCAGCCG
CCGAAGGTGGGACAGATGATTCGGGTGAAGTCGTAACAAGGTAGCCGTATCGGAAGGTGC
GGTTGG
```

Figure 2

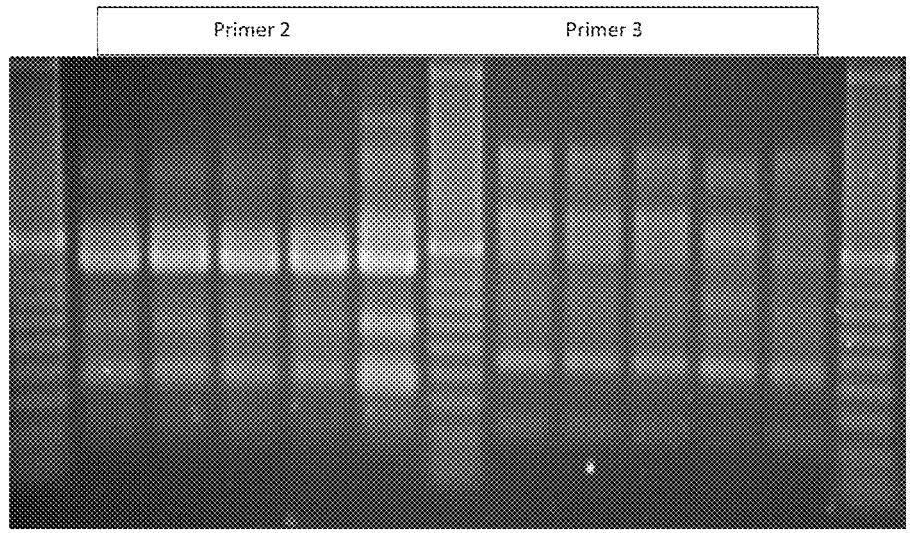

Figure 3

```
ACATGCAGTCGAGCGGACAGATGGGAGCTTGCTCCCTGATGTT
AGCGGCGGACGGGTGAGTAACACGTGGGTAACCTGCCTGTAAGACTGGGATAACTCCGGG
AAACCGGGGCTAATACCGGATGGTTGTCTGAACCGCATGGTTCAGACATAAAAGGTGGCT
TCGGCTACCACTTACAGATGGACCCGCGGCGCATTAGCTAGTTGGTGAGGTAACGGCTCA
CCAAGGCGACGATGCGTAGCCGACCTGAGAGGGTCATCGGCCACACTGGGACTGAGACAC
GGCCCAGACTCCTACGGGAGGCAGCAGTAGGGAATCTTCCGCAATGGACGAAAGTCTGAC
GGAGCAACGCCGCGTGAGTGATGAAGGTTTTCGGATCGTAAAGCTCTGTTGTTAGGGAAG
AACAAGTGCCGTTCAAATAGGGCGGCACCTTGACGGTACCTAACCAGAAAGCCACGGCTA
ACTACGTGCCAGCAGCCGCGGTAATACGTAGGTGGCAAGCGTTGTCCGGAATTATTGGGC
GTAAAGGGCTCGCAGGCGGTTTCTTAAGTCTGATGTGAAAGCCCCCGGCTCAACCGGGGA
GGGTCATTGGAAACTGGGGAACTTGAGTGCAGAAGAGGAGAGTGGAATTCCACGTGTAGC
GGTGAAATGCGTAGAGATGTGGAGGAACACCAGTGGCGAAGGCGACTCTCTGGTCTGTAA
CTGACGCTGAGGAGCGAAAGCGTGGGGAGCGAACAGGATTAGATACCCTGGTAGTCCACG
CCGTAAACGATGAGTGCTAAGTGTTAGGGGGTTTCCGCCCCTTAGTGCTGCAGCTAACGC
ATTAAGCACTCCGCCTGGGGAGTACGGTCGCAAGACTGAAACTCAAAGGAATTGACGGGG
GCCCGCACAAGCGGTGGAGCATGTGGTTTAATTCGAAGCAACGCGAAGAACCTTACCAGG
TCTTGACATCCTCTGACAATCCTAGAGATAGGACGTCCCCTTCGGGGCAGAGTGACAGG
TGGTGCATGGTTGTCGTCAGCTCGTGTCGTGAGATGTTGGGTTAAGTCCCGCAACGAGCG
CAACCCTTGATCTTAGTTGCCAGCATTCAGTTGGGCACTCTAAGGTGACTGCCGGTGACA
AACCGGAGGAAGGTGGGGATGACGTCAAATCATCATGCCCCTTATGACCTGGGCTACACA
CGTGCTACAATGGACAGAACAAAGGGCAGCGAAACCGCGAGGTTAAGCCAATCCCACAAA
TCTGTTCTCAGTTCGGATCGCAGTCTGCAACTCGACTGCGTGAAGCTGGAATCGCTAGTA
ATCGCGGATCAGCATGCCGCGGTGAATACGTTCCCGGGCCTTGTACACACCGCCCGTCAC
ACCACGAGAGTTTGTAACACCCGAAGTCGGTGAGGTAACCTTTATGGAGCCAGCCGCCGA
AGGTGGGACAGATGATTGGGGNGAAGTC
```

Figure 4

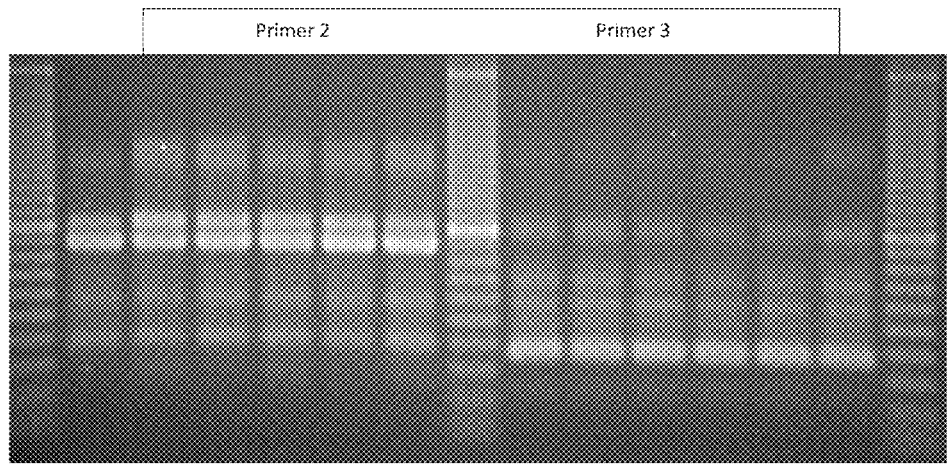

Figure 5

```
                        TGCAGTCCAGCGGACAGATGGGAGCTTGCTCCCTGAT
GTTAGCGGCGGACGGGTGAGTAACACGTGGGTAACCTGCCTGTAAGACTGGGATAACTCC
GGGAAACCGGGGCTAATACCGGATGGTTGTTTGAACCGCATGGTTCAGACATAAAAGGTG
GCTTCGGCTACCACTTACAGATGGACCCGCGGCGCATTAGCTAGTTGGTGAGGTAACGGC
TCACCAAGGCGACGATGCGTAGCCGACCTGAGAGGGTGATCGGCCACACTGGGACTGAGA
CACGGCCCAGACTCCTACGGGAGGCAGCAGTAGGGAATCTTCCGCAATGGACGAAAGTCT
GACGGAGCAACGCCGCGTGAGTGATGAAGGTTTTCGGATCGTAAAGCTCTGTTGTTAGGG
AAGAACAAGTGCCGTTCAAATAGGGCGGCACCTTGACGGTACCTAACCCAGAAAGCCACG
GCTAACTACGTGCCAGCAGCCGCGGTAATACGTAGGTCGCAAGCGTTGTCCGGAATTAT
TGGGCGTAAAGGGCTCGCAGGCGGTTTCTTAAGTCTGATGTGAAAGCCCCCGGCTCAACC
GGGGAGGGTCATTGGAAACTGGGGAACTTGAGTGCAGAAGAGGAGAGTGGAATTCCACGT
GTAGCGGTGAAATGCGTAGAGATGTGGAGGAACACCAGTGGCGAAGGCGACTCTCTGGTC
TGTAACTGACGCTGAGGAGCGAAAGCGTGGGGAGCGAACAGGATTAGATACCCTGGTAGT
CCACGCCGTAAACGATGAGTGCTAAGTGTTAGGGGGTTTCCGCCCCTTAGTGCTGCAGCT
AACGCATTAAGCACTCCGCCTGGGGAGTACGGTCGCAAGACTGAAACTCAAAGGAATTGA
CGGGGGCCCGCACAAGCGGTGGAGCATGTGGTTTAATTCGAAGCAACGCGAAGAACCTTA
CCAGGTCTTGACATCCTCTGACAATCCTAGAGATAGGACGTCCCCTTCGGGGGCAGAGTG
ACAGGTGGTGCATGGTNGTCGTCAGCTCGTGTCGTGAGATGTTNGGGTTAAGTCCCGCA
ACGAGCGCAACCCTTGATCTTAGTTGCCAGCATTCAGTTGGGCACTCTAAGGTGACTGCC
GGTGACAAACCGGAGGAAGGTGGGGATGACGTCAAATCATCATGCCCCTTATGACCTGGG
CTACACACGTGCTACAATGGACAGAACAAAGGGCAGCGAAACCGCGAGGTTAAGCCAATC
CCACAAATCTGTTCTCAGTTCGGATCGCAGTCTGCAACTCGACTGCGTGAAGCTGGAATC
GCTAGTAATCGCGGATCAGCATGCCGCGGTGAATACGTTCCCGGGCCTTGTACACACCGC
CCGTCACACCACGAGAGTTTGTAACACCCGAAGTCGGTGAGGTAACCTTTATGGAGCCAG
CCGCCGAAGGTGGGACAGATGATTGGGGNCAACT
```

Figure 6

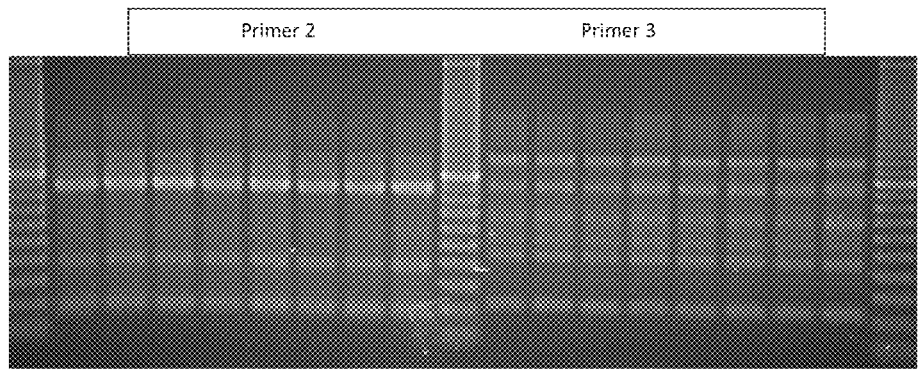

Figure 7

```
                          CNATACNTGCAGTCGAGCGGACAGATGGGAGCTTGCTCCCTGAT
GTTAGCGGCGGACGGGTGAGTAACACGTGGGTAACCTGCCTGTAAGACTGGGATAACTCC
GGGAAACCGGGGCTAATACCGGATGGTTGTCTGAACCGCATGGTTCAGACATAAAAGGTG
GCTTCGGCTACCACTTACAGATGGACCCGCGGCGCATTAGCTAGTTGGTGAGGTAACGGC
TCACCAAGGCGACGATGCGTAGCCGACCTGAGAGGGTGATCGGCCACACTGGGACTGAGA
CACGGCCCAGACTCCTACGGGAGGCAGCAGTAGGGAATCTTCCGCAATGGACGAAAGTCT
GACGGAGCAACGCCGCGTGAGTGATGAAGGTTTTCGGATCGTAAAGCTCTGTTGTTAGGG
AAGAACAAGTGCCGTTCAAATAGGGCGGCANCCTTCACGGTACCTAACCAGAAAGCCACG
GCTAACTACGTGCCAGCAGCCGCGGTAATACGTAGGTGGCAAGCGTTGTCCGGAATTAT
TGGGCGTAAAGGGCTCGCAGGCGGTTTCTTAAGTCTGATGTGAAAGCCCCCGGCTCAACC
GGGGAGGGTCATTGGAAACTGGGGAACTTGAGTGCAGAAGAGGAGAGTGGAATTCCACGT
GTAGCGGTGAAATGCGTAGAGATGTGGAGGAACACCAGTGGCGAAGGCGACTCTCTGGTC
TGTAACTGACGCTGAGGAGCGAAAGCGTGGGGAGCGAACAGGATTAGATACCCTGGTAGT
CCACGCCGTAAACGATGAGTGCTAAGTGTTAGGGGGTTTTCCGCCCCTTAGTGCTGCAGC
TAACGCANTTAAGCACTCCGCNCTGGGGACTACGGTCGCAAGACTGAAACTCAAAGCAAT
TGACGGGGGCCCGCACAAGCGGTGGAGCATGTGGTTTAATTCGAAGCAACGCGAAGAACC
TTACCAGGTCTTGACATCCTCTGACAATCCTAGAGATAGGACGTCCCCTTCGGGGCGACA
GTGACAGGTGGTGCATGGTTGTCGTCAGCTCGTGTCGTGAGATGTTGGGTTAAGTCCCGC
AACGAGCGCAACCCTTGATCTTAGTTGCCAGCATTCAGTTGGGCACTCTAAGGTGACTGC
CGGTGACAAACCGGAGGAAGGTGGGGATGACGTCAAATCATCATGCCCCTTATGACCTGG
GCTACACACGTGCTACAATGGACAGAACAAAGGGCAGCGAAACCGCGAGGGTAAGCCAAT
CCCACAAATCTGTTCTCAGTTCGGATCGCAGTCTGCAACTCGACTGCGTGAAGCTGGAAT
CGCTAGTAATCGCGGATCAGCATGCCGCGGTGAATACGTTCCCGGGCCTTGTACACACCG
CCCGTCACACCACGAGAGTTTGTAACACCCGAAGTCGGTGAGGTAACCTTTTAGGAGCCA
GCCGCCGAAGGTGGGACAGATGATTGGGGNGAAGTC
```

Figure 8

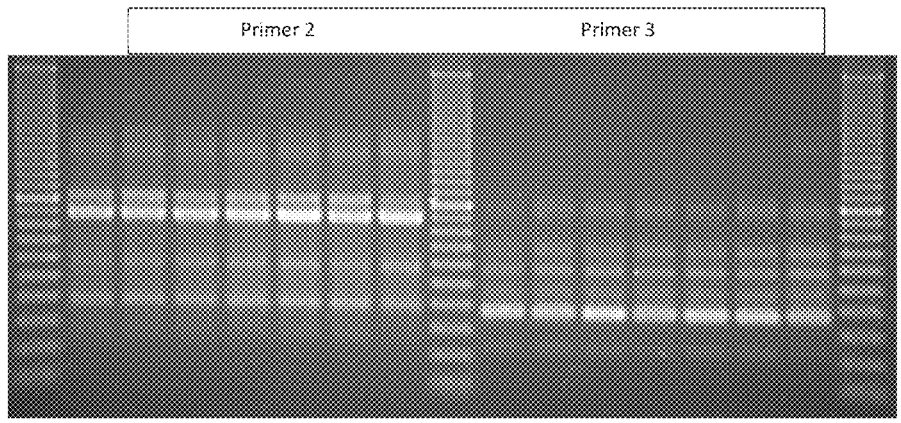

Figure 9

```
                              TGCAGTCGAGCGGACAGATGGGAGCTTGCTCCCTGATGT
TAGCGGCGGACGGGTGAGTAACACGTGGGTAACCTGCCTGTAAGACTGGGATAACTCCGG
GAAACCGGGGCTAATACCGGATGGTTGTTTGAACCGCATGGTTCAGACATAAAAGGTGGC
TTCGGCTACCACTTACAGATGGACCCGCGGCGCATTAGCTAGTTGGTGAGGTAACGGCTC
ACCAAGGCGACGATGCGTAGCCGACCTGAGAGGGTGATCGGCCACACTGGGACTGAGACA
CGGCCCAGACTCCTACGGGAGGCAGCAGTAGGGAATCTTCCGCAATGGACGAAAGTCTGA
CGGAGCAACGCCGCGTGAGTGATGAAGGTTTTCGGATCGTAAAGCTCTGTTGTTAGGGAA
GAACAAGTGCCGTTCAAATAGGGCGGCACCTTGACGGTACCTAACCAGAAAGCCACGGCT
AACTACGTGCCAGCAGCCGCGGTAATACGTAGGTGGCAAGCGTTGTCCGGGAATTATTGG
GCGTAAAGGGCTCGCAGGCGGTTTCTTAAGTCTGATGTGAAAGCCCCCGGCTCAACCGCG
GAGGGTCATTGGAAACTGGGGAACTTGAGTGCAGAAGAGGAGAGTGGAATTCCACGTGTA
GCGGTGAAATGCGTAGAGATGTGGAGGAACACCAGTGGCGAAGGCGACTCTCTGGTCTGT
AACTGACGCTGAGGAGCGAAAGCGTGGGGAGCGAACAGGATTAGATACCCTGGTAGTCCA
CGCCGTAAACGATGAGTGCTAAGTGTTAGGGGGTTTCCGCCCCTTAGTGCTGCAGCTAAC
GCATTAAGCACTCCGCCTGGGGAGTACGGTCGCAAGACTGAAACTCAAAGGAATTGACGG
GGGCCCGCACAAGCGGTGGAGCATGTGGTTTAATTCGAAGCAACGCGNAAGAACCTTACC
AGGTCTTGACATCCTCTGACAATCCTAGAGATAGGACGTCCCCTTCGGGGGCAGAGTGAC
AGGTGGTNGCATGGTTGTCGTCAGCTCGTGTCGTGAGATGTTGGGTTAAGTCCCGCAACG
AGCGCAACCCTTGATCTTAGTTGCCAGCATTCAGTTGGGCACTCTAAGGTGACTGCCGGT
GACAAACCGGAGGAAGGTGGGGATGACGTCAAATCATCATGCCCCTTATGACCTGGGCTA
CACACGTGCTACAATGGACAGAACAAAGGGCAGCGAAACCGCGAGGTTAAGCCAATCCCA
CAAATCTGTTCTCAGTTCGGATCGCAGTCTGCAACTCGACTGCGTGAAGCTGGAATCGCT
AGTAATCGCGGATCAGCATGCCGCGGTGAATACGTTCCCGGGCCTTGTACACACCGCCG
TCACACCACGAGAGTTTGTAACACCCGAACTCGGTCAGGTAACCTTTATCGAGCCAGCCG
CCGAAGGTGGGACAGATGATNGGGGNGAAGTCG
```

Figure 10

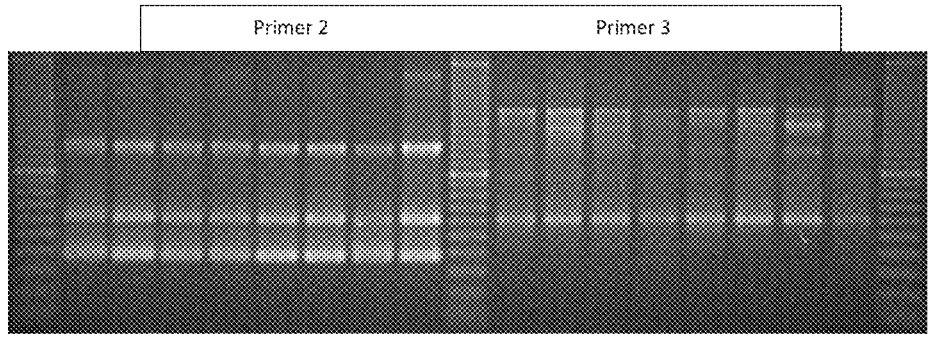

Figure 11

```
TATACNTGCAGTCGAGCGGACAGAAGGGAGCTTGCTCCCGGATGT
TAGCGGCGGACGGGTGAGTAACACGTGGGTAACCTGCCTGTAAGACTGGGATAACTCCGG
GAAACCGGAGCTAATACCGGATAGTTCCTTGAACCGCATGGTTCAAGGATGAAAGACGGT
TTCGGCTGTCACTTACAGATGGACCCGCGGCCCATTAGCTAGTTGGTGGGGTAATGGCTC
ACCAAGGCGACGATGCGTAGCCGACCTGAGAGGGTGATCGGCCACACTGGGACTGAGACA
CGGCCCAGACTCCTACGGGAGGCAGCAGTAGGGAATCTTCCGCAATGGACGAAAGTCTGA
CGGAGCAACGCCGCGTGAGTGATGAAGGTTTTCGGATCGTAAACCTCTGTTGTTAGGGCAA
GAACAAGTGCGAGAGTAACTGCTCGCACCTTGACGGTACCTAACCAGAAAGCCACGGCTA
ACTACGTGCCAGCAGCCGCGGTAATACGTAGGTGGCAAGCGTTGTCCNGGAATTATTGGG
CGTAAAGGGCTCGCAGGCGGTTTCTTAAGTCTGATGTGAAAGCCCCCGGCTCAACCGGGG
AGGGTCATTGGAAACTGGGAAACTTGAGTGCAGAAGAGGAGAGTGGAATTCCACGTGTAG
CGGTGAAATGCGTAGAGATGTGGAGGAACACCAGTGGCGAAGGCGACTCTCTGGTCTGTA
ACTGACGCTGAGGAGCGAAAGCGTGGGGAGCGAACAGGATTAGATACCCTGGTAGTCCAC
GCCGTAAACGATGAGTGCTAAGTGTTAGGGGGTTTCCGCCCCTTAGTGCTGCAGCTAACG
CATTAAGCACTCCGCCTGGGCAGTACGGTCGCAAGACTGAAACTCAAAGGAATTGACGGG
GGCCCGCACAAGCGGTGGAGCATGTGGTTTAATTCGAAGCAACGCGAAGAACCTTACCAG
GTCTTGACATCCTCTGACAACCCTAGAGATAGGGCTTTCCCTTCGGGGACAGAGTGACAG
GTGGTGCATGGTTGTCGTCAGCTCGTGTCGTGAGATGTTGGGGTTAAGTCCCGCAACGAG
CGCAACCCTTGATCTTAGTTGCCAGCATTTAGTTGGGCACTCTAAGGTGACTGCCGGTGA
CAAACCGGAGGAAGGTGGGGATGACGTCAAATCATCATGCCCCTTATGACCTGGGCTACA
CACGTGCTACAATGGACAGAACAAAGGGCTGCGAGACCGCAAGGTTTAGCCAATCCCATA
AATCTGTTCTCAGTTCGGATCGCAGTCTGCAACTCGACTGCGTGAAGCTGGAATCGCTAG
TAATCGCGGATCAGCATGCCGCGGTGAATACGTTCCCGGGCCTTGTACACACCGCCCGTC
ACACCACGAGAGTTTGCAACACCCGAAGTCGGTGAGGTAACCNTTATGGAGCCAGCCGCC
GAAGGTGGGGCAGATGATNGGGGNGAAGTC
```

Figure 12

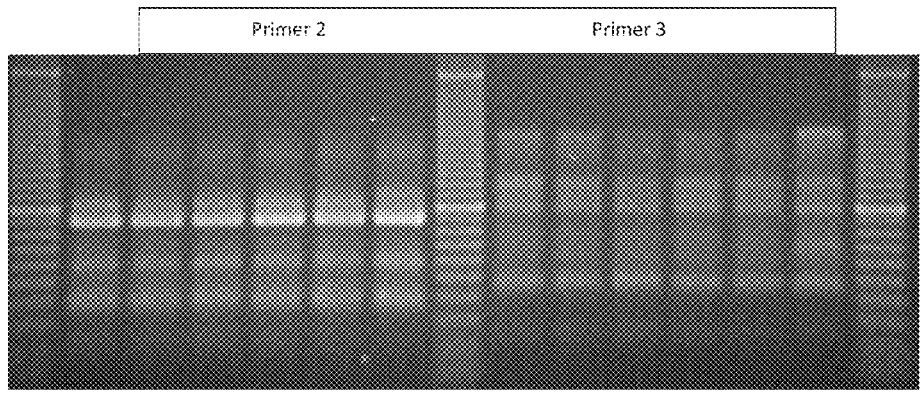

Figure 13

```
                        TGCAGTCGAGCGGACAGATGGGAGCTTGCTCCCTGATG
TTAGCGGCGGACGGGTGAGTAACACGTGGGTAACCTGCCTGTAAGACTGGGATAACTCCG
GGAAACCGGGGCTAATACCGGATGGTTGTCTGAACCCCATGGTTCAGACATAAAAGGTGG
CTTCGGCTACCACTTACAGATGGACCCGCGGCGCATTAGCTAGTTGGTGAGGTAACGGCT
CACCAAGGCGACGATGCGTAGCCGACCTGAGAGGGTGATCGGCCACACTGGGACTGAGAC
ACGGCCCAGACTCCTACGGGAGGCAGCAGTAGGGAATCTTCCGCAATGGACGAAAGTCTG
ACGGAGCAACGCCGCGTGAGTGATGAAGGTTTTCGGATCGTAAAGCTCTGTTGTTAGGGA
AGAACAAGTGCCGTTCAAATAGGGCGGCACCTTGACGGTACCTAACCAGAAAGCCACGGC
TAACTACGTGCCAGCAGCCGCGGTAATACGTAGGTGGCAAGCGTTGTCCGGGAATTATTG
GGCGTAAAGGGCTCGCAGGCGGTTTCTTAAGTCTGATGTGAAAGCCCCCGGCTCAACCGG
GGAGGGTCATTGGAAACTGGGGAACTTGAGTGCAGAAGAGGAGAGTGGAATTCCACGTGT
AGCGGTGAAATGCGTAGAGATGTGGAGGAACACCAGTGGCGAACGCGACTCTCTGGTCTG
TAACTGACGCTGAGGAGCGAAAGCGTGGGGAGCGAACAGGATTAGATACCCTGGTAGTCC
ACGCCGTAAACGATGAGTGCTAAGTGTTAGGGGGTTTCCGCCCCTTAGTGCTGCAGCTAA
CGCATTAAGCACTCCGCCTGGGGAGTACGGTCGCAAGACTGAAACTCAAAGGAATTGACG
GGGGCCCGCACAAGCGGTGGAGCATGTGGTTTAATTCGAAGCAACGCGAAGAACCTTACC
AGGTCTTGACATCCTCTGACAATCCTAGAGATAGGACGTCCCCTTTCGGGGGCAGAGTGA
CAGGTGGTNGCATGGTTGTCGTCAGCTCGTGTCGTGAGATGTTGGGGTTAAGTCCCGCAA
CGAGCGCAACCCTTGATCTTAGTTGCCAGCATTCAGTTGGGCACTCTAAGGTGACTGCCG
GTGACAAACCGGAGGAAGGTGGGGATGACGTCAAATCATCATGCCCCTTATGACCTGGGC
TACACACGTGCTACAATGGACAGAACAAAGGGCAGCGAAACCCGCGAGGTTAAGCCAATCC
CACAAATCTGTTCTCAGTTCGGATCGCAGTCTGCAACTCGACTGCGTGAAGCTGGAATCG
CTAGTAATCGCGGATCAGCATGCCGCGGTGAATACGTTCCCGGGCCTTGTACACACCGCC
CGTCACACCACGAGAGTTTGTAACACCCGAAGTCGGTGAGGTAACCTTTATGGAGCCAGC
CGCCGAAGGTGGGACAGATGANGGGGNNAAGT
```

Figure 14

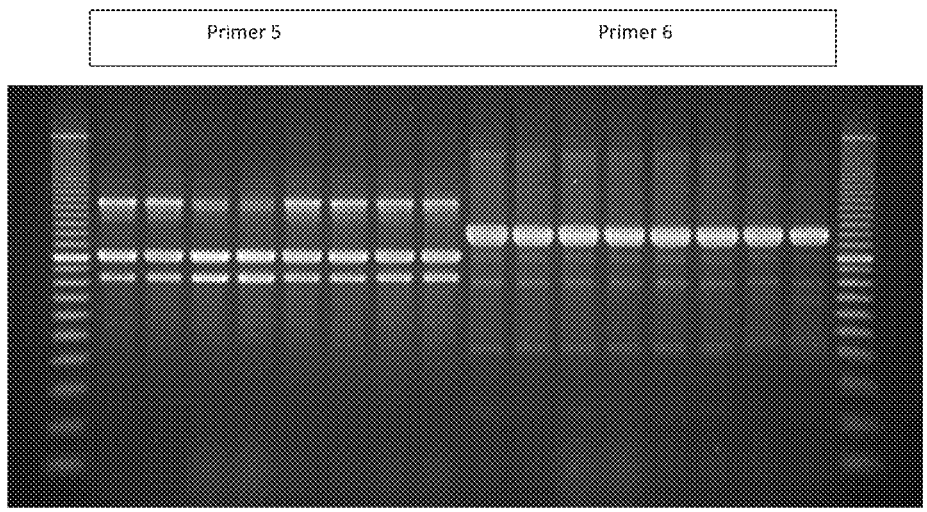

Figure 17

GGCTCAGGACGAACGCTGGCGGCGTGCCTAATACATGCAAGTCGAGCGGACAGATGGGAGCTTG
CTCCCTGATGTTAGCGGCGGACGGGTGAGTAACACGTGGGTAACCTGCCTGTAAGACTGGGATA
ACTCCGGGAAACCGGGGCTAATACCGGATGGTTGTTTGAACCGCATGGTTCAAACATAAAAGGT
GGCTTCGGCTACCACTTACAGATGGACCCGCGGCGCATTAGCTAGTTGGTGAGGTAACGGCTCA
CCAAGGCAACGATGCGTAGCCGACCTGAGAGGGTGATCGGCCACACTGGGACTGAGACACGGCC
CAGACTCCTACGGGAGGCAGCAGTAGGGAATCTTCCGCAATGGACGAAAGTCTGACGGAGCAAC
GCCGCGTGAGTGATGAAGGTTTTCGGATCGTAAAGCTCTGTTGTTAGGGAAGAACAAGTACCGT
TCGAATAGGGCGGTACCTTGACGGTACCTAACCAGAAAGCCACGGCTAACTACGTGCCAGCAGC
CGCGGTAATACGTAGGTGGCAAGCGTTGTCCGGAATTATTGGGCGTAAAGGGCTCGCAGGCGGT
TTCTTAAGTCTGATGTGAAAGCCCCCGGCTCAACCGGGGAGGGTCATTGGAAACTGGGGAACTT
GAGTGCAGAAGAGGAGAGTGGAATTCCACGTGTAGCGGTGAAATGCGTAGAGATGTGGAGGAAC
ACCAGTGGCGAAGGCGACTCTCTGGTCTGTAACTGACGCTGAGGAGCGAAAGCGTGGGGAGCGA
ACAGGATTAGATACCCTGGTAGTCCACGCCGTAAACGATGAGTGCTAAGTGTTAGGGGGTTTCC
GCCCCTTAGTGCTGCAGCTAACGCATTAAGCACTCCGCCTGGGGAGTACGGTCGCAAGACTGAA
ACTCAAAGGAATTGACGGGGGCCCGCACAAGCGGTGGAGCATGTGGTTTAATTCGAAGCAACGC
GAAGAACCTTACCAGGTCTTGACATCCTCTGACAATCCTAGAGATAGGACGTCCCCTTCGGGGG
CAGAGTGACAGGTGGTGCATGGTTGTCGTCAGCTCGTGTCGTGAGATGTTGGGTTAAGTCCCGC
AACGAGCGCAACCCTTGATCTTAGTTGCCAGCATTCAGTTGGGCACTCTAAGGTGACTGCCGGT
GACAAACCGGAGGAAGGTGGGGATGACGTCAAATCATCATGCCCCTTATGACCTGGGCTACACA
CGTGCTACAATGGACAGAACAAAGGGCAGCGAAACCGCGAGGTTAAGCCAATCCCACAAATCTG
TTCTCAGTTCGGATCGCAGTCTGCAACTCGACTGCGTGAAGCTGGAATCGCTAGTAATCGCGGA
TCAGCATGCCGCGGTGAATACGTTCCCGGGCCTTGTACACACCGCCCGTCACACCACGAGAGTT
TGTAACACCCGAAGTCGGTGAGGTAACCTTTTAGGAGCCAGCCGCCGAAGGTGGGACAGATGAT
TGGGGTGAAGTCGTAACAAGGTAGCCGTATCGGAAGGTG

Figure 18

```
CTCAGGACGAACGCTGGCGGCGTGCCTAATACATGCAAGTCGAGCGGACAGAAGGGAGCTTGCT
CCCGGATGTTAGCGGCGGACGGGTGAGTAACACGTGGGTAACCTGCCTGTAAGACTGGGATAAC
TCCGGGAAACCGGAGCTAATACCGGATAGTTCCTTGAACCGCATGGTTCAAGGATGAAAGACGG
TTTCGGCTGTCACTTACAGATGGACCCGCGGCGCATTAGCTAGTTGGTGGGGTAATGGCTCACC
AAGGCGACGATGCGTAGCCGACCTGAGAGGGTGATCGGCCACACTGGGACTGAGACACGGCCCA
GACTCCTACGGGAGGCAGCAGTAGGGAATCTTCCGCAATGGACGAAAGTCTGACGGAGCAACGC
CGCGTGAGTGATGAAGGTTTTCGGATCGTAAAGCTCTGTTGTTAGGGAAGAACAAGTGCGAGAG
TAACTGCTCGCACCTTGACGGTACCTAACCAGAAAGCCACGGCTAACTACGTGCCAGCAGCCGC
GGTAATACGTAGGTGGCAAGCGTTGTCCGGAATTATTGGGCGTAAAGGGCTCGCAGGCGGTTTC
TTAAGTCTGATGTGAAAGCCCCCGGCTCAACCGGGGAGGGTCATTGGAAACTGGGAAACTTGAG
TGCAGAAGAGGAGAGTGGAATTCCACGTGTAGCGGTGAAATGCGTAGAGATGTGGAGGAACACC
AGTGGCGAAGGCGACTCTCTGGTCTGTAACTGACGCTGAGGAGCGAAAGCGTGGGGAGCGAACA
GGATTAGATACCCTGGTAGTCCACGCCGTAAACGATGAGTGCTAAGTGTTAGGGGGTTTCCGCC
CCTTAGTGCTGCAGCTAACGCATTAAGCACTCCGCCTGGGGAGTACGGTCGCAAGACTGAAACT
CAAAGGAATTGACGGGGGCCCGCACAAGCGGTGGAGCATGTGGTTTAATTCGAAGCAACGCGAA
GAACCTTACCAGGTCTTGACATCCTCTGACAACCCTAGAGATAGGGCTTTCCCTTCGGGGACAG
AGTGACAGGTGGTGCATGGTTGTCGTCAGCTCGTGTCGTGAGATGTTGGGTTAAGTCCCGCAAC
GAGCGCAACCCTTGATCTTAGTTGCCAGCATTTAGTTGGGCACTCTAAGGTGACTGCCGGTGAC
AAACCGGAGGAAGGTGGGGATGACGTCAAATCATCATGCCCCTTATGACCTGGGCTACACACGT
GCTACAATGGACAGAACAAAGGGCTGCGAGACCGCAAGGTTTAGCCAATCCCATAAATCTGTTC
TCAGTTCGGATCGCAGTCTGCAACTCGACTGCGTGAAGCTGGAATCGCTAGTAATCGCGGATCA
GCATGCCGCGGTGAATACGTTCCCGGGCCTTGTACACACCGCCCGTCACACCACGAGAGTTTGC
AACACCCGAAGTCGGTGAGGTAACCTTTATGGAGCCAGCCGCCGAAGGTGGGGCAGATGATTGG
GGTGAAGTCGTAACAAGGTAGCCGTATCGGAAG
```

Figure 21

SEQUENCE LISTING

```
<160> NUMBER OF SEQ ID NOS: 16

<210> SEQ ID NO 1
<211> LENGTH: 10
<212> TYPE: DNA
<213> ORGANISM: Artificial Sequence
<220> FEATURE:
<223> OTHER INFORMATION: Primer for RAPD PCR analysis

<400> SEQUENCE: 1
ggtgcgggaa                                                              10

<210> SEQ ID NO 2
<211> LENGTH: 10
<212> TYPE: DNA
<213> ORGANISM: Artificial Sequence
<220> FEATURE:
<223> OTHER INFORMATION: Primer for RAPD PCR analysis

<400> SEQUENCE: 2
gtttcgctcc                                                              10

<210> SEQ ID NO 3
<211> LENGTH: 10
<212> TYPE: DNA
<213> ORGANISM: Artificial Sequence
<220> FEATURE:
<223> OTHER INFORMATION: Primer for RAPD PCR analysis

<400> SEQUENCE: 3
gtagacccgt                                                              10

<210> SEQ ID NO 4
<211> LENGTH: 10
<212> TYPE: DNA
<213> ORGANISM: Artificial Sequence
<220> FEATURE:
<223> OTHER INFORMATION: Primer for RAPD PCR analysis

<400> SEQUENCE: 4
aagagcccgt                                                              10

<210> SEQ ID NO 5
<211> LENGTH: 10
<212> TYPE: DNA
<213> ORGANISM: Artificial Sequence
<220> FEATURE:
<223> OTHER INFORMATION: Primer for RAPD PCR analysis

<400> SEQUENCE: 5
aacgcgcaac                                                              10

<210> SEQ ID NO 6
<211> LENGTH: 10
<212> TYPE: DNA
<213> ORGANISM: Artificial Sequence
<220> FEATURE:
<223> OTHER INFORMATION: Primer for RAPD PCR analysis

<400> SEQUENCE: 6
cccgtcagca                                                              10

<210> SEQ ID NO 7
<211> LENGTH: 20
<212> TYPE: DNA
<213> ORGANISM: Artificial Sequence
```

```
<220> FEATURE:
<223> OTHER INFORMATION: Primer used in screening assay

<400> SEQUENCE: 7
aggtcaacat cgccacctac                                                    20

<210> SEQ ID NO 8
<211> LENGTH: 20
<212> TYPE: DNA
<213> ORGANISM: Artificial Sequence
<220> FEATURE:
<223> OTHER INFORMATION: Primer used in screening assay

<400> SEQUENCE: 8
caacgggacg gtaatgaaac                                                    20

<210> SEQ ID NO 9
<211> LENGTH: 20
<212> TYPE: DNA
<213> ORGANISM: Artificial Sequence
<220> FEATURE:
<223> OTHER INFORMATION: Primer used in screening assay

<400> SEQUENCE: 9
gctctgtcgc aaggtaggac                                                    20

<210> SEQ ID NO 10
<211> LENGTH: 20
<212> TYPE: DNA
<213> ORGANISM: Artificial Sequence
<220> FEATURE:
<223> OTHER INFORMATION: Primer used in screening assay

<400> SEQUENCE: 10
ggccataagt gcctttacga                                                    20

<210> SEQ ID NO 11
<211> LENGTH: 20
<212> TYPE: DNA
<213> ORGANISM: Artificial Sequence
<220> FEATURE:
<223> OTHER INFORMATION: Primer used in screening assay

<400> SEQUENCE: 11
atgaagccca gagcaaaaga                                                    20

<210> SEQ ID NO 12
<211> LENGTH: 20
<212> TYPE: DNA
<213> ORGANISM: Artificial Sequence
<220> FEATURE:
<223> OTHER INFORMATION: Primer used in screening assay

<400> SEQUENCE: 12
ggggtgttga aggtctcaaa                                                    20

<210> SEQ ID NO 13
<211> LENGTH: 22
<212> TYPE: DNA
<213> ORGANISM: Artificial Sequence
<220> FEATURE:
<223> OTHER INFORMATION: Primer used in screening assay

<400> SEQUENCE: 13
ggcagccttg tcccttgaag ag                                                 22
```

```
<210> SEQ ID NO 14
<211> LENGTH: 22
<212> TYPE: DNA
<213> ORGANISM: Artificial Sequence
<220> FEATURE:
<223> OTHER INFORMATION: Primer used in screening assay

<400> SEQUENCE: 14
gtagcccacg tcgtagcaaa cc                                                  22

<210> SEQ ID NO 15
<211> LENGTH: 20
<212> TYPE: DNA
<213> ORGANISM: Artificial Sequence
<220> FEATURE:
<223> OTHER INFORMATION: Primer used in screening assay

<400> SEQUENCE: 15
tgacgaggcc cagagcaaga                                                     20

<210> SEQ ID NO 16
<211> LENGTH: 20
<212> TYPE: DNA
<213> ORGANISM: Artificial Sequence
<220> FEATURE:
<223> OTHER INFORMATION: Primer used in screening assay

<400> SEQUENCE: 16
atgggcacag tgtgggtgac                                                     20
```

ENZYME PRODUCING *BACILLUS* STRAINS

CROSS-REFERENCE TO RELATED APPLICATIONS

This application claims priority under 35 U.S.C. §119(e) to U.S. Provisional Patent Application No. 61/526,881 filed Aug. 24, 2011 and U.S. Provisional Patent Application No. 61/527,371 filed Aug. 25, 2011; the entirety of both applications is incorporated by reference herein.

BIBLIOGRAPHY

Complete bibliographic citations of the references referred to herein by the first author's last name in parentheses can be found in the Bibliography section, immediately preceding the claims.

FIELD

The disclosure relates to *Bacillus* strains producing enzymes that provide benefits to animals and methods of using these strains. In one embodiment, the disclosure relates to methods of improving growth performance of an animal. In another embodiment, the disclosure relates to a direct fed microbial, and feed for an animal supplemented with a direct fed microbial. In another embodiment, the disclosure relates to methods for improving manure storage units. In yet another embodiment, the disclosure relates to methods for alleviating an inflammatory response.

SUBMISSION OF SEQUENCE LISTING

The contents of the electronic submission of the text file Sequence Listing, which is named AGP-36010 Sequence Listing.txt, and was created Nov. 13, 2012, and is 3.45 KB in size, is incorporated herein by reference in its entirety.

BACKGROUND

The global swine industry has seen increased feeding of by-products (dried distillers grains with solubles (DDGS), wheat midds, etc.) initially from 0-10% to the current extremes of 30-60%. These diet cost savings have been a great opportunity for industry to save on feed input costs, but come with a set of challenges as well. The fermentation process to extract ethanol from corn removes almost all of the starch, leaving the resulting DDGS feed by-product containing approximately 40% fiber. This higher fiber content relative to corn results in reduced dry matter digestibility and approximately 10 percentage units less digestibility of most amino acids in DDGS compared to corn (Stein and Shurson, 2009).

Consequently the inclusion of DDGS in livestock diets can have negative impacts on animal growth performance and carcass characteristics. In addition to the negative effects on animal growth and carcass quality, alterations in nutrient digestibility as a result of adding DDGS with a high fiber content have implications for swine manure handling, storage, and decomposition. The commercial swine industry has indicated that manure holding capacity is less in anaerobic deep-pit swine manure storage units, and that the manure from pigs fed high level of DDGS has more solids accumulation, as well as ammonia, methane, and hydrogen sulfide gas emissions.

In view of the foregoing, it would be desirable to provide *Bacillus* strains producing enzymes that provide benefits to animals and methods of using these strains.

SUMMARY

The disclosure relates to enzyme producing *Bacillus* strains. In one embodiment, the strains are *Bacillus subtilis*. In another embodiment, the strains are *Bacillus pumilus*.

In at least some embodiments, the *B. subtilis* strain(s) is (are) *Bacillus subtilis* AGTP BS3BP5, *Bacillus subtilis* AGTP BS442, *Bacillus subtilis* AGTP BS521, *Bacillus subtilis* AGTP BS918, *Bacillus subtilis* AGTP BS1013, and *Bacillus subtilis* AGTP BS1069, and *Bacillus subtilis* AGTP 944, and strains having all the characteristics thereof, any derivative or variant thereof, and mixtures thereof. In some embodiments, the *B. pumilus* strain(s) is/are *Bacillus pumilus* AGTP BS1068 and *Bacillus pumilus* KX11-1, and strains having all the characteristics thereof, any derivative or variant thereof, and mixtures thereof.

In one embodiment, the disclosure relates to methods comprising administering an effective amount of enzyme producing strain(s), one or more combination(s) of the strain(s), one or more supernatant(s) from a culture of the strain(s), feed including one or more strain(s) or mixtures thereof to a an animal, wherein the administration improves at least one of the following body weight, average daily gain, average daily feed intake, feed efficiency, carcass characteristics, nutrient digestibility and manure waste problems.

In another embodiment, the enzyme producing strains can be administered to an animal to improve at least one of the breakdown of complex dietary components, manure waste problems, the efficiency of production, carcass characteristics, and performance when feeding high levels of DDGS.

In one embodiment, one or more enzyme producing strain(s) is (are) administered as a direct-fed microbial (DFM). A direct-fed microbial includes one or more *Bacillus* strain(s). The enzyme producing strain(s) is (are) effective at degrading otherwise indigestible feedstuffs such as DDGS. This allows increased nutrient availability, resulting in an improved animal growth response. Additionally, enzyme producing strain(s) abate(s) manure associated odors, thereby improving operational environment air quality. In at least some embodiments, odor reduction is by reducing volatile fatty acids, ammonia, and/or methane and hydrogen sulfide gas production.

In other embodiments, the disclosure relates to a method comprising administering an effective amount of the enzyme producing strain(s), one or more combination(s) of the strain(s), one or more supernatant(s) from a culture of the strain(s), feed including one or more strain(s) or mixtures thereof to a swine in an effective amount to improve the manure storage unit. In certain embodiments, the swine manure storage unit is a manure pit. In at least some embodiments, the administration improves at least one of the following: less incidence of foaming, less accumulation of solids, and less nitrogen, sulfur, phosphorus, fiber-bound nitrogen, total protein, fat, and fiber content when compared to a control manure pit.

In certain embodiments, the enzyme producing strain(s) are directly applied to a manure storage unit, such as a manure pit. Improvements resulting from contacting the enzyme producing strain(s) directly to a manure storage unit include at least one of less incidence of foaming, less accumulation of solids, and less nitrogen, sulfur, phosphorus, fiber-bound nitrogen, total protein, fat, and fiber content than control manure pits.

In another embodiment, the disclosure relates to a method of altering volatile fatty acid composition in a manure pit comprising administering an effective amount of enzyme producing strain(s), one or more combination(s) of the strain(s), one or more supernatant(s) from a culture of the strain(s), feed including one or more strain(s) or mixtures thereof to animals whose manure is stored in the manure pit. In another embodiment, the enzyme producing strains can be contacted directly to the manure pit.

In yet another embodiment, the disclosure relates to a method of altering gas emissions that accumulate in a room housing an animal comprising administering enzyme producing strain(s), one or more combination(s) of the strain(s), one or more supernatant(s) from a culture of the strain(s), feed including one or more strain(s) or mixtures thereof to animals in an effective amount to reduce gas emissions.

In still another embodiment, the disclosure relates to methods for alleviating an inflammatory response comprising administering enzyme producing strain(s), one or more combination(s) of the strain(s), one or more supernatant(s) from a culture of the strain(s), feed including one or more strain(s) or mixtures thereof to animals in an effective amount to alleviate the inflammatory response.

BRIEF DESCRIPTION OF THE DRAWINGS

Exemplary embodiments of the invention are illustrated in the accompanying drawings.

FIG. 1 is a photograph of a gel showing a RAPD PCR profile of *Bacillus subtilis* AGTP BS3BP5.

FIG. 2 is a partial 16S rDNA sequence of *Bacillus subtilis* AGTP BS3BP5.

FIG. 3 is a photograph of a gel showing a RAPD PCR profile of *Bacillus subtilis* AGTP BS442.

FIG. 4 is a partial 16S rDNA sequence of *Bacillus subtilis* AGTP BS442.

FIG. 5 is a photograph of a gel showing a RAPD PCR profile of *Bacillus subtilis* AGTP BS521.

FIG. 6 is a partial 16S rDNA sequence of *Bacillus subtilis* AGTP BS521.

FIG. 7 is a photograph of a gel showing a RAPD PCR profile of *Bacillus subtilis* AGTP BS918.

FIG. 8 is a partial 16S rDNA sequence of *Bacillus subtilis* AGTP BS918.

FIG. 9 is a photograph of a gel showing a RAPD PCR profile of *Bacillus subtilis* AGTP BS1013.

FIG. 10 is a partial 16S rDNA sequence of *Bacillus subtilis* AGTP BS1013.

FIG. 11 is a photograph of a gel showing a RAPD PCR profile of *Bacillus pumilus* AGTP BS1068.

FIG. 12 is a partial 16S rDNA sequence of *Bacillus pumilus* AGTP BS1068.

FIG. 13 is a photograph of a gel showing a RAPD PCR profile of *Bacillus subtilis* AGTP BS1069.

FIG. 14 is a partial 16S rDNA sequence of *Bacillus subtilis* AGTP BS1069.

FIG. 17 is a photograph of a gel showing a RAPD PCR profile of *Bacillus subtilis* AGTP 944.

FIG. 18 is the partial 16S rDNA sequence of *Bacillus subtilis* AGTP 944.

FIG. 21 is the partial 16S rDNA sequence of *Bacillus pumilus* KX11-1.

Figure 15:
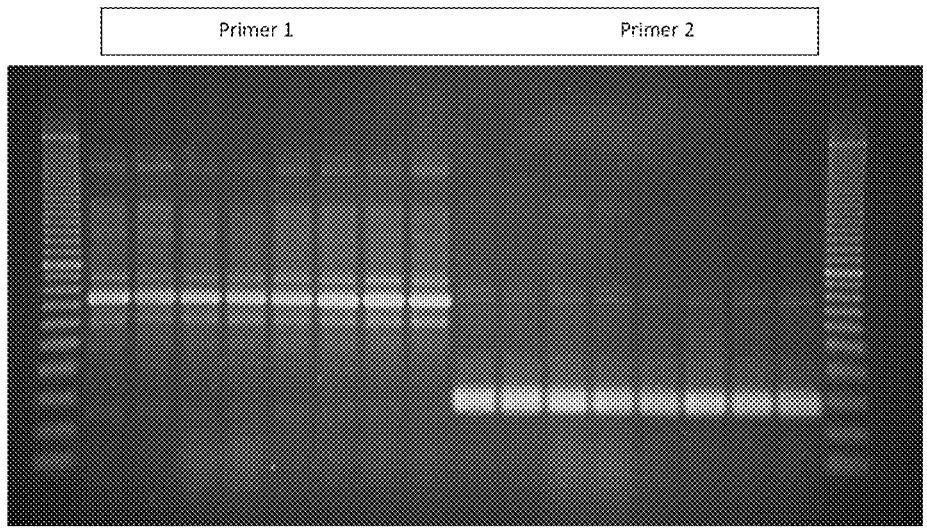
FIG. 15 is a photograph of a gel showing a RAPD PCR profile of *Bacillus subtilis* AGTP 944.
Figure 16:
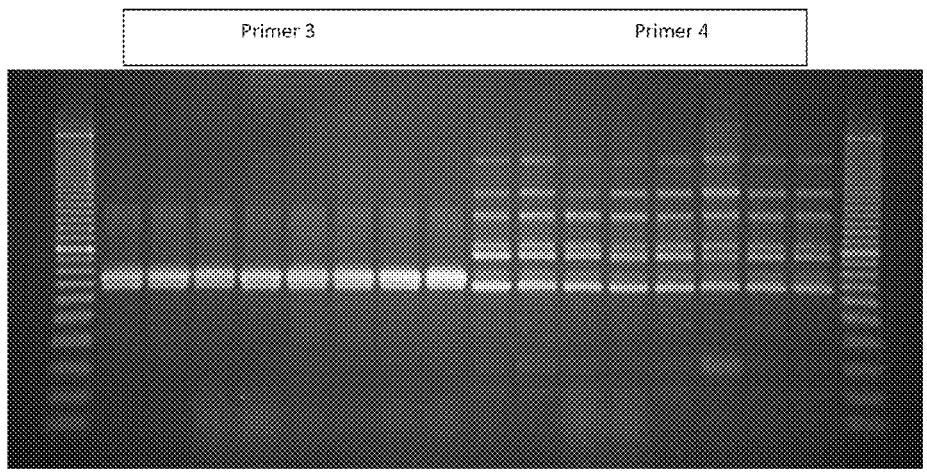
FIG. 16 is a photograph of a gel showing a RAPD PCR profile of *Bacillus subtilis* AGTP 944.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

The organizational framework of this disclosure should not limit any embodiments or elements within the disclosure. It is intended that elements and applications recited within one embodiment, can be applied to other embodiments within the disclosure.

DETAILED DESCRIPTION

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

By "administer," is meant the action of introducing at least one strain and/or supernatant from a culture of at least one strain described herein into the animal's gastrointestinal tract. More particularly, this administration is an administration by oral route. This administration can in particular be carried out by supplementing the feed intended for the animal with the at least one strain, the thus supplemented feed then being ingested by the animal. The administration can also be carried out using a stomach tube or any other way to make it possible to directly introduce the at least one strain into the animal's gastrointestinal tract.

By "at least one strain," is meant a single strain but also mixtures of strains comprising at least two strains of bacteria. By "a mixture of at least two strains," is meant a mixture of two, three, four, five, six or even more strains. In some embodiments of a mixture of strains, the proportions can vary from 1% to 99%. In certain embodiments, the proportion of a strain used in the mixture is at least 5%, 10%, 15%, 20%, 25%, 30%, 35%, 40%, 45%, 50%, 55%, 60%, 65%, 70%, 75%, 80%, 85%, 90%, or 95%. Other embodiments of a mixture of strains are from 25% to 75%. Additional embodiments of a mixture of strains are approximately 50% for each strain. When a mixture comprises more than two strains, the strains can be present in substantially equal proportions in the mixture or in different proportions.

By "contacting," is meant the action of bringing at least one strain and/or supernatant from a culture of at least one strain described herein into close proximity with a substrate, container, or substance, which includes but is not limited to a manure storage unit. In some embodiments, the manure storage unit is a manure pit. Contacting can be through a direct or indirect manner. As used herein, contacting includes applying, spraying, inoculating, dispersing dispensing, pouring, and other like terms.

By "effective amount," is meant a quantity of strain and/or supernatant sufficient to allow improvement in at least one of the following: the efficiency of animal production, carcass characteristics, growth performance of an animal, growth performance when feeding high levels of DDGS to an animal, nutrient digestibility, breakdown of complex dietary components, poultry growth performance, pig growth performance, feed efficiency, average daily gain, average daily feed intake, body weight gain:feed or feed:gain intake, and morality.

In other embodiments, "effective amount" is meant a quantity of strain and/or supernatant sufficient to allow improvement in at least one of the following: manure waste problems, the amount of foaming in a manure storage unit, the microbial ecology of a manure storage unit, the amount of volatile fatty acids in a manure storage unit, the amount of gas production in a room housing animals or a manure storage unit, including but not limited to methane and hydrogen sulfide.

In another embodiment, "effective amount" is meant a quantity of strain and/or supernatant sufficient to allow improvement in at least one of the following: the expression of a gene involved in the inflammatory response, the expression of a protein involved in the inflammatory response, and the activity of a protein involved in the inflammatory response.

As used herein, "performance" refers to the growth of an animal, such as a pig or poultry, measured by one or more of the following parameters: average daily gain (ADG), weight, scours, mortality, feed conversion, which includes both feed: gain and gain:feed, and feed intake. "An improvement in performance" or "improved performance" as used herein, refers to an improvement in at least one of the parameters listed under the performance definition.

As used herein, a "variant" has at least 80% identity of genetic sequences with the disclosed strains using random amplified polymorphic DNA polymerase chain reaction (RAPD-PCR) analysis. The degree of identity of genetic sequences can vary. In some embodiments, the variant has at least 85%, 90%, 95%, 96%, 97%, 98%, or 99% identity of genetic sequences with the disclosed strains using RAPD-PCR analysis. Six primers that can be used for RAPD-PCR analysis include the following: Primer 1 (5'-GGTGCGG-GAA-3') (SEQ ID NO. 1); PRIMER 2 (5'-GTTTCGCTCC-3') (SEQ ID NO. 2); PRIMER 3 (5'-GTAGACCCGT-3') (SEQ ID NO. 3); PRIMER 4 (5'-AAGAGCCCGT-3') (SEQ ID NO. 4); PRIMER 5 (5'-AACGCGCAAC-3') (SEQ ID NO. 5); and PRIMER 6 (5'-CCCGTCAGCA-3') (SEQ ID NO. 6). RAPD analysis can be performed using Ready-to-Go™ RAPD Analysis Beads (Amersham Biosciences, Sweden), which are designed as pre-mixed, pre-dispensed reactions for performing RAPD analysis.

The inventors have found that certain *Bacillus* strains have enzymatic activity(ies) that break down fiber(s), lipid(s), carbohydrate(s), and protein(s). These strain(s) is (are) referred to herein as "enzyme producing strain(s)," "*Bacillus* strain(s)," or "strain(s)." In some embodiments, the enzymatic activity(ies) is (are) cellulase, α-amylase, xylanase, esterase, casein protease, corn starch amylase, β-mannanase, lipase, and/or protease, e.g., zeinase and soy protease.

The inventors have found that certain microorganisms can be used to address the challenging components in dried distillers grains with solubles (DDGS).

The inventors also have found that enzyme producing strains can improve at least one of the following: (1) breakdown of complex dietary components, (2) manure waste problems; (3) the efficiency of animal production; (4) animal carcass characteristics, (5) growth performance an animal; and (6) effects of an inflammatory response.

Enzyme Producing Strains

Enzyme producing strains include *Bacillus* strains, including, but not limited to, *B. subtilis, B. licheniformis, B. pumilus, B. coagulans, B. amyloliquefaciens, B. stearothermophilus, B. brevis, B. alkalophilus, B. clausii, B. halodurans, B. megaterium, B. circulans, B. lautus, B. thuringiensis* and *B. lentus* strains, and strains having all the characteristics thereof, any derivative or variant thereof, and mixtures thereof.

In at least some embodiments, the *B. subtilis* strain(s) is (are) *Bacillus subtilis* AGTP BS3BP5, *Bacillus subtilis* AGTP BS442, *Bacillus subtilis* AGTP BS521, *Bacillus subtilis* AGTP BS918, *Bacillus subtilis* AGTP BS1013, and *Bacillus subtilis* AGTP BS1069, and *Bacillus subtilis* AGTP 944, and strains having all the characteristics thereof, any derivative or variant thereof, and mixtures thereof. In some embodiments, the *B. pumilus* strain(s) is/are *Bacillus pumilus* AGTP BS1068 and *Bacillus pumilus* KX11-1, and strains having all the characteristics thereof, any derivative or variant thereof, and mixtures thereof.

These strains were deposited by Danisco USA, Inc. of Waukesha, Wis. at the Agricultural Research Service Culture Collection (NRRL), 1815 North University Street, Peoria, Ill., 61604. The dates of original deposits and accession numbers are as follows: *Bacillus subtilis* AGTP BS3BP5, May 13, 2011 (NRRL B-50510), *Bacillus subtilis* AGTP BS442, Aug. 4, 2011 (NRRL B-50542), *Bacillus subtilis* AGTP BS521, Aug. 4, 2011 (NRRL B-50545), *Bacillus subtilis* AGTP BS918, May 13, 2011 (NRRL B-50508), *Bacillus subtilis* AGTP BS1013, May 13, 2011 (NRRL B-50509), *Bacillus*

*subtilis* AGTP BS1069, Aug. 4, 2011 (NRRL B-50544), *Bacillus subtilis* AGTP 944, Aug. 11, 2011 (NRRL B-50548), *Bacillus pumilus* AGTP BS1068, Aug. 4, 2011 (NRRL B-50543), and *Bacillus pumilus* KX11-1, Aug. 5, 2011 (NRRL B-50546). All of the deposits were made under the provisions of the Budapest Treaty on the International Recognition of the Deposit of Microorganisms for the Purposes of Patent Procedure.

In some embodiments, the enzyme producing strains have enzymatic activity(ies) including but not limited to cellulase, α-amylase, xylanase, esterase, casein protease, corn starch amylase, β-mannanase, lipase, and/or protease, e.g., zeinase and soy protease.

In at least some embodiments, more than one of the strain(s) described herein is (are) combined.

Any *Bacillus* derivative or variant is also included and is useful in the methods described and claimed herein. In some embodiments, strains having all the characteristics of *Bacillus subtilis* AGTP BS3BP5, *Bacillus subtilis* AGTP BS442, *Bacillus subtilis* AGTP BS521, *Bacillus subtilis* AGTP BS918, *Bacillus subtilis* AGTP BS1013, *Bacillus subtilis* AGTP BS1069, *Bacillus subtilis* AGTP 944, *Bacillus pumilus* AGTP BS1068 and *Bacillus pumilus* KX11-1 are also included and are useful in the methods described and claimed herein.

In certain embodiments, any derivative or variant of *Bacillus subtilis* AGTP BS3BP5, *Bacillus subtilis* AGTP BS442, *Bacillus subtilis* AGTP BS521, *Bacillus subtilis* AGTP BS918, *Bacillus subtilis* AGTP BS1013, *Bacillus subtilis* AGTP BS1069, *Bacillus subtilis* AGTP 944, *Bacillus pumilus* AGTP BS1068, and *Bacillus pumilus* KX11-1 are also included and are useful in the methods described and claimed herein.

In at least some embodiments, the enzyme producing strain(s) is (are) used in combination. In one embodiment, the enzyme producing strains can be used in combination with bacterial strains from the *Bacillus* genus, and other bacterial strains from a different genus.

In at least some embodiments, the enzyme producing strain(s) and methods provided herein improve one or more of the following: the breakdown of complex dietary components, manure waste problems, the efficiency of production, carcass characteristics, and performance when feeding high levels of DDGS when compared to a control.

Manure waste problems include, but are not limited to, undesirable manure nutrient and microbial composition, and undesirable gas emissions from the manure storage units, such as manure pits. An improvement in manure waste problems include, but are not limited to, at least one of (1) less nutrients accumulated in the manure, (2) shift manure microbial communities to favorable populations for solids breakdown, and (3) a decrease in ammonia, methane, and hydrogen sulfide gas emissions.

An improvement in carcass characteristics can be measured by at least one of increased percent lean yield and dressing percentage, and decreased fat iodine values. Performance can be measured by average daily gain, average daily feed intake, and feed required per unit of gain, and other measurements known in the art.

When ingested, the enzyme producing strain(s) produce(s) enzymes. In some embodiments, the enzyme producing strain(s) produce(s) enzymes in vivo. In other embodiments, the enzyme producing strain(s) survive(s) in the manure of animals to which the strain are administered and produce(s) enzymes in the excreted manure.

Methods of Culturing a Strain

*Bacillus* strains are produced by fermentation of the bacterial strains. Fermentation can be started by scaling-up a seed culture. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth. A non-limiting exemplary medium is TSB. After the inoculum is added to the fermentation vessel, the temperature and agitation are controlled to allow maximum growth. Once the culture reaches a maximum population density, the culture is harvested by separating the cells from the fermentation medium. This is commonly done by centrifugation.

The count of the culture can then be determined. CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

In one embodiment, each *Bacillus* strain is fermented between a $5\times10^8$ CFU/ml level to about a $4\times10^9$ CFU/ml level. In at least one embodiment, a level of $2\times10^9$ CFU/ml is used. The bacteria are harvested by centrifugation, and the supernatant is removed. The supernatant can be used in the methods described herein. In at least some embodiments, the bacteria are pelleted. In at least some embodiments, the bacteria are freeze-dried. In at least some embodiments, the bacteria are mixed with a carrier. However, it is not necessary to freeze-dry the *Bacillus* before using them. The strains can also be used with or without preservatives, and in concentrated, unconcentrated, or diluted form.

DFMs and Methods of Preparing a DFM

A composition including one or more strain(s) described herein is provided. The composition can be fed to an animal as a direct-fed microbial (DFM). One or more carrier(s) or other ingredients can be added to the DFM. The DFM may be presented in various physical forms, for example, as a top dress, as a water soluble concentrate for use as a liquid drench or to be added to a milk replacer, gelatin capsule, or gels. In one embodiment of the top dress form, freeze-dried bacteria fermentation product is added to a carrier, such as whey, maltodextrin, sucrose, dextrose, limestone (calcium carbonate), rice hulls, yeast culture, dried starch, and/or sodium silico aluminate. In one embodiment of the water soluble concentrate for a liquid drench or milk replacer supplement, freeze-dried bacteria fermentation product is added to a water soluble carrier, such as whey, maltodextrin, sucrose, dextrose, dried starch, sodium silico aluminate, and a liquid is added to form the drench or the supplement is added to milk or a milk replacer. In one embodiment of the gelatin capsule form, freeze-dried bacteria fermentation product is added to a carrier, such as whey, maltodextrin, sugar, limestone (calcium carbonate), rice hulls, yeast culture dried starch, and/or sodium silico aluminate. In one embodiment, the bacteria and carrier are enclosed in a degradable gelatin capsule. In one embodiment of the gels form, freeze-dried bacteria fermentation product is added to a carrier, such as vegetable oil, sucrose, silicon dioxide, polysorbate 80, propylene glycol, butylated hydroxyanisole, citric acid, ethoxyquin, and/or artificial coloring to form the gel.

The strain(s) may optionally be admixed with a dry formulation of additives including but not limited to growth substrates, enzymes, sugars, carbohydrates, extracts and growth promoting micro-ingredients. The sugars could include the following: lactose; maltose; dextrose; malto-dextrin; glucose; fructose; mannose; tagatose; sorbose; raffinose; and galactose. The sugars range from 50-95%, either individually or in combination. The extracts could include yeast or dried yeast fermentation solubles ranging from 5-50%. The growth substrates could include: trypticase, ranging from 5-25%; sodium lactate, ranging from 5-30%; and, Tween 80, ranging from 1-5%. The carbohydrates could include mannitol, sorbitol, adonitol and arabitol. The carbohydrates range from 5-50% individually or in combination. The micro-ingredients could include the following: calcium carbonate, ranging from 0.5-5.0%; calcium chloride, ranging from 0.5-5.0%; dipotassium phosphate, ranging from 0.5-5.0%; calcium phosphate, ranging from 0.5-5.0%; manganese proteinate, ranging from 0.25-1.00%; and, manganese, ranging from 0.25-1.0%.

To prepare DFMs described herein, the culture(s) and carrier(s) (where used) can be added to a ribbon or paddle mixer and mixed for about 15 minutes, although the timing can be increased or decreased. The components are blended such that a uniform mixture of the cultures and carriers result. The final product is preferably a dry, flowable powder. The strain(s) can then be added to animal feed or a feed premix, added to an animal's water, or administered in other ways known in the art. A feed for an animal can be supplemented with one or more strain(s) described herein or with a composition described herein.

The DFM provided herein can be administered, for example, as the strain-containing culture solution, the strain-producing supernatant, or the bacterial product of a culture solution.

Administration of a DFM provided herein to an animal can increase the performance of the animal. In one embodiment, administration of a DFM provided herein to an animal can increase the average daily feed intake (ADFI), average daily gain (ADG), or feed efficiency (gain:feed; G:F or feed:gain; F:G) (collectively, "performance metrics"). One or more than one of these performance metrics may be improved.

The DFM may be administered to the animal in one of many ways. For example, the strain(s) can be administered in a solid form as a veterinary pharmaceutical, may be distributed in an excipient, preferably water, and directly fed to the animal, may be physically mixed with feed material in a dry form, or the strain(s) may be formed into a solution and thereafter sprayed onto feed material. The method of administration of the strain(s) to the animal is considered to be within the skill of the artisan.

Methods of Administering to an Animal

In one embodiment, the strains can be administered in an effective amount to animals. In at least some embodiments, the disclosure relates to a method comprising administering to an animal an effective amount of the enzyme producing strain(s), one or more combination(s) of the strain(s), one or more supernatant(s) from a culture of the strain(s), or feed including one or more strain(s) or mixtures thereof. In one embodiment, the animal is a pig. In another embodiment, the animal is poultry. In yet another embodiment, the animal is a ruminant.

Administration of one or more enzyme producing strain(s) to animals is accomplished by any convenient method, including adding the strains to the animals' drinking water, to their feed, or to the bedding, or by direct oral insertion, such as by an aerosol or by injection.

In another embodiment, administration of one or more enzyme producing strains is by spraying the animal with the enzyme producing strains. The animal can clean or preen and ingest the enzyme producing strains.

In one embodiment, the *Bacillus* strains are administered as spores.

As used herein, the term "animal" includes but is not limited to human, mammal, amphibian, bird, reptile, swine, pigs, cows, cattle, goats, horses, sheep, poultry, and other animals kept or raised on a farm or ranch, sheep, big-horn sheep, buffalo, antelope, oxen, donkey, mule, deer, elk, caribou, water buffalo, camel, llama, alpaca, rabbit, mouse, rat, guinea pig, hamster, ferret, dog, cat, and other pets, primate, monkey, ape, and gorilla.

In some embodiments, the animals are birds of different ages, such as starters, growers and finishers. In certain embodiments, the animals are poultry and exotic fowl, including, but not limited to, chicks, turkey poults, goslings, ducklings, guinea keets, pullets, hens, roosters (also known as cocks), cockerels, and capons.

In some embodiments, the animals are pigs, including, but not limited to, nursery pigs, breeding stock, sows, gilts, boars, lactation-phase piglets, and finishing pigs. The strain(s) can be fed to a sow during the lactation period, although the strain(s) can be fed for different durations and at different times. In certain embodiments, the strain(s) is(are) administered to piglets by feeding the strain(s) to a gilt or sow. It is believed that the transfer to the piglets from the sow is accomplished via the fecal-oral route and/or via other routes.

The enzyme producing strains can be administered to an animal to improve at least one of nutrient digestibility, swine growth performances, poultry growth performance responses, feed efficiency (gain:feed or feed:gain), body weight, feed intake, average daily gain, average daily feed intake, the breakdown of complex dietary components, the efficiency of poultry production, the efficiency of swine production, and mortality. These benefits can be particularly useful when diets containing high levels of DDGS are fed. Initially, DDGS was from 0% to 10% of the animal's diet. Currently, DGGS is from 30% to 60%.

The amount of improvement can be measured as described herein or by other methods known in the art. These effective amounts can be administered to the animal by providing ad libitum access to feed containing the DFM. The DFM can also be administered in one or more doses.

In certain embodiments, the improvement is by at least 1-5%, 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, 85-90%, 90-95%, 96%, 97%, 98%, 99%, or greater than 99% as compared to an untreated control.

In at least some embodiments, the improvement in these measurements in an animal to which the strain(s) is/are administered is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98, 99%, and greater than 99% compared to a control animal.

In other embodiments, the improvement in these measurements in an animal to which the strain(s) is/are administered is 2-8% compared to a control animal. In certain other embodiments, the improvement in these measurements in an animal to which the strain(s) is/are administered is at least 8% compared to a control animal.

In some embodiments, a control animal is an animal that has not been administered the enzyme producing strains.

This effective amount can be administered to the animal in one or more doses. In some embodiments, the one or more *Bacillus* strain(s) is(are) added to an animal's feed at a rate of at least $1 \times 10^4$ CFU/animal/day.

In one embodiment, the administration improves at least one of nutrient digestibility, growth performance responses, e.g., feed efficiency, the breakdown of complex dietary components, the efficiency of production, body weight gain, feed intake, and mortality.

In certain embodiments of the method, the strain(s) is/are administered at about $1 \times 10^5$ CFU/animal/day to about $1 \times 10^{11}$ CFU/animal/day. In some embodiments, the animal is a swine. In another embodiment, the animal is poultry.

In at least some embodiments, the method is used when the animal is fed high levels of dried distillers grains with solubles (DDGS). The high levels of DDGS can be a rate of over 10% of the animal's diet. The high levels of DDGS can also be a rate of over 30% of the animal's diet.

In at least some embodiments, the effective amount of at least one strain of bacterium is administered to an animal by supplementing a feed intended for the animal with the effective amount of at least one strain of bacterium. As used herein, "supplementing," means the action of incorporating the effective amount of bacteria provided herein directly into the feed intended for the animal. Thus, the animal, when feeding, ingests the bacteria provided herein.

The enzyme producing strains can be administered as a single strain or as multiple strains. Supernatant of one or more enzyme producing strains can be administered to an animal. When ingested, the enzyme producing strains produce enzymes.

In certain embodiments, one or more enzyme producing strain(s) is (are) fed to swine. The one or more enzyme producing strain(s) address(es) the challenging components in dried distillers grains with solubles (DDGS).

In one embodiment, the enzyme producing strain(s) is(are) added to animal feed at a rate of $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$ and greater than $1 \times 10^{13}$ CFU per gram of animal feed.

In another embodiment, the enzyme producing strain(s) is(are) added to animal feed at a rate of $1 \times 10^3$, $1 \times 10^4$, $1 \times 10^5$, $1 \times 10^6$, $1 \times 10^7$, $1 \times 10^8$, $1 \times 10^9$, $1 \times 10^{19}$, $1 \times 10^{11}$, $1 \times 10^{12}$, $1 \times 10^{13}$ and greater than $1 \times 10^{13}$ CFU per animal per day.

In one embodiment, the one or more *Bacillus* strain(s) is(are) added to pigs' feed at a rate of about $3.75 \times 10^5$ CFU per gram of feed. It(they) can also be fed at about $1 \times 10^4$ to about $1 \times 10^{11}$ CFU/animal/day. In some embodiments, the one or more *Bacillus* strain(s) is(are) fed at about $1 \times 10^8$ CFU/animal/day.

For ruminants, the one or more *Bacillus* strain(s) is(are) fed at about $5 \times 10^9$ CFU/hd/day.

For poultry, the one or more *Bacillus* strain(s) is(are) added to feed at about $1 \times 10^4$ CFU/g feed to about $1 \times 10^{10}$ CFU/g feed. In at least some embodiments, the one or more *Bacillus* strain(s) is fed at about $1 \times 10^5$ CFU/bird/day to about $1 \times 10^8$ CFU/bird/day.

Feed Material

In another embodiment, a feed for an animal comprises at least one strain of bacterium described herein. In at least some embodiments, feed is supplemented with an effective amount of at least one strain of bacterium. As used herein, "supplementing," means the action of incorporating the effective amount of bacteria provided herein directly into the feed intended for the animal. Thus, the animal, when feeding, ingests the bacteria provided herein.

When used in combination with a feed material, for monogastric diets, the feed material can include corn, soybean meal, byproducts like distillers dried grains with solubles (DDGS), and vitamin/mineral supplement. The feed material for ruminants can be grain or hay or silage or grass, or combinations thereof. Included amongst such feed materials are corn, dried grain, alfalfa, any feed ingredients and food or feed industry by-products as well as bio fuel industry by-products and corn meal and mixtures thereof. Other feed materials can also be used.

The time of administration can vary so long as an improvement is shown in one or more of the following: (1) breakdown of complex dietary components, (2) nutrient digestibility, (3) manure waste problems, (4) the efficiency of production, (5) carcass characteristics, (6) growth performance, (7) growth performance when feeding high levels of DDGS, (8) poultry growth performance responses, (9) swine growth performance responses, (10) the efficiency of poultry production, (11) the efficiency of swine production, (12) body weight gain, (13) feed intake, (14) feed efficiency, and (15) mortality. Administration is possible at any time with or without feed. However, the bacterium is preferably administered with or immediately before feed.

Methods for Improving Growth Performance of an Animal

In one embodiment, the disclosure relates to a method for improving growth performance of an animal comprising using one or more enzyme producing strains or supernatants therefrom to improve the growth performance of the animal relative to an animal that has not been administered the enzyme producing strains. In one embodiment, the animal is a pig. In another embodiment, the animal is poultry. In another embodiment, the animal is a ruminant.

In one embodiment, growth performance includes but is not limited to nutrient digestibility, poultry growth performance responses, pig growth performance responses, feed efficiency, the breakdown of complex dietary components, average daily gain, averaging daily feed intake, body weight gain, feed intake, carcass characteristics and mortality. In yet another embodiment, the methods disclosed herein are used to improve the growth performance of an animal fed an animal feed comprising DDGS.

In certain embodiments, the improvement in growth performance is by at least 1-5%, 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, 85-90%, 90-95%, 96%, 97%, 98%, 99%, or greater than 99% as compared to an untreated control.

In at least some embodiments, the improvement in growth performance of an animal to which the strain(s) is/are administered is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98, 99%, and greater than 99% compared to a control animal.

In one embodiment, the enzyme producing strains for improving growth performance of an animal comprise a *Bacillus* strain. In one embodiment, the *Bacillus* strain is *Bacillus subtilis*. In another embodiment, the *Bacillus* strain is *Bacillus pumilus*.

In another embodiment, the enzyme producing strains for improving growth performance include but are not limited to

*Bacillus subtilis* AGTP BS3BP5, *Bacillus subtilis* AGTP BS442, *Bacillus subtilis* AGTP BS521, *Bacillus subtilis* AGTP BS918, *Bacillus subtilis* AGTP BS1013, and *Bacillus subtilis* AGTP BS1069, *Bacillus subtilis* AGTP 944, *Bacillus pumilus* AGTP BS1068 and *Bacillus pumilus* KX11-1, and strains having all the characteristics thereof, any derivative or variant thereof, and mixtures thereof.

The enzyme producing strain(s) for improving growth performance of an animal may be administered as a single strain, one or more combination(s) of the strain(s), one or more supernatant(s) from a culture of the strain(s), feed including one or more strain(s) or mixtures thereof.

A. Nutrient Digestibility

In yet another embodiment, the disclosure relates to a method of increasing digestibility of an animal feed comprising administering an enzyme producing strain to an animal in an amount effective to increase the digestibility of an animal feed as compared to an animal not administered the enzyme producing strain. In another embodiment, the method further comprises measuring the amount of nutrients accumulated in a manure pit from the animal administered the enzyme producing strain and comparing these amount of nutrients to the amount of nutrients in a manure pit from an animal not administered the enzyme-producing strain. In yet another embodiment, the animal feed comprises DDGS.

In yet another embodiment, the disclosure relates to a method of increasing digestibility of an animal feed comprising administering an animal a feed supplemented with an enzyme producing strain in an amount effective to increase the digestibility of the animal feed as compared to an animal not administered the enzyme producing strain.

In one embodiment, methods for improving growth performance of an animal comprise administering an enzyme producing strain to an animal, and reducing the amount of undigested nutrients by the animal as compared to an animal that was not administered the enzyme producing strain.

In another embodiment, methods for improving growth performance of an animal comprise reducing the amount of undigested nutrients by an animal by administering an enzyme producing strain to the animal as compared to an animal that was not administered the enzyme producing strain.

In another embodiment, methods for improving growth performance of an animal comprise administering an enzyme producing strain to an animal, measuring the amount of nutrients accumulated in a manure pit from the animal administered the enzyme producing strain, and comparing the amount of nutrients in the manure pit from an animal administered the enzyme producing strains to the amount of nutrients in a second manure pit from an animal not administered the enzyme-producing strain.

In one embodiment, digestibility of an animal feed can be measured by the amount of nutrients in a manure pit. Any nutrient can be measured from the manure pit including but not limited to dry matter, ash, total nitrogen, ammonium nitrogen, phosphorous and calcium.

The enzyme producing strain(s) for improving nutrient digestibility may be administered as a single strain, one or more combination(s) of the strain(s), one or more supernatant(s) from a culture of the strain(s), feed including one or more strain(s) or mixtures thereof.

B. Poultry Growth Performance

In one embodiment, the disclosure relates to a method of increasing poultry growth performance comprising administering an enzyme producing strain to poultry in an amount effective to increase the growth performance of the poultry as compared to poultry not administered the enzyme producing strain. The methods disclosed herein can be used to improve growth performance regardless of the feed or the diet of the poultry.

In one embodiment, the disclosure relates to a method of increasing growth performance in poultry fed a high fibrous by-product diet comprising administering an enzyme producing strain to a poultry, which are fed a high fibrous by-product diet, in an amount effective to increase the growth performance of the poultry as compared to poultry not administered the enzyme producing strain.

In another embodiment, the disclosure relates to a method of increasing the average daily gain in poultry comprising administering an enzyme producing strain to poultry in an amount effective to increase the average daily gain of the poultry as compared to poultry not administered the enzyme producing strain.

In another embodiment, the disclosure relates to a method of increasing the average daily feed intake in poultry comprising administering an enzyme producing strain to poultry in an amount effective to increase the average daily feed intake as compared to poultry not administered the enzyme producing strain.

In another embodiment, the disclosure relates to a method of improving feed efficiency of an animal feed in poultry comprising administering to poultry an animal feed supplemented with an enzyme producing strain in an amount effective to increase the feed efficiency in poultry as compared to poultry not administered the enzyme producing strain.

In yet another embodiment, the disclosure relates to a method of improving carcass characteristics comprising administering an enzyme producing strain to poultry in an amount effective to improve the carcass characteristics of the poultry as compared to poultry not administered the enzyme producing strain. Carcass characteristics that can be improved include but are not limited to fat depth, organ weights, breast characteristics, dressed weight, carcass grade, and carcass value.

In one embodiment, the measured value of the carcass characteristics may be increased or decreased.

In yet another embodiment, the measured value of one or more of the following carcass characteristics is increased: fat depth, organ weights, breast characteristics, dressed weight, carcass grade, and carcass value.

In still another embodiment, the measured value of one or more of the following carcass characteristics is decreased: fat depth, organ weights, breast characteristics, dressed weight, carcass grade, and carcass value.

In still another embodiment, the disclosure relates to a method of reducing mortality in poultry comprising administering an enzyme producing strain to poultry in an amount effective to reduce mortality of said poultry as compared to poultry not administered the enzyme producing strain.

In another embodiment, the disclosure relates to a method of improving lignin digestibility comprising administering an enzyme producing strain to poultry in an amount effective to improve lignin digestibility as compared to poultry not administered the enzyme producing strain.

In another embodiment, the disclosure relates to a method of improving lignin digestibility in high fibrous diets comprising administering an enzyme producing strain to poultry in an amount effective to improve lignin digestibility of the high fibrous diets as compared to poultry not administered the enzyme producing strain. In another embodiment, the high fibrous diets comprise by-product based diets. In yet another embodiment, the diet comprises DDGS.

In another embodiment, the disclosure relates to a method of improving apparent ileal digestibility comprising administering an enzyme producing strain to poultry in an amount effective to improve apparent ileal digestibility as compared to poultry not administered the enzyme producing strain.

In yet another embodiment, the disclosure relates to a method of improving apparent total tract digestibility comprising administering an enzyme producing strain to poultry in an amount effective to improve apparent total tract digestibility as compared to poultry not administered the enzyme producing strain.

In still another embodiment, the disclosure relates to a method of lowering the pH of ileal digesta comprising administering an enzyme producing strain to poultry in an amount effective to lower the pH of ileal digesta as compared to poultry not administered the enzyme producing strain.

In still another embodiment, the methods recited above further comprise administering a feed supplemented with an enzyme producing strain.

The enzyme producing strain(s) for improving poultry growth performance may be administered as a single strain, one or more combination(s) of the strain(s), one or more supernatant(s) from a culture of the strain(s), feed including one or more strain(s) or mixtures thereof.

C. Pig Growth Performance

In one embodiment, the disclosure relates to a method of increasing growth performance of a pig comprising administering an enzyme producing strain to a pig in an amount effective to increase the growth performance of the pig as compared to a pig not administered the enzyme producing strain. The methods disclosed herein can be used to improve growth performance regardless of the feed or the diet of the pig.

In one embodiment, the disclosure relates to a method of increasing growth performance in a pig fed a high fibrous by-product diet comprising administering an enzyme producing strain to a pig, which is fed a high fibrous by-product diet, in an amount effective to increase the growth performance of the pig as compared to a pig not administered the enzyme producing strain.

In another embodiment, the disclosure relates to a method of increasing the average daily gain in a pig comprising administering an enzyme producing strain to a pig in an amount effective to increase the average daily gain of the pig as compared to a pig not administered the enzyme producing strain.

In another embodiment, the disclosure relates to a method of increasing the average daily feed intake in a pig comprising administering an enzyme producing strain to a pig in an amount effective to increase the average daily feed intake as compared to a pig not administered the enzyme producing strain.

In another embodiment, the disclosure relates to a method of improving feed efficiency of animal feed in a pig comprising administering to a pig an animal feed supplemented with an enzyme producing strain in an amount effective to increase the feed efficiency in the pig as compared to a pig not administered the enzyme producing strain.

In yet another embodiment, the disclosure relates to a method of improving carcass characteristics of a pig comprising administering an enzyme producing strain to a pig in an amount effective to improve the carcass characteristics of the pig as compared to a pig not administered the enzyme producing strain. Carcass characteristics that can be improved include but are not limited to fat depth, loin depth; percent lean meat; hot carcass weight, organ weights, carcass grade, and carcass value.

In one embodiment, the measured value of the carcass characteristics may be increased or decreased.

In yet another embodiment, the measured value of one or more of the following carcass characteristics is increased: fat depth, loin depth; percent lean meat; hot carcass weight, organ weights, carcass grade, and carcass value.

In still another embodiment, the measured value of one or more of the following carcass characteristics is decreased: fat depth, loin depth; percent lean meat; hot carcass weight, organ weights, carcass grade, and carcass value.

In still another embodiment, the disclosure relates to a method of reducing mortality rate in pigs comprising administering an enzyme producing strain to pigs in an amount effective to reduce mortality of said pigs as compared to pigs not administered the enzyme producing strain.

In another embodiment, the disclosure relates to a method of improving lignin digestibility comprising administering an enzyme producing strain to a pig in an amount effective to improve lignin digestibility as compared to a pig not administered the enzyme producing strain.

In another embodiment, the disclosure relates to a method of improving lignin digestibility in high fibrous diets comprising administering an enzyme producing strain to a pig in an amount effective to improve lignin digestibility of the high fibrous diets as compared to a pig not administered the enzyme producing strain. In another embodiment, the high fibrous diets comprise by-product based diets. In yet another embodiment, the diet comprises DDGS.

In another embodiment, the disclosure relates to a method of improving apparent ileal digestibility comprising administering an enzyme producing strain to a pig in an amount effective to improve apparent ileal digestibility in the pig as compared to a pig not administered the enzyme producing strain.

In yet another embodiment, the disclosure relates to a method of improving apparent total tract digestibility comprising administering an enzyme producing strain to a pig in an amount effective to improve apparent total tract digestibility in the pig as compared to a pig not administered the enzyme producing strain.

In still another embodiment, the disclosure relates to a method of lowering the pH of ileal digesta comprising administering an enzyme producing strain to a pig in an amount effective to lower the pH of ileal digesta in the pig as compared to a pig not administered the enzyme producing strain.

In still another embodiment, the methods recited above further comprise administering a feed supplemented with an enzyme producing strain.

In another embodiment, the enzyme producing strains in the methods recited above related to pig growth performance is a composition comprising *Bacillus subtilis* strains AGTP BS918 (NRRL B-50508), AGTP BS1013 (NRRL B-50509) and AGTP BS3BP5 (NRRL B-50510).

The enzyme producing strain(s) for improving pig growth performance may be administered as a single strain, one or more combination(s) of the strain(s), one or more supernatant(s) from a culture of the strain(s), feed including one or more strain(s) or mixtures thereof.

Methods for Improving Manure Storage Units

In one embodiment, the disclosure relates to a method for improving manure storage units comprising administering enzyme producing strain(s), one or more combination(s) of the strain(s), one or more supernatant(s) from a culture of the strain(s), feed including one or more strain(s) or mixtures thereof an animal in an effective amount to improve the manure storage unit. In one embodiment, the animal is a pig. In certain embodiments, the manure storage unit is a manure pit.

In still another embodiment, the disclosure relates to a method for improving air quality in a room housing an animal comprising administering enzyme producing strain(s), one or more combination(s) of the strain(s), one or more supernatant(s) from a culture of the strain(s), feed including one or more strain(s) or mixtures thereof to an animal in an effective amount to improve the air quality in the room. In one embodiment, improving air quality comprises abating odors in the room. In another embodiment, improving air quality comprises reducing production of one or more of the following: volatile fatty acids, ammonia, methane, or hydrogen sulfide.

In at least some embodiments, the administration improves at least one of the following: less incidence of foaming, less accumulation of solids, and less nitrogen, sulfur, phosphorus, fiber-bound nitrogen, total protein, fat, and fiber content when compared to a control manure pit.

In one embodiment, the enzyme producing strains for improving manure storage units comprise a *Bacillus* strain. In one embodiment, the *Bacillus* strain is *Bacillus subtilis*. In another embodiment, the *Bacillus* strain is *Bacillus pumilus*.

In another embodiment, the enzyme producing strains for improving a manure storage unit include but are not limited to *Bacillus subtilis* AGTP BS3BP5, *Bacillus subtilis* AGTP BS442, *Bacillus subtilis* AGTP BS521, *Bacillus subtilis* AGTP BS918, *Bacillus subtilis* AGTP BS1013, and *Bacillus subtilis* AGTP BS1069, *Bacillus subtilis* AGTP 944, *Bacillus pumilus* AGTP BS1068 and *Bacillus pumilus* KX11-1, and strains having all the characteristics thereof, any derivative or variant thereof, and mixtures thereof.

In another embodiment, the disclosure relates to a method for improving a manure storage unit comprising contacting enzyme producing strain(s), one or more combination(s) of the strain(s), one or more supernatant(s) from a culture of the strain(s), compositions including one or more strain(s) or mixtures thereof directly to a manure storage unit, such as a manure pit. Improvements resulting from contacting the enzyme producing strain(s) directly to a manure storage unit include at least one of less incidence of foaming, less accumulation of solids, and less nitrogen, sulfur, phosphorus, fiber-bound nitrogen, total protein, fat, and fiber content than control manure pits.

In another embodiment, the methods described above can be used to improve manure waste problems, which include but are not limited to foaming in the manure pit, accumulation of solids, increases in (a) nitrogen, (b) sulfur, (c) phosphorus, (d) fiber-bound nitrogen, (e) total protein, (f) fat, and (g) fiber content.

A. Methods for Controlling or Reducing Foam in a Manure Storage Unit

In another embodiment, the disclosure relates to a method for controlling or reducing foam in a manure storage unit comprising administering an effective amount of enzyme producing strain(s), one or more combination(s) of the strain(s), one or more supernatant(s) from a culture of the strain(s), feed including one or more strain(s) or mixtures thereof to an animal in an effective amount to control or reduce the amount of foam in a manure storage unit as compared to a manure storage unit where animals were not administered the enzyme producing strains. In yet another embodiment, the foam:liquid ratio of the manure storage unit is reduced.

In another embodiment, the disclosure relates to a method for controlling or reducing foam in a storage pit comprising contacting enzyme producing strain(s), one or more combination(s) of the strain(s), one or more supernatant(s) from a culture of the strain(s), compositions including one or more strain(s) or mixtures thereof directly to a manure storage pit in an effective amount to control reduce the foam in a manure storage pit as compared to a manure storage pit without the enzyme producing strains. In another embodiment, the foam: liquid ratio of the manure storage unit is reduced.

The amount of foam in a manure storage unit is associated with the amount of solids in the manure storage unit. Manure storage units with a higher percentage of solids generally have greater foam:liquid ratio, and hence more foam.

In another embodiment, the disclosure relates to a method for controlling or reducing foam in a manure storage unit comprising administering an effective amount of enzyme producing strain(s), one or more combination(s) of the strain(s), one or more supernatant(s) from a culture of the strain(s), feed including one or more strain(s) or mixtures thereof to an animal in an effective amount to reduce the amount of solids, and thereby reduce the amount of foam, in a manure storage unit as compared to a manure storage unit where animals were not administered the enzyme producing strains. In yet another embodiment, the foam:liquid ratio of the manure storage unit is reduced.

In another embodiment, the disclosure relates to a method for controlling or reducing foam in a manure storage unit comprising contacting enzyme producing strain(s), one or more combination(s) of the strain(s), one or more supernatant(s) from a culture of the strain(s), compositions including one or more strain(s) or mixtures thereof directly to a manure storage unit in an effective amount to reduce the amount of solids in the manure storage unit as compared to a manure storage unit without the enzyme producing strains. In another embodiment, the foam:liquid ratio of the manure storage unit is reduced.

B. Methods for Altering a Microbial Ecology in a Manure Storage Unit

In one embodiment, the disclosure relates to a method for altering a microbial ecology in a manure storage unit comprising administering enzyme producing strain(s), one or more combination(s) of the strain(s), one or more supernatant(s) from a culture of the strain(s), feed including one or more strain(s) or mixtures thereof to a an animal in an effective amount to alter the microbial ecology in the manure storage unit as compared to a manure storage unit where animals were not administered the enzyme producing strains.

In another embodiment, the disclosure relates to a method for altering a microbial ecology in a manure storage unit comprising contacting enzyme producing strain(s), one or more combination(s) of the strain(s), one or more supernatant(s) from a culture of the strain(s), compositions including one or more strain(s) or mixtures thereof directly to the manure storage unit in an effective amount to alter the microbial ecology in the manure storage unit as compared to a manure storage unit where the enzyme producing strains were not used.

In one embodiment, enzyme producing strains can alter, either directly or indirectly, the microbial ecology in a manure storage unit and cause an increase in the population of certain bacterial species and a decrease in the population of other bacterial species. Bacterial species that can be altered, either directly or indirectly, by the enzyme producing strains include but are not limited to methanogens, *bacteroides, Clostridium* cluster I, *clostridium* cluster IV, *clostridium* cluster XIVa, and sulfate reducing bacteria.

In one embodiment, the enzyme producing strains have the ability to shift nutrient utilization by the microbial population and subsequently alter the microbial ecology such that aggregated foaming incidents are alleviated, either by lessening gas production available to be trapped in the foam matrix, altering the availability of molecular compounds making up the foam matrix, or directly inhibiting the growth of bacteria associated with foaming incidents.

C. Methods of Altering Volatile Fatty Acid Composition

In one embodiment, the disclosure relates to a method for altering volatile fatty acid composition in manure comprising administering an enzyme producing strain to an animal in an effective amount to alter fatty acid composition in manure from said animal as compared to manure from a second animal not administered an enzyme producing strain. In one embodiment, altering fatty acid composition may result in an increase in certain fatty acids and a decrease in other fatty acids. In another embodiment, altering fatty acid compositions may occur in a direct or indirect manner.

In one embodiment, the disclosure relates to a method for altering volatile fatty acid composition in a manure storage unit comprising administering an enzyme producing strain to an animal in an effective amount to alter the fatty acid composition in manure from said animal that is stored in said manure storage unit as compared manure from a second animal not administered an enzyme producing strain. In one embodiment, the animal is a pig. In another embodiment, the manure storage unit is a manure pit.

In still another embodiment, the disclosure relates to a method for altering volatile fatty acid composition in a manure storage unit comprising administering an enzyme producing strain to an animal; measuring the amount of volatile fatty acid in manure from the animal fed the enzyme producing strains; and adjusting the concentration of enzyme producing strain fed to the animal to achieve a desired volatile fatty acid concentration in the manure stored in the manure pit.

In yet another embodiment, the disclosure relates to a method for altering volatile fatty acid composition in a manure storage unit comprising contacting an enzyme producing strain directly to the manure storage unit in an effective amount to alter fatty acid composition in the manure storage unit as compared to a manure storage unit without an enzyme producing strain.

In another embodiment, the volatile fatty acids that can be altered by the methods disclosed herein include but are not limited to acetate, propionate, butyrate, 1-butyrate, 4-methyl-valerate. In another embodiment, methods disclosed herein increase the fatty acid butyrate in the manure. In still another embodiment, the methods disclosed herein decrease the fatty acid 4-methyl-valerte in the manure.

In another embodiment, total volatile fatty acids can be altered. In another embodiment, methods disclosed herein reduce total volatile fatty acids in the manure.

Methods for Altering Gas Emissions

In one embodiment, the disclosure relates to a method for altering gas emissions comprising administering an enzyme producing strain to an animal in an effective amount to alter gas emissions as compared to an animal not administered an enzyme producing strain. In one embodiment, altering gas emissions may result in an increase in certain gas emissions and a decrease in other gas emissions. In another embodiment, altering gas emissions may occur in a direct or indirect manner.

In one embodiment, the enzyme producing strains for altering gas emissions comprise a *Bacillus* strain. In one embodiment, the *Bacillus* strain is *Bacillus subtilis*. In another embodiment, the *Bacillus* strain is *Bacillus pumilus*.

In another embodiment, enzyme producing strains for altering gas emissions include but are not limited to *Bacillus subtilis* AGTP BS3BP5, *Bacillus subtilis* AGTP BS442, *Bacillus subtilis* AGTP BS521, *Bacillus subtilis* AGTP BS918, *Bacillus subtilis* AGTP BS1013, and *Bacillus subtilis* AGTP BS1069, *Bacillus subtilis* AGTP 944, *Bacillus pumilus* AGTP BS1068 and *Bacillus pumilus* KX11-1, strains having all the characteristics thereof, any derivative or variant thereof, and mixtures thereof.

The enzyme producing strain(s) for altering gas emissions may be administered as a single strain, one or more combination(s) of the strain(s), one or more supernatant(s) from a culture of the strain(s), feed including one or more strain(s) or mixtures thereof.

Gases that can be altered by the enzyme producing strains include but are not limited to ammonia, carbon dioxide, methane, and hydrogen sulfide.

In another embodiment, the disclosure relates to a to a method for altering gas emissions in a room housing an animal comprising administering an enzyme producing strain to an animal in an effective amount to alter gas emissions in the room as compared to a room housing animals that were not administered the enzyme producing strains. In one embodiment, the animal is a pig. In another embodiment, the room is located in a barn. In one embodiment, methane and hydrogen sulfide gas emissions are reduced in the room housing animals that were administered the enzyme producing strains.

In another embodiment, the disclosure relates to a method for altering gas emissions in a room housing animals comprising administering an enzyme producing strain to an animal in an effective amount to alter gas emissions in the room housing the animal; and measuring the amount of gas in the room.

In another embodiment, the disclosure relates to a method for altering gas emissions in a manure storage unit comprising administering an enzyme producing strain to an animal in an effective amount to alter gas emissions in the manure storage unit as compared to a manure storage unit with manure from animals that were not administered the enzyme producing strains. In one embodiment, the animal is a pig. In another embodiment, the manure storage unit is a manure pit.

In another embodiment, the disclosure relates to a method for altering gas emissions in a manure storage unit comprising contacting an enzyme producing strain directly to the manure storage unit in an effective amount to alter gas emissions as compared to a manure storage unit without the enzyme producing strains. In one embodiment, the animal is a pig. In another embodiment, the manure storage unit is a manure pit.

In one embodiment, methane and hydrogen sulfide gas emissions are reduced.

Methods for Alleviating an Inflammatory Response

In another embodiment, the disclosure relates to a method of alleviating inflammatory effects in an animal comprising administering an enzyme producing strain to the animal in an amount effective to alleviate or inhibit the inflammatory response. In one embodiment, the animal is a mammal. In another embodiment, the animal is poultry. In another embodiment, the animal is a chicken. In still another embodiment, the animal is a pig.

The enzyme producing strains can alleviate or inhibit the inflammatory response from 2-5%, 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, 85-90%, 90-95%, and greater than 95% as compared to a reference control (e.g., an agent with no anti-inflammatory properties, such as a buffered saline or a strain with no anti-inflammatory properties).

In one embodiment, the enzyme producing strains for alleviating inflammatory effects in an animal comprise a *Bacillus* strain. In one embodiment, the *Bacillus* strain is *Bacillus subtilis*. In another embodiment, the *Bacillus* strain is *Bacillus pumilus*.

In another embodiment, the enzyme producing strains for alleviating inflammatory effects in an animal comprise *Bacillus subtilis* AGTP BS3BP5, *Bacillus subtilis* AGTP BS442, *Bacillus subtilis* AGTP BS521, *Bacillus subtilis* AGTP BS918, *Bacillus subtilis* AGTP BS1013, and *Bacillus subtilis* AGTP BS1069, *Bacillus subtilis AGTP* 944, *Bacillus pumilus* AGTP BS1068 and *Bacillus pumilus* KX11-1, strains having all the characteristics thereof, any derivative or variant thereof, and mixtures thereof.

In another embodiment, the enzyme producing strains for alleviating inflammatory effects in an animal is a composition comprising *Bacillus subtilis* AGTP BS1013, *Bacillus subtilis* AGTP BS3BP5, and *Bacillus subtilis* AGTP 944.

The enzyme producing strains can alleviate or inhibit the inflammatory response by reducing the expression of genes involved in the inflammatory response. In one embodiment, the enzyme producing strains can reduce the expression of a gene from 2-5%, 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, 85-90%, 90-95%, and greater than 95% as compared to a reference control (e.g., an agent with no anti-inflammatory properties, such as a buffered saline or a strain with no anti-inflammatory properties).

In another embodiment, the enzyme producing strains can alleviate or inhibit the inflammatory response by reducing the expression of a protein involved in the inflammatory response.

In still another embodiment, the enzyme producing strains can alleviate or inhibit the inflammatory response by reducing the activity of a protein involved in the inflammatory response.

In another embodiment, the enzyme producing strains can reduce the expression or activity of a protein from 2-5%, 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, 85-90%, 90-95%, and greater than 95% as compared to a reference control (e.g., an agent with no anti-inflammatory properties, such as a buffered saline or a strain with no anti-inflammatory properties).

In another embodiment, enzyme producing strains can reduce expression of a gene or reduce activity of a protein involved in any pathway involved in the inflammatory response including but not limited to adhesion-extravasation-migration; apoptosis signaling; calcium signaling; complement cascade; cytokines, and cytokine signaling; eicosanoid synthesis and signaling; glucocorticoid/PPAR signaling; G-protein coupled receptor signaling; innate pathogen detection; leukocyte signaling; MAPK signaling; natural killer cell signaling; NK-kappa B signaling; antigen presentation; PI3K/AKT signaling; ROS/glutathione/cytotoxic granules; and TNF superfamily and signaling.

In one embodiment, the enzyme producing strains can reduce the activity of or expression of cytokines including but not limited to interleukins, interferons, tumor necrosis factor, erythropoietin, Tpo, Flt-3L, SCF, M-CSF, and MSP.

In one embodiment, interleukins include but are not limited to interleukin (IL)-1, IL-1α, IL-1-like, IL-β, IL-1RA, IL-2, IL-3, IL-4, IL-5, IL-6, IL-6-like, IL-7, IL-8, IL-9, IL-10, IL-10-like, IL-11, IL-12, IL-13, IL-14, IL-15, IL-16, IL-17, IL-18, IL-19, IL-20, IL-21, IL-22, GM-CSF, and OSM.

In another embodiment, interferons include but are not limited to IFN-α, IFN-β, and IFN-gamma.

In another embodiment, tumor necrosis factor includes but is not limited to CD154, LT-β, TNF-α, TNF-β, TGF-β1, TGF-β2, TGF-β3, 4-1BBL, APRIL, CD70, CD153, CD178, GITRL, LIGHT, OX40L, TALL-1, TRAIL, TWEAK, and TRANCE.

In another embodiment, the enzyme producing strains can be used to reduce the activity of or reduce the expression of chemokines including but not limited to C chemokines, CC chemokines, CXC chemokines, and CXC3 chemokines.

In one embodiment, C chemokines include but are not limited to XCL1, and XCL2.

In another embodiment, CC chemokines include but are not limited to CCL1, CCL 2, CCL 3, CCL 4, CCL 5, CCL 6, CCL 7, CCL 8, CCL 9, CCL 10, CCL 11, CCL 12, CCL 13, CCL 14, CCL 15, CCL 16, CCL 17, CCL 18, CCL 19, CCL 20, CCL 21, CCL 22, CCL 23, CCL 24, CCL 25, CCL 26, CCL 27, and CCL 28.

In another embodiment, CXC chemokines include but are not limited to CXCL1, CXCL2, CXCL3, CXCL4, CXCL5, CXCL6, CXCL7, CXCL8, CXCL9, CXCL10, CXCL11, CXCL12, CXCL13, and CXCL14.

The enzyme producing strain(s) for alleviating an inflammatory response may be administered as a single strain, one or more combination(s) of the strain(s), one or more supernatant(s) from a culture of the strain(s), feed including one or more strain(s) or mixtures thereof.

Strains, methods and compositions disclosed herein can be further described by the number paragraphs.

1. An isolated *Bacillus* strain having enzymatic activity.

2. The strain of paragraph 1, wherein the enzymatic activity is selected from the group consisting of cellulase activity, α-amylase activity, xylanase activity, esterase, β-mannanase, lipase activity, protease activity, and combinations thereof.

3. The strain of any of the preceding paragraphs, wherein the enzymatic activity is selected from the group consisting of zeinase activity and soy protease activity, and combinations thereof.

4. The strain of any of the preceding paragraphs, wherein, when the strain is administered to an animal, the strain provides an improvement in at least one of the breakdown of complex dietary components, manure waste problems, the efficiency of swine production, carcass characteristics, and swine performance when feeding high levels of DDGS as compared to a control animal.

5. The strain of any of the preceding paragraphs, wherein, when the strain is administered to an animal, the strain provides an improvement in at least one of the breakdown of complex dietary components, manure waste problems, the efficiency of swine production, carcass characteristics, and swine performance when feeding high levels of DDGS by at least 2% compared to a control animal.

6. The strain of any of the preceding paragraphs, wherein, when the strain is administered to an animal, the strain provides an improvement in at least one of the following: body weight, average daily gain, average daily feed intake, feed efficiency, carcass characteristics, nutrient digestibility and manure waste problems as compared to a control animal.

7. The strain of any of the preceding paragraphs, wherein, when the strain is administered to an animal, the strain provides an improvement in at least one of the following: body weight, average daily gain, average daily feed intake, feed efficiency, carcass characteristics, nutrient digestibility and manure waste problems by at least 2% compared to a control.

8. The strain of any of the preceding paragraphs, wherein the strain is selected from the group consisting of the species

*B. subtilis* and *B. pumilus*, strains having all the characteristics thereof, any derivative or variant thereof, and mixtures thereof.

9. The strain of any of the preceding paragraphs, wherein the strain(s) is(are) selected from the group consisting of *Bacillus subtilis* AGTP BS3BP5 (NRRL B-50510), *Bacillus subtilis* AGTP BS442 (NRRL B-50542), *Bacillus subtilis* AGTP BS521 (NRRL B-50545), *Bacillus subtilis* AGTP BS918 (NRRL B-50508), *Bacillus subtilis* AGTP BS1013 (NRRL B-50509), *Bacillus subtilis* AGTP BS1069 (NRRL B-50544), *Bacillus subtilis* AGTP 944 (NRRL B-50548), *Bacillus pumilus* AGTP BS1068 (NRRL B-50543), and *Bacillus pumilus* KX11-1 (NRRL B-50546), and strains having all the characteristics thereof and any derivative or variant thereof, and mixtures thereof.

10. The strain of any of the preceding paragraphs, wherein the strain(s) is(are) selected from the group consisting of *Bacillus subtilis* AGTP BS3BP5 (NRRL B-50510), *Bacillus subtilis* AGTP BS442 (NRRL B-50542), *Bacillus subtilis* AGTP BS521 (NRRL B-50545), *Bacillus subtilis* AGTP BS918 (NRRL B-50508), *Bacillus subtilis* AGTP BS1013 (NRRL B-50509), *Bacillus subtilis* AGTP BS1069 (NRRL B-50544), *Bacillus subtilis* AGTP 944 (NRRL B-50548), *Bacillus pumilus* AGTP BS1068 (NRRL B-50543), and *Bacillus pumilus* KX11-1 (NRRL B-50546) any derivative or variant thereof, and mixtures thereof.

11. The strain of any of the preceding paragraphs, wherein the *Bacillus* strain is *Bacillus subtilis* AGTP BS3BP5 (NRRL B-50510).

12. The strain of any of the preceding paragraphs, wherein the *Bacillus* strain is *Bacillus subtilis* AGTP BS442 (NRRL B-50542).

13. The strain of any of the preceding paragraphs, wherein the *Bacillus* strain is *Bacillus subtilis* AGTP BS521 (NRRL B-50545).

14. The strain of any of the preceding paragraphs, wherein the *Bacillus* strain is *Bacillus subtilis* AGTP BS918 (NRRL B-50508).

15. The strain of any of the preceding paragraphs, wherein the *Bacillus* strain is *Bacillus subtilis* AGTP BS1013 (NRRL B-50509).

16. The strain of any of the preceding paragraphs, wherein the *Bacillus* strain is *Bacillus pumilus* AGTP BS1068 (NRRL B-50543).

17. The strain of any of the preceding paragraphs, wherein the *Bacillus* strain is *Bacillus subtilis* AGTP BS1069 (NRRL B-50544).

18. The strain of any of the preceding paragraphs, wherein the *Bacillus* strain is *Bacillus subtilis* AGTP 944 (NRRL B-50548).

19. The strain of any of the preceding paragraphs, wherein the *Bacillus* strain is *Bacillus pumilus* KX11-1 (NRRL B-50546).

20. A composition comprising supernatant from one or more culture(s) of one or more strain(s) according to any one of paragraphs 1-19, and mixtures thereof.

21. A composition comprising one or more strain(s) according to any one of paragraphs 1-19, and mixtures thereof.

22. The composition of paragraphs 20 or 21, wherein the strains are *Bacillus subtilis* AGTP BS3BP5 (NRRL B-50510), *Bacillus subtilis* AGTP BS918 (NRRL B-50508), and *Bacillus subtilis* AGTP BS1013 (NRRL B-50509).

23. The composition of paragraphs 20 or 21, wherein the strains are *Bacillus subtilis* AGTP BS3BP5 (NRRL B-50510), *Bacillus subtilis* AGTP BS944 (NRRL B-50509), and *Bacillus subtilis* AGTP BS1013 (NRRL B-50509).

24. A feed for an animal, wherein the feed is supplemented with the isolated strain(s) according to any one of paragraphs 1-19 or with the composition(s) according to any one of paragraphs 20-23 or mixtures thereof.

25. A method comprising the step of administering to an animal an effective amount of the strain(s) according to any one of paragraphs 1-19 or the composition(s) according to any one of paragraphs 20-23, the feed according to paragraph 24 or mixtures thereof, wherein administration enzymatically breaks down at least one of fiber, protein, carbohydrate, and lipid in a diet fed to the animal when feeding high levels of DDGS to the animal.

26. A method comprising the step of administering to an animal an effective amount of the strain(s) according to any one of paragraphs 1-19, the composition(s) according to any one of paragraphs 20-23, the feed according to paragraph 24, or mixtures thereof, wherein the administration improves at least one of the breakdown of complex dietary components, manure waste problems, the efficiency of swine production, carcass characteristics, and swine performance.

27. A method comprising the step of administering to an animal an effective amount of the strain(s) according to any one of paragraphs 1-19, the composition(s) according to any one of paragraphs 20-23, the feed according to paragraph 24, or mixtures thereof, wherein the administration improves at least one of the following body weight, average daily gain, average daily feed intake, feed efficiency, carcass characteristics, nutrient digestibility and manure waste problems as compared to a control animal.

28. A method comprising the step of administering to poultry an effective amount of the strain(s) according to any one of paragraphs 1-19, the composition(s) according to any one of paragraphs 20-23, the feed according to paragraph 24, or mixtures thereof, wherein the administration improves at least one of the following body weight, average daily gain, average daily feed intake, feed efficiency, carcass characteristics, nutrient digestibility and manure waste problems as compared to a control animal.

29. A method comprising the step of administering to a pig an effective amount of the strain(s) according to any one of paragraphs 1-19, the composition(s) according to any one of paragraphs 20-23, the feed according to paragraph 24, or mixtures thereof, wherein the administration improves at least one of the following body weight, average daily gain, average daily feed intake, feed efficiency, carcass characteristics, nutrient digestibility and manure waste problems as compared to a control animal.

30. The method of paragraphs 25-29, wherein the composition is the composition of paragraph 22 or 23.

31. The method of any one of paragraphs 25-30, wherein the strain(s) is/are administered at about $1 \times 10^5$ to about $1 \times 10^{11}$ CFU/animal/day.

32. The method of any one of paragraphs 25-27, and 29-31, wherein the animal is a swine.

33. The method of any one of paragraphs 25-32, wherein the animal is fed high levels of dried distillers grains with solubles (DDGS).

34. The method of any one of paragraphs 25-33, wherein the animal is fed dried distillers grains with solubles (DDGS) at a rate of over 10% of the animal's diet.

35. The method of any one of paragraphs 25-34, wherein the animal is fed dried distillers grains with solubles (DDGS) at a rate of over 30% of the animal's diet.

36. A method comprising the step of administering an effective amount of the strain(s) according to any one of paragraphs 1-19 or with the composition(s) according to any one of paragraphs 20-23 to a swine manure storage unit.

37. The method of paragraph 36, wherein the swine manure storage unit is a manure pit.

38. The method of paragraph 36 or 37, further comprising improving at least one of the following: less incidence of foaming, less accumulation of solids, and less nitrogen, sulfur, phosphorus, fiber-bound nitrogen, total protein, fat, and fiber content when compared to a control manure pit.

39. A method of forming a composition, the method comprising: (a) growing, in a liquid broth, a culture including one of the isolated strain(s) according to any one of paragraphs 1-19; and (b) separating the strain from the liquid broth.

40. The method of paragraph 39, further comprising freeze drying the isolated strain and adding the freeze-dried strain to a carrier.

41. The method of paragraph 39 or 40, further comprising retaining the liquid broth after the strain has been separated from it to generate a supernatant.

42. A method for improving growth performance of an animal comprising administering to an animal an effective amount of the strain(s) according to any one of paragraphs 1-19, the composition(s) according to any one of paragraphs 20-23, the feed according to paragraph 24, or mixtures thereof as compared to a control animal.

43. The method of paragraph 42 wherein the administration improves at least one of the following body weight, average daily gain, average daily feed intake, feed efficiency, carcass characteristics, nutrient digestibility and manure waste problems.

44. A method for improving manure storage units comprising administering to an animal an effective amount of the strain(s) according to any one of paragraphs 1-19, the composition(s) according to any one of paragraphs 20-23, the feed according to paragraph 24, or mixtures thereof in an effective amount to improve the manure storage unit as compared to the manure from an control animal, which is stored in a second manure storage unit.

45. A method for improving manure storage units comprising contacting an effective amount of the strain(s) according to any one of paragraphs 1-19, the composition(s) according to any one of paragraphs 20-23, the feed according to paragraph 24, or mixtures thereof directly to the manure storage unit.

46. The method of paragraphs 44 or 45 wherein improvements include at least one of the following: less incidence of foaming, less accumulation of solids, and less nitrogen, sulfur, phosphorus, fiber-bound nitrogen, total protein, fat, and fiber content than control manure pits.

47. A method of controlling or reducing foam in a manure pit comprising administering an effective amount of the strain(s) according to any one of paragraphs 1-19, the composition(s) according to any one of paragraphs 20-23, the feed according to paragraph 24, or mixtures thereof to animals whose manure is stored in the manure pit.

48. A method of controlling or reducing foam in a manure pit comprising contacting an effective amount of the strain(s) according to any one of paragraphs 1-19, the composition(s) according to any one of paragraphs 20-23, the feed according to paragraph 24, or mixtures thereof directly to the manure pit.

49. A method of altering the microbial ecology in a manure pit comprising administering an effective amount of the strain(s) according to any one of paragraphs 1-19, the composition(s) according to any one of paragraphs 20-23, the feed according to paragraph 24, or mixtures thereof to animals whose manure is stored in the manure pit.

50. A method of altering the microbial ecology in a manure pit comprising contacting an effective amount of the strain(s) according to any one of paragraphs 1-19, the composition(s) according to any one of paragraphs 20-23, the feed according to paragraph 24, or mixtures thereof directly to the manure pit.

51. A method of altering volatile fatty acid composition in a manure pit comprising administering an effective amount of the strain(s) according to any one of paragraphs 1-19, the composition(s) according to any one of paragraphs 20-23, the feed according to paragraph 24, or mixtures thereof to animals whose manure is stored in the manure pit.

52. A method of altering volatile fatty acid composition in a manure pit comprising contacting an effective amount of the strain(s) according to any one of paragraphs 1-19, the composition(s) according to any one of paragraphs 20-23, the feed according to paragraph 24, or mixtures thereof directly to the manure pit.

53. A method of altering gas emissions in a room housing an animal comprising administering an effective amount of the strain(s) according to any one of paragraphs 1-19, the composition(s) according to any one of paragraphs 20-23, the feed according to paragraph 24, or mixtures thereof to animals in an effective amount to reduce gas emissions.

54. A method of altering gas emissions in a manure storage unit comprising administering an effective amount of the strain(s) according to any one of paragraphs 1-19, the composition(s) according to any one of paragraphs 20-23, the feed according to paragraph 24, or mixtures thereof to animals in an effective amount to reduce gas emissions.

55. A method of altering gas emissions in a manure storage unit comprising contacting an effective amount of the strain(s) according to any one of paragraphs 1-19, the composition(s) according to any one of paragraphs 20-23, the feed according to paragraph 24, or mixtures thereof directly to the manure storage unit in an effective amount to reduce gas emissions.

56. A method of alleviating an inflammatory response comprising administering an effective amount of the strain(s) according to any one of paragraphs 1-19, the composition(s) according to any one of paragraphs 20-23, the feed according to paragraph 24, or mixtures thereof to animals in an effective amount to alleviate the inflammatory response.

57. An isolated strain according to paragraphs 1-19 or composition according to paragraphs 20-23 or a feed according to paragraph 24 for use as a medicament to improve at least one of the breakdown of complex dietary components, manure waste problems, the efficiency of swine production, carcass characteristics, and swine performance when feeding high levels of DDGS.

58. Use of isolated strain according to paragraphs 1-19 or composition according to paragraphs 20-23 or a feed according to paragraph 24 in preparation of a medicament to provide on or more enzymes(s).

60. An isolated strain of *Bacillus* described in paragraphs 1-19 for use in improving the breakdown of complex dietary components, manure waste problems, the efficiency of swine production, carcass characteristics, and swine performance when feeding high levels of DDGS.

61. Use of isolated strain of *Bacillus* described in paragraphs 1-19 in preparation of a medicament to providing enzymatic activity.

62. Use of isolated strain of *Bacillus* described in paragraphs 1-19 in preparation of a medicament to improve at least one of the breakdown of complex dietary components, manure waste problems, the efficiency of swine production, carcass characteristics, and swine performance when feeding high levels of DDGS.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Isolation of Environmental Bacteria and Identification of Enzymatic Activities Agricultural and environmental waste samples were collected from diverse source locations over a period of several years. Upon arrival, all samples were diluted in a 1% peptone solution, spore treated for 35 minutes at 65° C. and serially diluted onto tryptic soy agar plates (BD Difco, Franklin Lakes, N.J.). Following incubation at 32° C. for 48 hours, growth of diverse unknown environmental colonies were cultured from the plates into tryptic soy broth (TSB), similarly re-incubated and stored frozen at −85° C. for later analysis.

Approximately 4000 presumptive Bacillus isolates of environmental origin were collected and screened for their ability to degrade a variety of substrates of interest. Environmental cultures were picked from library freezer stocks and incubated in 0.5 ml TSB at 32° C. for 24 hours in an orbital shaking incubator, with speed set to 130 (Gyromax 737R). High-throughput screening of these test strains was performed by replicate spot plating of 2 microliters liquid culture onto 15.0 ml of various substrate media types of interest in 100×100×15 mm grid plates. Cellulase, α-amylase, zeinase, soy protease, esterase, lipase, and xylanase activities were determined based on specific substrate utilization by the individual strains. Media components used to assay the substrate utilization properties from enzymatic activity of the environmentally derived strains are described in Table 1. Assay plates were left to dry for 30 minutes following culture application, and then incubated at 32° C. for 24 hours. Enzymatic activities for each strain were determined by measuring the zone of substrate degradation in millimeters, as indicated by clearing of the surrounding edge of colony growth. Mean values from replicate plates were recorded.

Figure 19:
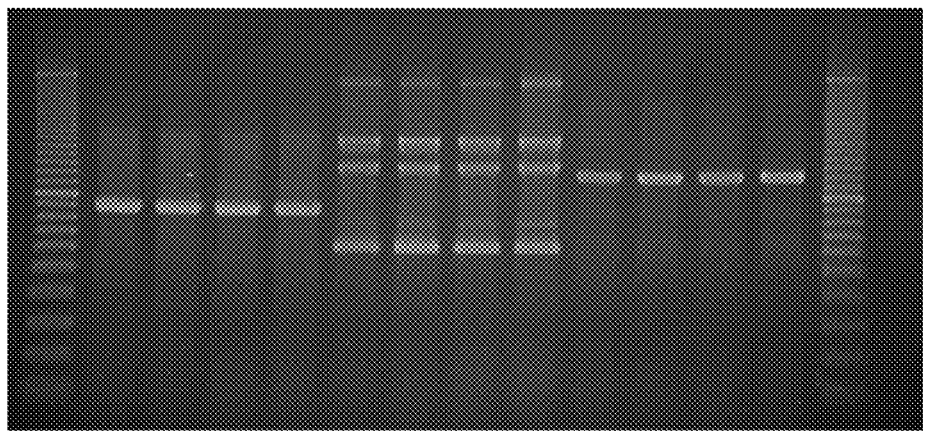
FIG. 19 is a photograph of a gel showing a RAPD PCR profile of *Bacillus pumilus* KX11-1.
Figure 20:
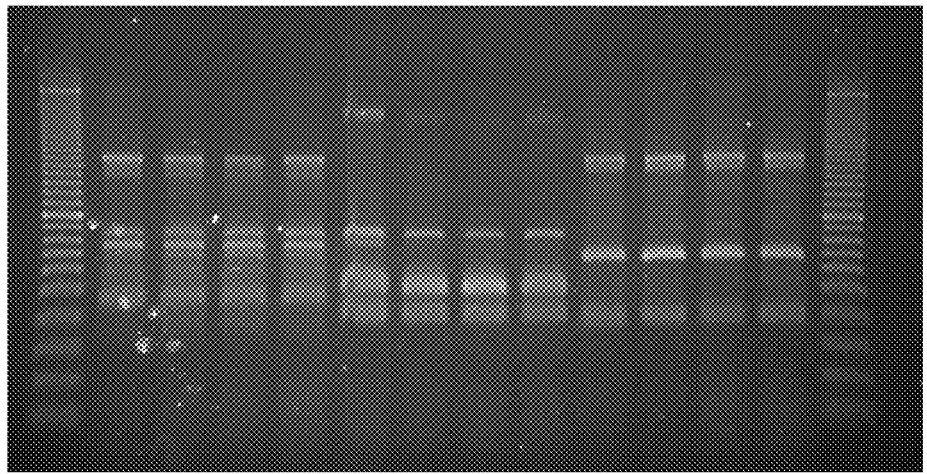
FIG. 20 is a photograph of a gel showing a RAPD PCR profile of *Bacillus pumilus* KX11-1.

Nine strains were selected from the approximately 4000 screened as candidate direct-fed microbial strains demonstrating a range of substrate activities representing the top 10% and the top 2% of enzyme activities of all the strains screened (Table 2). Based on their ability to utilize or degrade an array of relevant substrates associated with the inclusion of DDGs in feedstuffs, nine isolates were chosen as candidates for one or more direct-fed microbial(s) (DFM(s)). RAPD PCR profiles and partial 16S rDNA sequences of each strain were determined. Genus and presumptive species determination of each was made by amplifying 16S rDNA using an 8F and 1541R primer set. Purified PCR products were sequenced from both forward and reverse ends, and a contiguous sequence generated using a CAP3 assembly program. The nine selected strains are: *Bacillus subtilis* AGTP BS3BP5 (FIGS. 1 & 2), *Bacillus subtilis* AGTP BS442 (FIGS. 3 & 4), *Bacillus subtilis* AGTP BS521 (FIGS. 5 & 6), *Bacillus subtilis* AGTP BS918 (FIGS. 7 & 8), *Bacillus subtilis* AGTP BS1013 (FIGS. 9 & 10), *Bacillus pumilus* AGTP BS1068 (FIGS. 11 & 12), *Bacillus subtilis* AGTP BS1069 (FIGS. 13 & 14), *Bacillus subtilis* AGTP 944, (FIGS. 15-18), and *Bacillus pumilus* KX11-1 (FIGS. 19-21).

TABLE 1

Media components used to assay the enzymatic activities illustrated by substrate utilization properties of environmentally derived *Bacillus*.

| Plate Assay | Media Composition | Extra Visualization Requirements |
|---|---|---|
| α-Amylase | Nutrient Agar, 2% Corn Starch | .05% Iodine Stain Solution |
| Soy Protease | Nutrient agar, 2% Purified Soy Protein | None; Measure Zone of Clearing in opaque media |
| Cellulase | 0.1% Ammonium Sulfate, 0.1% Potassium Phosphate Dibasic, 0.1% Yeast Extract, 1.0% Polypeptone, 1.5% Agar, 0.75% Carboxymethyl Cellulose (CMC) | 30 minute 0.05% Congo Red Dye stain, follwed by 1M NaCl rinse. |
| Esterase/Lipase | 1.0% Polypeptone, 1.5% Agar, 0.5% Yeast Extract, 1.5% Tween 80, 1.5% Tributyrin, 0.01% Victoria Blue B Dye (filtered). | None; Measure Zone of Clearing in opaque media |
| Zeinase | Nutrient Agar, 2% Purified Zein, solubilized in 70% methanol | None; Measure Zone of Clearing in opaque media |
| Xylanase | Nutrient Agar, 2% Xylan | None; Measure Zone of Clearing in opaque media |

TABLE 2

Summary of direct fed microbial candidate strain enzymatic activity.[a]

| Isolate Number[b] | CMCase (Cellulase) | Esterase | Corn Starch Amylase | Soy Protease | Zein Protease | Xylanase |
|---|---|---|---|---|---|---|
| BS442  | 1.67   | 3.92[1] | 0.92    | 2.00    | 3.00    | 2.50 |
| BS521  | 7.00[1] | 2.00[2] | 1.00    | 1.75    | 3.69[2] | 4.00 |
| BS918  | 3.25   | 3.25[1] | 0.50    | 4.00[1] | 5.00[1] | 5.50 |
| BS1013 | 6.50[1] | 2.00[2] | 2.50[2] | 2.75[2] | 4.38[2] | 4.00 |
| BP1068 | 3.00   | 0.50    | 4.00[1] | 4.00[1] | 4.25[2] | 6.00 |
| BS1069 | 4.00[2] | 0.50    | 2.00[2] | 4.00[1] | 5.00[1] | 4.00 |
| BS9444 | 6.5    | 2.25    | 3.25    | 0.50    | 4.50    | 3.5 |
| KX11-1 | 2.5    | —       | —       | 2.00    | —       | 5 |
| BS3BP5 | 3.25   | 2.58[2] | 2.00[2] | 1.50    | 4.00[1] | 3.00 |

[a]Values represent the zone of substrate degradation in millimeters (mm), as indicated by clearing of the surrounding edge of colony growth for each strain.
[b]For strain isolate designations, BS = *Bacillus subtilis*; BP = *Bacillus pumilus*
[1]Values represent the top 2% of enzymatic activity in the specific class of all 4000 strains screened.
[2]Values represent the top 10% of enzymatic activity in the specific class of all 4000 strains screened.

Example 2

Comparison of the Enzymatic Activity of Novel Bacillus Strains and the Three-Strain Commercial Bacillus Direct-Fed Microbial, Microsource® S The three Microsource® S *Bacillus* strains (*B. subtilis* 27 (BS 27), *B. licheniformis* (previously thought to be *B. amyloliquefaciens*) 842, and *B. licheniformis* 21 (Bl 21)) were picked from individual library freezer stocks and incubated in 0.5 ml TSB at 32° C. for 24 hours in an orbital shaking incubator, with speed set to 130 (Gyromax 737R). High-throughput screening of these product strains was performed by replicate spot plating of 2 microliters liquid culture onto 15.0 ml of various substrate media types of interest in 100× 100×15 mm grid plates. Cellulase, soy protease, and esterase/lipase activities were determined based on specific substrate utilization by the individual strains. Media components used to assay the substrate utilization properties from enzymatic activity of the environmentally derived strains are described in Table 3. Assay plates were left to dry for 30 minutes following culture application, and then incubated at 32° C. for 24 hours. Enzymatic activities for each strain were determined by measuring the zone of substrate degradation in millimeters, as indicated by clearing of the surrounding edge of colony growth. Mean values from replicate plates were recorded and compared to the values derived from the novel *Bacillus* strains identified in Example 1 (Table 4). Only one strain of the three Microsource® S *Bacillus* strains demonstrated any substantial enzymatic activity when compared to the novel *Bacillus* strains selected for their substrate degradation activity; this was exemplified by the soy protease activity of Microsource® S *Bacillus subtilis* strain BS27.

TABLE 3

Media components used to assay the enzymatic activities illustrated by substrate utilization properties of environmentally derived *Bacillus*.

| Plate Assay | Media Composition | Extra Visualization Requirements |
|---|---|---|
| Soy Protease | Nutrient agar, 2% Purified Soy Protein | None; Measure Zone of Clearing in opaque media |
| Cellulase | 0.1% Ammonium Sulfate, 0.1% Potassium Phosphate Dibasic, 0.1% Yeast Extract, 1.0% Polypeptone, 1.5% Agar, 0.75% Carboxymethyl Cellulose (CMC) | 30 minute 0.05% Congo Red Dye stain, follwed by 1M NaCl rinse. |
| Esterase/ Lipase | 1.0% Polypeptone, 1.5% Agar, 0.5% Yeast Extract, 1.5% Tween 80, 1.5% Tributyrin, 0.01% Victoria Blue B Dye (filtered). | None; Measure Zone of Clearing in opaque media |

TABLE 4

Enzymatic activity of Microsource ® S *Bacillus* product strains compared to novel *Bacillus* strains selected for enhanced substrate degradation.[a]

| Isolate Name | CMCase (Cellulase) | Esterase | Soy Protease |
|---|---|---|---|
| MicroSource ® S product strains | | | |
| BS27 | 0.00 | 0.60 | 2.50[2] |
| BL21 | 0.30 | 0.50 | 0.80 |
| BL842 | 0.00 | 0.30 | 0.00 |
| BS3BP5 | 3.25 | 2.58[2] | 1.50 |
| BS442 | 1.67 | 3.92[1] | 2.00 |
| BS521 | 7.00[1] | 2.00[2] | 1.75 |
| BS918 | 3.25 | 3.25[1] | 4.00[1] |
| BS1013 | 6.50[1] | 2.00[2] | 2.75[2] |
| BP1068 | 3.00 | 0.50 | 4.00[1] |
| BS1069 | 4.00[2] | 0.50 | 4.00[1] |

[a]Values represent the zone of substrate degradation in millimeters (mm), as indicated by clearing of the surrounding edge of colony growth for each strain.
[1]Values represent the top 2% of enzymatic activity in the specific class of all 4000 strains screened.
[2]Values represent the top 10% of enzymatic activity in the specific class of all 4000 strains screened.

Example 3

Animal Feeding Trial Demonstrating Improved Growth Performance in Response to Bacillus subtilis Strain 3BP5 Added to Swine Diets A pig feeding trial was conducted to assess the effects of a *Bacillus*-based direct-fed microbial (DFM) feed additive on body weight gain, feed intake, and feed efficiency of grower-finisher pigs. Approximately 180 pigs (Monsanto Choice Genetics GPK 35 females mated to EB Ultra sires) were blocked into three weight blocks by initial body weight and penned in groups of 5 pigs/pen at the completion of the nursery period. Pigs were moved to a wean-to-finish facility and housed 5 pigs/pen in totally slatted pens (1.52 m×3.05 m) equipped a single-hole feeder, and wean-to-finish cup waterers. Initial minimum ambient room temperature was maintained at approximately 78° F. During the finishing phase, minimum temperature was further reduced to 70° F. Feed and water were available freely throughout the study.

One of two dietary treatments were assigned to each pen (18 pens/treatment) within each block, and administered during Phase 1 (50 to 90 lbs), Phase 2 (90 to 130 lbs), Phase 3 (130 to 180 lbs), Phase 4 (180 to 230 lbs) and Phase 5 (230 lbs to market at approximately 270 lbs). The two dietary treatments consisted of a basal control diet devoid of DFM 3BP5 and the basal diet with DFM 3BP5 in a five phase grower-finisher pig study. Diets were formulated to meet or exceed NRC (1988) requirements and consisted predominately of corn, soybean meal, and DDGS at 47%, 18.6%, and 30% of the diet, respectively. Strain *Bacillus subtilis* AGTP BS3BP5 was added to the diet at $7.3 \times 10^7$ CFU/kg feed and supplied approximately $1 \times 10^8$ CFU/head/day based on average daily feed intake (ADFI). Data collected were average daily gain, average daily feed intake, and feed required per unit of gain during each of the five growing-finishing phases. Pigs were removed from the study when the average pig weight of the entire barn reached approximately 270 lbs.

Performance data were analyzed as a randomized complete block design with pen as the experimental unit and blocks based on initial body weight. Analysis of variance was performed using the GLM procedures of SAS (SAS Institute, Inc., Cary, N.C.).

Pigs fed diets containing strain *Bacillus subtilis* AGTP BS3BP5 had greater (P<0.01) average daily gain (ADG) and gain:feed during the Phase 1 growing period and tended (P<0.08) to have greater ADG and gain:feed in the combined Phase 1 and Phase 2 periods compared to pigs fed the control diet (Table 5). The increase in ADG during the first growing period resulted in pigs fed strain *Bacillus subtilis* AGTP BS3BP5 having greater (P<0.01) body weight at the end of the Phase 1 period compared to pigs fed the control diet.

TABLE 5

Growth performance responses of pigs fed *Bacillus subtilis* AGTP 3BP5 compared to pigs fed control diets.

| Trait | Treatment | | SE[1] | P-value |
|---|---|---|---|---|
| | Control | 3BP5 | | |
| ADG, g | | | | |
| Phase 1 | 704 | 766 | 10 | <0.01 |
| Phase 2 | 1020 | 1017 | 19 | 0.92 |
| Phase 1-2 | 861 | 890 | 11 | 0.08 |
| Phase 3 | 1114 | 1103 | 18 | 0.68 |
| Phase 1-3 | 942 | 958 | 8 | 0.15 |
| Phase 4 | 983 | 959 | 28 | 0.55 |
| Phase 1-4 | 952 | 958 | 9 | 0.67 |
| Phase 5 | 881 | 858 | 19 | 0.39 |
| Phase 1-5 | 939 | 939 | 8 | 0.97 |
| ADFI, kg | | | | |
| Phase 1 | 1.571 | 1.604 | 0.028 | 0.42 |
| Phase 2 | 2.591 | 2.562 | 0.042 | 0.64 |
| Phase 1-2 | 2.074 | 2.077 | 0.032 | 0.95 |
| Phase 3 | 3.331 | 3.291 | 0.033 | 0.41 |
| Phase 1-3 | 2.475 | 2.464 | 0.029 | 0.80 |
| Phase 4 | 3.120 | 3.130 | 0.055 | 0.90 |
| Phase 1-4 | 2.640 | 2.647 | 0.032 | 0.94 |
| Phase 5 | 3.503 | 3.426 | 0.049 | 0.28 |
| Phase 1-5 | 2.801 | 2.788 | 0.032 | 0.78 |
| Gain:feed | | | | |
| Phase 1 | 0.445 | 0.477 | 0.008 | <0.01 |
| Phase 2 | 0.393 | 0.396 | 0.006 | 0.67 |
| Phase 1-2 | 0.413 | 0.428 | 0.005 | 0.07 |
| Phase 3 | 0.333 | 0.336 | 0.007 | 0.75 |
| Phase 1-3 | 0.379 | 0.388 | 0.005 | 0.14 |
| Phase 4 | 0.314 | 0.306 | 0.005 | 0.30 |
| Phase 1-4 | 0.359 | 0.363 | 0.003 | 0.32 |
| Phase 5 | 0.252 | 0.250 | 0.005 | 0.77 |
| Phase 1-5 | 0.334 | 0.337 | 0.002 | 0.45 |
| Weight, kg | | | | |
| Initial | 24.85 | 24.71 | 0.04 | 0.02 |
| Phase 1 | 39.63 | 40.80 | 0.22 | <0.01 |
| Phase 2 | 61.07 | 62.14 | 0.49 | 0.13 |
| Phase 3 | 83.40 | 84.21 | 0.56 | 0.31 |
| Phase 4 | 105.04 | 105.30 | 0.86 | 0.83 |
| Phase 5 | 123.04 | 122.46 | 0.88 | 0.65 |

[1]SE = standard error

Example 4

Animal Feeding and Manure Pit Mass Balance Trial Demonstrating the Effects of a *Bacillus subtilis* Strain Combination Added to Swine Diets A pig feeding trial was conducted to assess the effects of a *Bacillus*-based direct-fed microbial (DFM) administered in the diet to grower-finisher pigs on growth performance responses (average daily gain (ADG), average daily feed intake (ADFI), and gain:feed), carcass yield and quality measurements, manure nutrient composition, microbial composition of manure pit, and gas emissions (ammonia, methane, and hydrogen sulfide) from the manure pit. A total of 720 pigs (Yorkshire-Landrace×Duroc genotype) were housed in 12 rooms with 12 pens/room and 5 pigs/pen. Each room contained two manure pits with capacity to store manure for an entire wean-to-finish period. Each manure pit is located under 6 pens with a wall under the central walkway dividing the two pits in each room. Each of the twelve rooms was equipped to monitor gas emissions from each independently ventilated room. Pigs were weaned and placed in pens prior to the start of the study and began to receive experimental test feed when they had reached an average body weight of 29.5 kg. Pigs were fed for five feeding phases lasting three weeks each, and ending when pigs reached an average slaughter weight of 120 kg.

Two dietary treatments were administered to pigs on trial, consisting of a control diet and a diet supplemented with a combination of *Bacillus* strains (strains BS1013, BS918, and BS3BP5). Diets were formulated to meet or exceed NRC (1988) requirements and consisted predominately of corn, soybean meal, and DDGS at 50%, 20%, and 30% of the diet, respectively. The three strains in the *Bacillus* combination DFM were equally represented in the experimental test material that contained $1.47 \times 10^8$ CFU of the DFM per gram of material. The *Bacillus* combination DFM was added to the diet at $7.3 \times 10^7$ CFU/kg feed and supplied approximately $1 \times 10^8$ CFU/head/day based on average daily feed intake.

Pig performance measures (average daily gain (ADG), average daily feed intake (ADFI), gain:feed) were determined at the end of each feeding phase. These data were represented by 72 replicates/treatment). Manure pits were vacuum sampled at week 0 (initially and prior to pigs receiving treatment), week 9, and week 15 and proximate analysis was performed on the nutrients contained in the swine manure waste (12 replicates/treatment). A subsample on each day was also obtained to determine volatile fatty acid content and microbial community analysis (12 replicates/treatment). Furthermore, at the week 15 sampling at the end of the trial, pits were emptied into a mixing container to homogenize the entire manure pit contents, determine manure pit volume and to sample for nutrient analysis. Gas emissions were measured in each room to determine ammonia, methane, and hydrogen sulfide gas production (6 replicates/treatment). At the end of the study, pigs were sent to a commercial slaughter facility and carcass data such as percent lean yield, dressing percentage, and iodine value were collected (72 replicates/treatment).

Referring now to Table 6, preliminary performance data from the study indicate that pigs fed the *Bacillus* combination DFM had greater (P≤0.05) ADG and gain:feed during the last phase of the trial. Furthermore, pigs fed the DFM tended (P=0.15) to weigh 4.4 lb more at the end of the trial than pigs fed the control diet. Data analysis on carcass characteristics, manure nutrient and microbial composition, and gas emissions from the manure storage units including, but not limited to, manure pits have not yet been completed, but expectations are that the DFM treatment will increase percent lean yield and dressing percentage, decrease fat iodine values, result in less nutrients accumulated in the manure, shift manure microbial communities to favorable populations for solids breakdown, and decrease ammonia, methane, and hydrogen sulfide gas emissions.

TABLE 6

Effect of a three-strain combination *Bacillus* DFM administered as a dietary supplement on grower-finisher pig growth performance responses compared to pigs fed a control diet.*

| | Diet | | | |
|---|---|---|---|---|
| Item | CTL | DFM | MSE[1] | P-Value |
| ADG, lb | | | | |
| Phase 1 (wk 1-3) | 1.81 | 1.82 | 0.104 | 0.71 |
| Phase 2 (wk 3-6) | 1.67 | 1.70 | 0.165 | 0.51 |
| Phase 3 (wk 6-9) | 1.93 | 1.95 | 0.127 | 0.58 |
| Phase 4 (wk 9-12) | 1.98 | 2.01 | 0.172 | 0.64 |
| Phase 5 (wk 12-15) | 1.88 | 1.99 | 0.190 | 0.054 |
| ADFI, lb | | | | |
| Phase 1 (wk 1-3) | 3.71 | 3.7 | 0.230 | 0.87 |
| Phase 2 (wk 3-6) | 4.61 | 4.56 | 0.385 | 0.65 |
| Phase 3 (wk 6-9) | 5.75 | 5.75 | 0.391 | 0.95 |
| Phase 4 (wk 9-12) | 6.52 | 6.58 | 0.506 | 0.64 |
| Phase 5 (wk 12-15) | 6.68 | 6.71 | 0.611 | 0.87 |
| Gain:Feed | | | | |
| Phase 1 (wk 1-3) | 0.493 | 0.495 | 0.023 | 0.742 |
| Phase 2 (wk 3-6) | 0.362 | 0.378 | 0.035 | 0.127 |
| Phase 3 (wk 6-9) | 0.343 | 0.337 | 0.025 | 0.369 |
| Phase 4 (wk 9-12) | 0.305 | 0.307 | 0.024 | 0.780 |
| Phase 5 (wk 12-15) | 0.282 | 0.298 | 0.021 | 0.011 |
| Body Weight, lb | | | | |
| Initial | 63.7 | 63.9 | 1.06 | 0.48 |
| Week 9 | 175.5 | 177.0 | 6.10 | 0.38 |
| Week 15 | 258.5 | 262.9 | 10.51 | 0.15 |

*Data are the means of 24 pens/treatment.
[1]MSE = means standard error

Example 5

Demonstration of the Effectiveness of a *Bacillus*-Based Swine Manure Pit Additive Treatment to Improve Swine Manure Waste Storage, Management, and Handling A study will be conducted to assess the efficacy of a *Bacillus*-based swine manure pit additive on solids accumulation, nutrient composition, and manure foaming characteristics. Multiple production sites will be identified that contain at least three barns with separate manure handling and storage units. Manure pits at each site will be treated with a *Bacillus*-based additive at two doses and one manure pit will be left untreated. The low dose pit treatment will be added to one manure pit on each production site in 500 g of test material per 100,000 gallons of manure formulated to contain $4 \times 10^{10}$ CFU per gram of test material. The high dose treatment will be added to a different manure pit from the low dose at each production site in 500 g of test material per 100,000 gallons of manure formulated to contain $1 \times 10^{11}$ CFU per gram of test material. The third manure pit on each site will be left untreated as a control.

Samples will be obtained from each manure pit at each production site on test initially prior to any treatment and periodically (approximately once every month) over a three to six month period. Data from manure pits will be collected to assess the incidence of foaming and manure samples will be analyzed to assess solids accumulation and nutrient composition. Expectations are that treated swine manure pits will have less incidence of foaming, less accumulation of solids, and less nitrogen, sulfur, phosphorus, fiber-bound nitrogen, total protein, fat, and fiber content than control manure pits.

Example 6

Poultry Feeding Trial Demonstrating Improved Growth Performance in Response to *Bacillus* Strain Combinations Added to Poultry Diets Poultry feeding trials will be conducted to assess the effects of a *Bacillus*-based direct-fed microbial (DFM) feed additive on body weight gain, feed intake, feed efficiency and mortality of turkeys, broilers, and layers. In these studies, approximately 22 birds per treatment replicate will be randomly assigned to dietary treatments. Dietary treatments may consist of several combinations of *Bacillus* strains administered as a DFM and experimental DFM treatments combined with enzymes, compared to a relative control group of birds. *Bacillus* DFM treatments will be added to the diet at $1.5 \times 10^5$ CFU/g feed and supplied approximately $1 \times 10^7$ to $5 \times 10^7$ CFU/head/day based on average daily feed intake of various production systems (turkeys, broilers, layers). Diets will consist of corn-soybean meal-DDGS based diets. Energy and all other nutrient levels will be formulated to meet or exceed the requirements of the test birds. Diets will be fed for an approximate 42-day test period and will be fed in three feeding phases: starter (dl-20) and grower (d 21-38) and finisher (d38-42). Diets will be pelleted (approximately 75° C.), and starter feed will be crumbled.

Data from the treated groups will be compared with those of their relevant control group using the appropriate statistical tests. Body weight, body weight gain, feed intake, FCR, FCE and mortality will be analyzed by analysis of variance (ANOVA) and least significant difference tests.

When completed, it is expected that the data will support efficacy of the DFM treatment(s). Specifically, it is expected that the DFM treatment will increase percent lean yield and dressing percentage, shift gastrointestinal microbial communities to favorable populations for nutrient utilization, and improve the efficiency of bird growth, and improve egg case weights.

Example 7

Effect of *Bacillus* Direct-Fed Microbial on Swine Growth Performance, Carcass Measurements, Manure Pit Characteristics, and Environmental Gas Emissions A total of 444 pigs (200 barrows and 244 gilts) were used in a 15-wk grow-finish study to investigate the use of a *Bacillus* direct-fed microbial supplement on growth performance, carcass measurements, manure pit characteristics and gas emissions. Pigs were housed in an environmentally controlled barn, which contained 12 identical rooms with 12 pens per room. Two manure pits were contained in each of under each of the 12 rooms with 6 pens over each manure pit. Prior to the start of the experiment, manure pits were thoroughly cleaned. Manure pits were then charged with a small amount of water (~600 gallons).

Pigs allocated to test were weaned, blocked by body weight and sex, and randomly assigned to dietary treatments (Control and *Bacillus* DFM) with 4-5 pigs per pen (2-3 barrows and 2-3 gilts per pen). Prior to the start of dietary treatments, pigs were fed an adjustment diet for two weeks to seed the pits with manure. Pigs were then fed either a control diet or the control diet with *Bacillus* DFM supplementation. The *Bacillus* DFM microbial consisted of equal proportions of *Bacillus subtilis* strains AGTP BS918 (NRRL B-50508), AGTP BS1013 (NRRL B-50509) and AGTP BS3BP5 (NRRL B-50510) adding up to a guaranteed $3.0 \times 10^8$ cfu/g of DFM product, and included at a rate of 1 lb/ton in feed resulting in a concentration of $1.5 \times 10^5$ cfu/g in feed.

Dietary treatments were maintained throughout the experiment, but diets were adjusted every three weeks to better meet the nutritional needs of the pigs, resulting in 5 dietary phases (3 grower phases, 2 finisher phases) formulated to meet or exceed the nutrient requirements of pigs at each production stage in each of the five phases (NRC, 1998). Diet formulations were based on corn and soybean meal with varying levels of corn-based dried distillers grains with solubles (DDGS) over the five phases. Specifically, diets for grower Phases 1, 2, and 3 were formulated to contain 25% DDGS, the finisher Phase 4 diet contained 20% DDGS, and the second finisher Phase 5 diet contained 10% DDGS.

Pig body weight and pen feed intake were recorded every three weeks at the end of each phase. Manure pits were sampled at the start and end of each of the grower and finisher phases using a vacuum core sampler designed with a vacuum pump connected to two vacuum flasks with clear plastic tubing with a hard plastic core sampler end. Core samples of the manure pit were obtained by sampling four locations under every pen over each pit on test. Manure pit sampling locations relative to the pen included: (1) beneath the center of the pen; (2) under the pen waterer; (3) under the front of the pen feeder; and (4) beneath the far corner of the pen opposite the feeder. Manure contents were analyzed for total N, ammonium N, dry matter (DM), ash content, Ca and P (AOAC 2007). Throughout the experiment, gas concentrations in the pit air plenum and in front of the wall exhaust fan were monitored using continuous real time measuring equipment. These data were combined with ventilation rates to determine emission rates per room per day for ammonia, methane, and hydrogen sulfide gas. These data were expressed as grams of gas per pound of pig body weight gain. Methane and hydrogen sulfate concentrations were also measured for 10 consecutive days (days 70-80 for $CH_4$, days 80-90 for $H_2S$) and averaged on a room basis for total gas production analysis (n=12).

Pit samples were analyzed for nutrient (AOAC 2007) and volatile fatty acid (VFA) composition. For high pressure liquid chromatography (HPLC) detection of volatile fatty acids, 10 mL of each sample was aliquoted into 15 mL falcon tubes and stored at $-20°$ C. until HPLC analysis. After thawing, samples were centrifuged at 16.1 rad for 15 minutes. One milliliter (1 mL) of supernatant was diluted in 9 mL of 16.8 mM phosphoric acid in water/acetonitrile (98:2, v/v). Diluted supernatant was vortexed for 10 seconds and then centrifuged at 16.1 rad for 15 minutes. The supernatant was filtered (0.22 μm) and analyzed for acetic acid, propionic acid, butyric acid, 1-butyric acid, I-valeric acid, valeric acid, 4-methylvalerate using a Waters 2695 separation module (Waters Corp., Milford, Mass.) equipped with a 300×7.8 mm Aminex HPX-87H column (Biorad Laboratories, Inc., Hercules, Calif.). An isocratic method was applied with a mobile phase solvent consisting of 16.8 mM phosphoric acid in water/acetonitrile (98:2, v/v) at 0.85 mL/min flow rate and 65° C. column temperature. All analytes were detected with a 2996 PDA detector (Waters) at 211 nm absorption.

Data were analyzed using the General Linear Model procedure of SAS to test for treatment and replicate differences. Pen was the experimental unit for growth performance and carcass data, pit was the experimental unit for excretion and VFA data and room was the experimental unit for gas emission data.

Results

Pigs averaged 64.5 lb at the start of the experiment and weighed an average of 257.1 lb after 15 wk of feeding. Pigs fed the diet containing the supplemental DFM were 4 lb heavier (P=0.10) at the end of the experiment compared to control fed pigs (Table 7). This response resulted from faster growth when pigs were fed the DFM supplement compared to control pigs (2.01 vs. 1.93 lb/d, respectively; P<0.03; Table 8). Average daily feed intake (ADFI) was unaffected by dietary treatment (Table 9). This lack of response difference between treatments for feed intake, coupled with greater average daily gain in pigs treated with the DFM, resulted in improved (P<0.08) feed efficiency during the two finisher phases (Phase 4 and 5) and in the overall 15-week trial when pigs were fed the DFM supplemented diet compared to pigs fed the control diet. (Table 10).

TABLE 7

Effects of dietary *Bacillus* direct-fed microbial (DFM) supplementation on pig body weight.

| | Diet | | | P |
|---|---|---|---|---|
| Item | CTL | DFM | MSE | value |
| Body Weight, lb | | | | |
| Initial | 64.30 | 64.73 | 1.21 | 0.17 |
| wk 3 | 97.96 | 98.74 | 2.96 | 0.20 |
| wk 6 | 132.44 | 132.95 | 5.96 | 0.68 |
| wk 9 | 172.07 | 172.6 | 7.74 | 0.74 |
| wk 12 | 212.82 | 215.51 | 10.14 | 0.20 |
| wk 15 | 255.05 | 259.13 | 12.17 | 0.10 |

TABLE 8

Effects of dietary *Bacillus* direct-fed microbial (DFM) supplementation on average daily gain (ADG).

| | Diet | | | P |
|---|---|---|---|---|
| Item | CTL | DFM | MSE | value |
| ADG, lb | | | | |
| wk 0-3 | 1.72 | 1.74 | 0.129 | 0.39 |
| wk 3-6 | 1.64 | 1.63 | 0.224 | 0.78 |
| wk 0-6 | 1.68 | 1.68 | 0.145 | 0.90 |
| wk 6-9 | 1.89 | 1.89 | 0.182 | 0.98 |
| wk 0-9 | 1.75 | 1.75 | 0.123 | 0.91 |
| wk 9-12 | 1.94 | 2.04 | 0.327 | 0.13 |
| wk 0-12 | 1.8 | 2.01 | 0.119 | 0.25 |
| wk 6-12 | 1.91 | 1.97 | 0.198 | 0.20 |
| wk 12-15 | 1.92 | 1.98 | 0.292 | 0.30 |
| wk 0-15 | 1.82 | 1.86 | 0.114 | 0.13 |
| wk 9-15 | 1.93 | 2.01 | 0.176 | 0.03 |

TABLE 9

Effects of dietary *Bacillus* direct-fed microbial (DFM) supplementation on average daily feed intake (ADFI).

| | Diet | | | |
|---|---|---|---|---|
| Item | CTL | DFM | MSE | P value |
| ADFI, lb | | | | |
| wk 0-3 | 3.28 | 3.31 | 0.243 | 0.55 |
| wk 3-6 | 4.56 | 4.46 | 0.432 | 0.24 |
| wk 0-6 | 3.93 | 3.9 | 0.292 | 0.64 |
| wk 6-9 | 5.51 | 5.49 | 0.528 | 0.88 |

TABLE 9-continued

Effects of dietary *Bacillus* direct-fed microbial (DFM) supplementation on average daily feed intake (ADFI).

| | Diet | | | |
|---|---|---|---|---|
| Item | CTL | DFM | MSE | P value |
| wk 0-9 | 4.46 | 4.44 | 0.336 | 0.86 |
| wk 9-12 | 6.41 | 6.21 | 0.75 | 0.21 |
| wk 0-12 | 4.94 | 4.89 | 0.393 | 0.52 |
| wk 6-12 | 5.96 | 5.85 | 0.591 | 0.38 |
| wk 12-15 | 6.65 | 6.78 | 0.646 | 0.325 |
| wk 0-15 | 5.29 | 5.28 | 0.395 | 0.9 |
| wk 9-15 | 6.53 | 6.5 | 0.6 | 0.82 |

TABLE 10

Effects of dietary *Bacillus* direct-fed microbial (DFM) supplementation on feed efficiency (lb body weight gain per lb of feed consumed).

| | Diet | | | |
|---|---|---|---|---|
| Item | CTL | DFM | MSE | P value |
| Gain: Feed | | | | |
| wk 0-3 | 0.536 | 0.535 | 0.036 | 0.86 |
| wk 3-6 | 0.360 | 0.368 | 0.039 | 0.32 |
| wk 0-6 | 0.430 | 0.435 | 0.030 | 0.45 |
| wk 6-9 | 0.345 | 0.347 | 0.032 | 0.80 |
| wk 0-9 | 0.396 | 0.398 | 0.024 | 0.68 |
| wk 9-12 | 0.306 | 0.337 | 0.066 | 0.03 |
| wk 0-12 | 0.367 | 0.377 | 0.028 | 0.06 |
| wk 6-12 | 0.324 | 0.340 | 0.040 | 0.05 |
| wk 12-15 | 0.289 | 0.293 | 0.036 | 0.55 |
| wk 0-15 | 0.347 | 0.355 | 0.022 | 0.08 |
| wk 9-15 | 0.297 | 0.311 | 0.028 | 0.01 |

Hot carcass weights were 4.5 lb heavier (P<0.01) for pigs fed DFM supplemented diets compared to control fed pigs (Table 11). Furthermore, carcass grade premiums tended to be higher (P=0.15) when pigs were supplemented with the DFM. The observed increase in carcass weight from DFM supplementation resulted in $0.39 more carcass value compared to control carcasses.

TABLE 11

Effects of dietary *Bacillus* direct-fed microbial (DFM) supplementation on carcass characteristics.

| | Diet | | | |
|---|---|---|---|---|
| Item | CTL | DFM | MSE | P value |
| Carcass Characteristics | | | | |
| Fat Depth, in | 0.92 | 0.93 | 0.11 | 0.69 |
| Loin Depth, in | 2.94 | 2.92 | 0.09 | 0.34 |
| Lean, % | 54.9 | 54.77 | 0.86 | 0.45 |
| Hot Carcass Wt, lb | 202.7 | 207.2 | 7.84 | 0.01 |
| Carcass Grade Premium | 5.41 | 5.70 | 0.96 | 0.15 |
| Carcass Value ($/cwt) | 94.44 | 94.83 | 1.58 | 0.23 |

Manure nutrient values measured from samples obtained throughout the trial period are reported in Table 12. Dry matter (P=0.20), ash (P=0.11), and ammonium nitrogen (P=0.15) tended to be reduced in manure pits associated with pigs fed the *Bacillus* DFM compared to control pigs. *Bacillus* DFM supplementation decreased dry matter 7%, ash by 8%, and ammonium nitrogen by 5% in manure from treated pigs compared to control. The observed reductions in dry matter and ash excretion may be attributable to improvements in feed efficiency.

TABLE 12

Effects of dietary *Bacillus* direct-fed microbial (DFM) supplementation on nutrient accumulation in the manure pit (g/lb of body weight gain) over the total trial.

| | Diet | | | |
|---|---|---|---|---|
| Item | CTL | DFM | MSE | P value |
| Overall | | | | |
| DM | 296.8 | 276.4 | 36.31 | 0.20 |
| Ash | 55.06 | 50.79 | 5.89 | 0.11 |
| Total N | 19.25 | 18.98 | 2.82 | 0.83 |
| Ammonium N | 14.71 | 13.94 | 1.21 | 0.15 |
| P | 5.65 | 5.29 | 0.73 | 0.26 |
| Ca | 8.50 | 8.03 | 2.09 | 0.63 |

The lack of difference in total nitrogen excretion in manure between treatments suggests that the observed reductions in ammonia nitrogen from the DFM treatment is a result of shifts in the microbial ecology and activity in manure pits associated with DFM treatment compared to control. When expressed as grams per pound of pig body weight, methane gas emissions tended to be reduced (P=0.16; 17% reduction) when pigs were fed the DFM supplemented diets (Table 13). Hydrogen sulfide gas emissions, expressed as grams per pound of pig body weight, were not significantly different from control, but were decreased by 10% when pigs were fed the DFM supplemented diets. Ammonia emissions were numerically lower for DFM fed pigs at all time points. Total methane and hydrogen sulfide gas emissions (grams/day) were reduced (P=0.08) by 14% and 19%, respectively in rooms housing the DFM supplemented pigs compared to control pigs (Table 14).

TABLE 13

Effects of dietary *Bacillus* direct-fed microbial (DFM) supplementation on environmental gas emissions (g/lb of BW gain).

| | Diet | | | |
|---|---|---|---|---|
| Item | CTL | DFM | MSE | P value |
| Overall | | | | |
| $NH_3$ | 4.31 | 4.14 | 0.821 | 0.74 |
| $CO_2$ | 1.36 | 1.37 | 0.137 | 0.97 |
| $CH_4$ | 8.07 | 6.72 | 1.43 | 0.16 |
| $H_2S$ | 0.61 | 0.55 | 0.133 | 0.51 |

TABLE 14

Effects of dietary DFM supplementation on average methane ($CH_4$) and hydrogen sulfide ($H_2S$) gas emissions.[1]

| | Dietary treatment | | | |
|---|---|---|---|---|
| Emissions | Control | Test DFM | SEM | P-value |
| Methane ($CH_4$) | 1072.8 | 922.6 | 47.1 | 0.086 |
| Hydrogen sulfide ($H_2S$) | 95.3 | 77.3 | 7.8 | 0.149 |

[1]Data in g/day; SEM = standard error of the mean.

Total volatile fatty acids (VFA) were reduced (P=0.01) in manure from pigs fed the *Bacillus* DFM supplemented diets compared to manure from control pigs (Table 15). Specifically, this reduction was the result of less production of 1-butyrate (P=0.04), 4-methly-valerate (P=0.05), and propionate (P=0.12) during the anaerobic microbial fermentation in the manure. Conversely, DFM supplementation resulted in increased (P=0.06) butyrate production.

TABLE 15

Effects of dietary DFM supplementation on manure volatile fatty acid (VFA) composition.[1]

| Volatile Fatty Acid (VFA) | Dietary Treatment | | | P-value |
|---|---|---|---|---|
| | Control | DFM | SEM | |
| Acetate | 15.46 | 15.09 | 0.74 | 0.724 |
| Propionate | 6.92 | 5.79 | 0.50 | 0.120 |
| Butyrate | 2.89 | 4.06 | 0.42 | 0.062 |
| I-Butyrate | 1.54 | 1.19 | 0.11 | 0.042 |
| 4-Methyl-Valerate | 16.29 | 11.66 | 1.61 | 0.053 |
| Total VFA | 45.71 | 40.18 | 1.52 | 0.017 |

[1]Data in ppm dry matter weighted by body weight gain.

Data from this experiment indicates that feeding pigs diets supplemented with this *Bacillus* DFM during the growing and finishing production phases results in improved growth rate, feed efficiency, and final hot carcass weight. Supplementation with the DFM also can reduce dry matter, ash, and ammonium N in the manure pit. Furthermore, reductions in methane and hydrogen sulfide emissions from stored swine manure were evident when the *Bacillus* DFM was supplemented to pig diets.

Example 8

Effect of *Bacillus* Direct-Fed Microbial on the Microbial Ecology in Stored Swine Manure Manure pit samples were obtained from the 15-week grow-finish study described in Example 7. Manure samples for microbial analysis were collected at the end of the trial as described previously in Example 7, from each of the two individual pits per room and analyzed individually resulting in a total of 24 observations. Methane producing archaea (Spence et al., 2008) and bacterial groups of interest were enumerated via quantitative polymerase chain reaction (qPCR) analysis (Metzler-Zebeli et al., 2010, Yu et al., 2005). Data were analyzed using one-way ANOVA via Proc Mixed procedure of SAS (v. 9.1.3, SAS Institute, Inc., Cary, N.C.) with significance level $\alpha$=0.10. Trends were declared for $0.20 \geq P > 0.10$.

The addition of the *Bacillus* DFM to swine diets resulted in shifts in microbial populations in stored swine manure. The proteolytic *Clostridium* cluster I group of bacteria was reduced (P<0.01) in stored manure resulting from pigs fed the DFM compared to manure from control pigs (Table 16). Administration of the *Bacillus* DFM to pigs resulted in an increase in the fibrolytic *Clostridium* cluster XIVa (P=0.09) associated with butyrate production. This increase in *Clostridium* cluster XIVa supports the observed increase in butyrate production associated with the DFM treatment, as reported in Table 15 in Example 7. *Bacteroides* and *Prevotella* species, producing a wide variety of VFA, were significantly reduced (P=0.08) in manure from pigs supplemented with the DFM. Methanogens tended to be reduced (P=0.13) in the stored manure from pigs fed the *Bacillus* DFM compared to manure from control pigs, and sulfate reducing bacteria were numerically decreased. The observed reductions in these archaea and sulfate reducing bacteria support the observed decreases in methane and hydrogen sulfide gas production with DFM supplementation documented in Table 13 and Table 14 in Example 7.

TABLE 16

Effects of dietary *Bacillus* direct-fed microbial (DFM) supplementation on microbial populations in stored swine manure.[1]

| Microorganism group | Dietary treatment | | | P-value |
|---|---|---|---|---|
| | Control | DFM | SEM | |
| Methanogens (Archaea) | 0.181 | 0.103 | 0.03 | 0.132 |
| Bacteroides/*Prevotella* | 1.193 | 0.626 | 0.19 | 0.083 |
| *Clostridium* cluster I | 0.386 | 0.079 | 0.04 | 0.002 |
| *Clostridium* cluster IV | 2.551 | 1.200 | 0.62 | 0.176 |
| *Clostridium* cluster XIVa | 3.525 | 4.835 | 0.47 | 0.097 |
| Sulfate-reducing bacteria | 0.027 | 0.017 | 0.01 | 0.379 |

[1]Data in Act relative to total bacteria and adjusted for manure dry matter (DM) and weighted by body weight gain; SEM = standard error of the mean.

Example 9

The Effect of Supplementation of a *Bacillus* Direct-Fed Microbial (DFM) to Pigs Reared in a Commercial Wean-to-Finish Facility and Fed Diets Formulated with a High Level of by-Products and Limited Energy Levels To determine the growth performance of pigs fed commercial corn-soy based diets with increasing amounts of by-product, a wean-to-finish study was conducted. A total of 1024 pigs were weaned at approximately 3 weeks of age, separated by gender and weight category, distributed over 32 pens on trial and phase fed for 105 days. Pigs were weighed every two weeks during the initial three nursery phases. Initial phase diets contained up to 20% corn distiller's grains and solubles (cDDGS). Pigs were continued on two grower phases and one finisher phase lasting 21 days each. The two grower as well as the finisher phase diets contained 35% cDDGS and 15% wheat middlings replacing corn in the diet (Table 17).

TABLE 17

Feeding phases and diet composition.[1]

| | Phase | | | | |
|---|---|---|---|---|---|
| | 1) Early Initial | 2) Late Initial | 3) Early Grower | 4) Late Grower | 5) Early Finish |
| | Duration (Days) | | | | |
| Ingredient (%) | 0-28 | 28-42 | 42-63 | 63-84 | 84-105 |
| Corn | 53.1 | 48.6 | 28.2 | 31.9 | 35.4 |
| SBM (46.5% CP) | 25.0 | 27.2 | 18.2 | 14.5 | 11.3 |
| Spray dried whey | 10.0 | 0.0 | 0.0 | 0.0 | 0.0 |
| Sel. menh. fishmeal | 4.5 | 0.0 | 0.0 | 0.0 | 0.0 |
| cDDGS | 0.0 | 20.0 | 35.0 | 35.0 | 35.0 |
| Wheat Midds | 0.0 | 0.0 | 15.0 | 15.0 | 15.0 |
| Fat | 3.000 | 1.000 | 1.000 | 1.000 | 1.000 |
| MCP (21% P) | 1.200 | 0.800 | 0.000 | 0.000 | 0.000 |
| Limestone (CaCO$_2$) | 0.800 | 1.115 | 1.475 | 1.470 | 1.450 |
| Salt | 0.350 | 0.350 | 0.350 | 0.350 | 0.350 |
| Vitamin premix | 0.150 | 0.150 | 0.090 | 0.090 | 0.075 |
| Mineral premix | 0.125 | 0.125 | 0.125 | 0.125 | 0.085 |
| Lysine HCl | 0.150 | 0.450 | 0.470 | 0.400 | 0.350 |
| DL-Methionine | 0.050 | 0.075 | 0.000 | 0.000 | 0.000 |
| L-Threonine | 0.250 | 0.100 | 0.055 | 0.020 | 0.000 |

TABLE 17-continued

Feeding phases and diet composition.[1]

| | Phase | | | | |
|---|---|---|---|---|---|
| | 1) Early Initial | 2) Late Initial | 3) Early Grower | 4) Late Grower | 5) Early Finish |
| | Duration (Days) | | | | |
| Ingredient (%) | 0-28 | 28-42 | 42-63 | 63-84 | 84-105 |
| Phyzyme 2500TPT | 0.020 | 0.020 | 0.020 | 0.020 | 0.020 |
| ZincOxide | 0.350 | 0.000 | 0.000 | 0.000 | 0.000 |
| Mecadox 2.5 | 1.000 | 0.500 | 0.000 | 0.000 | 0.000 |

[1]SBM, soybean meal; CP, crude protein; cDDGS, corn dried distiller's grains with solubles with ~10% oil content; treatment included to the expense of corn.

Diets were formulated to simulate standard commercial diets with excess crude protein but limited energy. Except for the first 6 weeks of trial, no antibiotic growth promoters were fed. Treatment consisted of direct-fed microbial (DFM) supplementation compared to control diet without DFM. The direct-fed microbial consisted of equal proportions of *Bacillus subtilis* strains AGTP BS918 (NRRL B-50508), AGTP BS1013 (NRRL B-50509) and AGTP BS3BP5 (NRRL B-50510) summing to a guaranteed $3.0 \times 10^8$ cfu/g of DFM product, included at a rate of 1 lb/ton in feed, resulting in a concentration of $1.5 \times 10^5$ cfu/g in the diet. Growth performance and losses were analyzed using Proc Mixed procedure of SAS (v. 9.1.3, SAS Institute, Inc., Cary, N.C.) with significance level $\alpha=0.10$. Trends were declared for $0.15 \geq P > 0.10$. Data was blocked for gender and weight category and balanced for initial weight.

Average daily gain of pigs fed the DFM was greater ($P<0.05$) from d 0 to 14 and d 14 to 28 of the trial compared to control pigs (Table 18), which resulted in a greater ($P<0.05$) body weight of DFM supplemented pigs on d 14 and d 28 of the study (Table 19). This increase in body weight gain exhibited by the DFM supplemented pigs was a result of greater ($P<0.10$) average daily feed intake during the d 0 to 14 and d 0 14 to 28 periods (Table 20). Feed efficiency was also improved ($P=0.03$) during the first two week period of the trial (Table 20b).

TABLE 18

Average daily gain (adg) over the duration of the study.

| | Control | DFM | SEM | P-Value |
|---|---|---|---|---|
| adg0-14 | 0.419 | 0.474 | 0.012 | 0.003 |
| adg14-28 | 1.067 | 1.133 | 0.022 | 0.041 |
| adg28-42 | 1.414 | 1.370 | 0.022 | 0.169 |
| adg0-42 | 0.967 | 0.992 | 0.016 | 0.268 |
| adg42-63 | 1.798 | 1.837 | 0.016 | 0.097 |
| adg63-84 | 1.996 | 1.964 | 0.024 | 0.335 |
| adg42-84 | 1.897 | 1.900 | 0.012 | 0.857 |
| adg0-84 | 1.432 | 1.446 | 0.013 | 0.432 |
| adg84-105 | 1.994 | 2.045 | 0.016 | 0.027 |
| adg42-105 | 1.447 | 1.461 | 0.007 | 0.150 |
| adg0-105 | 1.287 | 1.305 | 0.009 | 0.143 |

[1]SEM = standard error of the mean.

TABLE 19

Pig body weight (lb) and percent health loss (mortality and culls) throughout the duration of the study.

| | Control | DFM | SEM[1] | P-Value |
|---|---|---|---|---|
| d0 | 13.46 | 13.57 | 0.19 | 0.699 |
| d14 | 19.38 | 20.23 | 0.29 | 0.051 |

TABLE 19-continued

Pig body weight (lb) and percent health loss (mortality and culls) throughout the duration of the study.

| | Control | DFM | SEM[1] | P-Value |
|---|---|---|---|---|
| d28 | 34.32 | 36.09 | 0.54 | 0.027 |
| d42 | 54.11 | 55.27 | 0.79 | 0.308 |
| d63 | 91.87 | 93.84 | 0.96 | 0.155 |
| d84 | 133.80 | 135.08 | 1.19 | 0.447 |
| d105 | 175.67 | 178.03 | 1.18 | 0.167 |
| % mortality | 2.95 | 1.37 | 0.61 | 0.076 |

[1]SEM = standard error of the mean.

TABLE 20

Average daily feed intake (adfi) over the duration of the study.

| | Control | DFM | SEM | P-Value |
|---|---|---|---|---|
| adfi0-14 | 0.624 | 0.671 | 0.013 | 0.017 |
| adfi14-28 | 1.634 | 1.726 | 0.038 | 0.102 |
| adfi28-42 | 2.544 | 2.510 | 0.045 | 0.600 |
| adfi0-42 | 1.601 | 1.636 | 0.028 | 0.385 |
| adfi42-63 | 3.747 | 3.873 | 0.049 | 0.077 |
| adfi63-84 | 5.061 | 5.044 | 0.053 | 0.823 |
| adfi42-84 | 4.404 | 4.459 | 0.043 | 0.373 |
| adfi0-84 | 3.002 | 3.047 | 0.032 | 0.322 |
| adfi84-105 | 6.191 | 6.099 | 0.048 | 0.180 |
| adfi42-105 | 3.750 | 3.754 | 0.028 | 0.912 |
| adfi0-105 | 3.034 | 3.048 | 0.026 | 0.691 |

[1]SEM = standard error of the mean.

TABLE 20b

Feed conversion (feed: gain, fg) over the duration of the study.

| | Control | DFM | SEM | P-Value |
|---|---|---|---|---|
| fg0-14 | 1.499 | 1.424 | 0.024 | 0.038 |
| fg14-28 | 1.533 | 1.524 | 0.021 | 0.769 |
| fg28-42 | 1.801 | 1.831 | 0.019 | 0.255 |
| fg0-42 | 1.611 | 1.593 | 0.010 | 0.235 |
| fg42-63 | 2.082 | 2.108 | 0.022 | 0.408 |
| fg63-84 | 2.539 | 2.571 | 0.032 | 0.486 |
| fg42-84 | 2.311 | 2.340 | 0.018 | 0.258 |
| fg0-84 | 1.961 | 1.966 | 0.011 | 0.721 |
| fg84-105 | 3.107 | 2.982 | 0.031 | 0.008 |
| fg42-105 | 1.932 | 1.915 | 0.013 | 0.369 |
| fg0-105 | 1.825 | 1.808 | 0.010 | 0.222 |

[1]SEM = standard error of the mean.

Direct-fed microbial supplementation resulted in greater ($P<0.10$) ADG and ADFI during the early grower phase (d 42 to 63 of the trial). During the finisher phase of the trial, ADG was greater ($P=0.02$) from d 84 to 105 when pigs were fed diets supplemented with the DFM compared to control pigs, and tended to be greater ($P=0.14$) for the overall d 0 to 105 time period. The improved ADG response with DFM treatment from d 84 to 105 and lack of ADFI response, resulted in improved ($P<0.01$) feed conversion during this period. The improvements in ADG from DFM supplementation throughout the trial resulted in about a 3 pound heavier pig at the end of the study (d 105) compared to control pigs (Table 19). Furthermore, health losses due to mortality and culls as a result of flu, *Streptococcus suis* infection, etc. were reduced ($P=0.07$; Table 19).

Example 10

The Effect of Supplementation of a Bacillus Direct-Fed Microbial (DFM) to Pigs Reared in a Commercial Wean-to-Finish Facility and Fed Diets Formulated with a High Level of by-Products and Limited Energy Levels on Efficiency of Feed Conversion The effect of a Bacillus direct-fed microbial on the efficiency of feed utilization by pigs, which are reared in a wean-to-finish facility, was assessed. A total of 2160 pigs were weaned at approximately 3 weeks of age, separated by gender, balanced for initial weight, and distributed over 68 pens in two rooms at the same site on trial. Animals were phase fed for 105 days. Pigs were weighed every two weeks during the initial nursery phase lasting until day 42, post-weaning. Initial phase diets contained up to 20% corn distiller's grains and solubles (cDDGS). Pigs were continued on trial through two grower phases and one finisher phase, each 21 days. The grower as well as the finisher phase diets contained 35 cDDGS and 15% wheat middlings replacing corn in the diet (Table 21). Diets were formulated to simulate standard commercial diets with limited crude protein and energy.

TABLE 21

Feeding phases and diet composition.[1]

| | Phase | | | | |
|---|---|---|---|---|---|
| | 1) Early Initial | 2) Late Initial | 3) Early Grower | 4) Late Grower | 5) Early Finish |
| | | | Duration (days) | | |
| Ingredient (%) | 0-28 | 28-42 | 42-63 | 63-84 | 84-105 |
| Corn | 46.5 | 49.6 | 36.7 | 39.6 | 41.5 |
| SBM (46.5% CP) | 37.0 | 27.0 | 10.0 | 7.0 | 5.0 |
| Spray dried whey | 10.0 | — | — | — | — |
| Spray dried plasma | 2.2 | — | — | — | — |
| cDDGS | — | 20.0 | 35.0 | 35.0 | 35.0 |
| Wheat Midds | — | — | 15.0 | 15.0 | 15.0 |
| Fat | 2.000 | 1.000 | 1.000 | 1.000 | 1.000 |
| MCP (21% P) | 0.800 | — | — | — | — |
| Limestone (CaCO$_2$) | 0.800 | 1.000 | 1.350 | 1.350 | 1.350 |
| Salt | 0.350 | 0.350 | 0.350 | 0.350 | 0.350 |
| Vitamin premix | 0.150 | 0.150 | 0.090 | 0.090 | 0.075 |
| Mineral premix | 0.125 | 0.125 | 0.125 | 0.125 | 0.085 |
| Lysine HCl | — | 0.250 | 0.350 | 0.450 | 0.550 |
| DL-Methionine | 0.080 | 0.060 | 0.020 | 0.010 | 0.030 |
| L-Threonine | — | 0.100 | 0.020 | 0.060 | 0.100 |
| ZincOxide | 0.350 | — | — | — | — |
| Mecadox 2.5 | 0.400 | 0.400 | — | — | — |
| TOTAL | 100.0 | 100.0 | 100.0 | 100.0 | 100.0 |

[1]SBM, soybean meal; CP, crude protein; cDDGS, corn dried distiller's grains with solubles with ~10% oil; treatment included to the expense of corn.

With the exception of the first 6 weeks of trial, no antibiotic growth promoters were fed. Treatments consisted of direct-fed microbial (DFM) supplementation compared to a control diet without DFM. The direct-fed microbial consisted of equal proportions of Bacillus subtilis strains AGTP BS918 (NRRL B-50508), AGTP BS1013 (NRRL B-50509) and AGTP BS3BP5 (NRRL B-50510) summing to a guaranteed 3.0×10$^8$ cfu/g of DFM product, included at a rate of 1 lb/ton in feed, resulting in a concentration of 1.5×10$^5$ cfu/g in the diet. Feed conversion was analyzed using Proc Mixed procedure of SAS (v. 9.1.3, SAS Institute, Inc., Cary, N.C.) with significance level α=0.10. Trends were declared for 0.15≥P>0.10. Data were blocked for room and gender for analysis.

Less (P=0.02) feed was required per pound of body weight gain from d 0 to 14 of the trial when pigs were fed diets containing the Bacillus DFM supplement, and this feed efficiency response tended (P=0.13) to be evident over the entire nursery phase from d 0 to 42 of the study. (Table 22). Direct-fed microbial supplementation also improved (P=0.08) feed efficiency during the finishing phase (d 84 to 105).

TABLE 22

Feed conversion (feed: gain, fg) over the duration of the study.

| | Control | DFM | SEM | P-value |
|---|---|---|---|---|
| fg0-14 | 1.599 | 1.455 | 0.045 | 0.027 |
| fg14-28 | 1.360 | 1.389 | 0.015 | 0.191 |
| fg28-42 | 1.674 | 1.656 | 0.011 | 0.267 |
| fg0-42 | 1.537[)] | 1.520 | 0.008 | 0.134 |
| fg42-63 | 2.020 | 2.015 | 0.009 | 0.707 |
| fg63-84 | 2.311 | 2.336 | 0.016 | 0.267 |
| fg42-84 | 2.177 | 2.187 | 0.009 | 0.445 |
| fg0-84 | 1.960 | 1.957 | 0.007 | 0.797 |
| fg84-105 | 2.740 | 2.677 | 0.025 | 0.081 |
| fg42-105 | 2.376 | 2.361 | 0.010 | 0.294 |

[1]SEM = standard error of the mean.

Example 11

The Effect of Supplementation of a Bacillus Direct-Fed Microbial (DFM) on Feed Efficiency Response of Nursery Pigs Fed Diets Formulated with a High Levels of Fibrous by-Products A total of 480 pigs (initial body weight: approximately 6.0 kg) were weaned at 21 days of age and penned 10 pigs/pen in an environmentally controlled nursery pig facility. Pigs were placed on test from 21 days of age to 63 days of age and fed a two phase feeding program with diets formulated based on corn, soybean meal, and 40% corn DDGS (Table 23) and to meet the nutrient requirements of pigs at each of the two production phases (Table 24).

TABLE 23

Basal diet composition of Phase 1 and 2 nursery pig diets.

| | Nursery Diet: | |
|---|---|---|
| | NC - Nursery 1 | NC - Nursery 2 |
| | Body Weight, lb | |
| Ingredient, % in diet | 15 to 25 | 25 to 45 |
| Corn, yellow dent | 38.66 | 43.76 |
| Corn DDGS | 20 | 20 |
| Soybean meal, 46.5% CP | 27.2 | 27.2 |
| Wheat middlings, <9.5% fi | 5 | 5 |
| Fish meal, menhaden | 2 | 0 |
| Whey, dried | 3 | 0 |
| Choice white grease | 1 | 1 |
| Dicalcium phosphate 18.5% | 0.4 | 0.35 |
| Limestone | 1.08 | 1.16 |
| Salt | 0.3 | 0.3 |
| NSNG Nursery Vit. Premix | 0.5 | 0.5 |
| L-lysine HCl | 0.53 | 0.48 |
| DL-methionine | 0.16 | 0.12 |
| L-threonine | 0.17 | 0.13 |
| L-tryptophan | 0.01 | 0.01 |

TABLE 24

Calculated composition of basal diets, %.

|  | Phase 1 (15 to 25 lb) | Phase 2 (25 to 45 lb) |
|---|---|---|
| Dry Matter % | 89.73 | 89.45 |
| DE - kcal/lb. | 1604.2 | 1603.43 |
| ME - kcal/lb. | 1520.6 | 1523.19 |
| NE - kccal/lb. | 1078 | 1078.46 |
| Crude Protein % | 24.47 | 23.18 |
| Lys % | 1.45 | 1.31 |
| Thr % | 0.91 | 0.82 |
| Met % | 0.52 | 0.45 |
| Met + Cys % | 0.84 | 0.77 |
| Trp % | 0.24 | 0.22 |
| Calcium % | 0.74 | 0.64 |
| Phos. % - total | 0.63 | 0.55 |
| Phos. % - available | 0.33 | 0.25 |
| Phos. % - digestible | 0.32 | 0.25 |

All diets contained phytase (500 FTU/kg feed). One of three dietary treatments was randomly assigned to pens such that each treatment was represented by eight replicate pens. Treatments consisted of direct-fed microbial (DFM) supplementation at two levels of inclusion (0.5 and 1.0 lb/ton of feed) compared to a control diet without the DFM supplement (Table 25).

The direct-fed microbial consisted of equal proportions of *Bacillus subtilis* strains AGTP BS918 (NRRL B-50508), AGTP BS1013 (NRRL B-50509) and AGTP BS3BP5 (NRRL B-50510) summing to a guaranteed $3.0 \times 10^8$ cfu/g of DFM product, included at a rate of 0.5 or 1.0 lb/ton of feed resulting in a concentration of $7.5 \times 10^4$ cfu/g or $1.5 \times 10^5$ cfu/g in the diet, respectively. Pig body weight gain and pen feed intake were determined on d 21 and d 42 of the trial to calculate feed efficiency as gain:feed. Feed efficiency may also be calculated as feed:gain.

TABLE 25

Dietary treatments and DFM inclusion rates

| Treatment | Diet | Processing condition[1] | DFM Inclusion rate, lb/ton | Phyzyme XP, FTU/kg[2] |
|---|---|---|---|---|
| T-1 | Control | mash | 0.0 | 500 |
| T-2 | Control + DFM | Mash | 0.5 | 500 |
| T-3 | Control + DFM | Mash | 1.0 | 500 |

[1]Diets were processed as mash, unpelleted feed.
[2]All diets contained 500 FTU/kg feed of Phytase.

Pigs fed the *Bacillus* DFM treated diets had greater (P=0.03) body weight gain per unit of feed intake compared to the pigs fed the control diet during the early nursery phase (d 0 to 21, post-weaning; Table 26).

TABLE 26

Body weight and feed efficiency of nursery pigs fed high-fibre-based diets supplemented with a *Bacillus* DFM at two inclusion levels in the diet.

| | Phytase, FTU/kg | | | | |
|---|---|---|---|---|---|
| | 500 | 500 | 500 | | |
| | *Bacillus* DFM, lb/ton | | | | |
| | 0 | 0.5 | 1.0 | | |
| | Diet | | | | |
| | 1 | 3 | 4 | SEM | P value |
| Body weight, kg | | | | | |
| Initial | 6.79 | 6.79 | 6.79 | 0.021 | 0.378 |
| day 21 | 11.60 | 11.92 | 11.93 | 0.135 | 0.270 |
| day 42 | 26.0 | 26.7 | 26.5 | 0.38 | 0.482 |
| Gain: Feed | | | | | |
| day 0_21 | 0.656b | 0.721a | 0.729a | 0.0192 | 0.039 |
| day 21_42 | 0.655 | 0.661 | 0.641 | 0.0124 | 0.808 |
| day 0_42 | 0.651 | 0.675 | 0.662 | 0.0106 | 0.286 |
| N, Pens*/Diet | 8 | 8 | 8 | | |

*Pigs per pen = 10

Example 12

Effect of a *Bacillus* Direct Fed Microbial on Energy and Nutrient Digestibility in Growing Pigs Fed Diets Containing 40% Corn DDGS A digestibility study was conducted on growing pigs to measure the effects of a *Bacillus* direct-fed microbial (DFM) on ileal and total tract digestibilities of energy and nutrients in diets containing 40% corn dried distillers grains including solubles (DDGS). Twenty four pigs (initial BW: approximately 25 kg) originating from the matings of G-Performer boars to F-25 females (Genetipore, Alexandria, Minn.) were surgically equipped with a T-cannula in the distal ileum. Following surgeries, pigs were allowed 21 d to recuperate. A standard corn-soybean meal based diet was provided on an ad libitum basis during this period. Three weeks after surgery, pigs were allotted to two dietary treatments consisting of a control basal diet and a *Bacillus* DFM. Pigs were housed in individual pens (1.2×1.5 m) in an environmentally controlled room. Each pen was equipped with a feeder and a nipple drinker and had fully slatted concrete floors The experimental basal diet was formulated based on corn, soybean meal, and 40% corn DDGS (Table 27). The dietary treatments were: (1) a basal diet with no DFM; or (2) the basal diet with 0.05% DFM added at the expense of cornstarch. The direct-fed microbial consisted of equal proportions of *Bacillus subtilis* strains AGTP BS918 (NRRL B-50508), AGTP BS1013 (NRRL B-50509) and AGTP BS3BP5 (NRRL B-50510) summing to a guaranteed $3.0 \times 10^8$ cfu/g of DFM product, included at a rate of 1.0 lb/ton of feed resulting in a concentration of $1.5 \times 10^5$ cfu/g in the diet. All diets were formulated to meet or exceed the nutrient requirements for growing pigs (NRC, 1998).

TABLE 27

Composition of experimental basal diet[1]

| Ingredient, % | |
|---|---|
| Corn | 32.60 |
| DDGS | 40.00 |

TABLE 27-continued

Composition of experimental basal diet[1]

| | |
|---|---|
| Wheat middlings | 10.00 |
| SBM, 48% CP | 14.00 |
| Cornstarch | 0.60 |
| Limestone | 1.30 |
| Lysine HCl | 0.40 |
| Salt | 0.40 |
| Titanium dioxide | 0.40 |
| Vitamin-mineral premix[3] | 0.30 |
| Total | 100.00 |
| Calculated composition, % | |
| CP (N × 6.25) | 21.9 |
| ME, kcal/kg | 3,295 |
| SID Lys | 1.19 |
| ADF | 8.7 |
| NDF | 14.9 |
| Ca | 0.64 |
| Total P | 0.59 |
| Digestible P | 0.29 |

[1]Direct-fed microbial treatment was added at 0.05% of the diet at the expense of cornstarch.
[3]The vitamin-micromineral premix provided the following quantities of vitamins and minerals per kilogram of complete diet: Vitamin A, 10,990 IU; vitamin $D_3$, 1,648 IU; vitamin E, 55 IU; vitamin K, 4.4 mg; thiamin, 3.3 mg; riboflavin, 9.9 mg; pyridoxine, 3.3 mg; vitamin $B_{12}$, 0.044 mg; D-pantothenic acid, 33 mg; niacin, 55 mg; folic acid, 1.1 mg; biotin, 0.17 mg; Cu, 16 mg as copper sulfate; Fe, 165 mg as iron sulfate; I, 0.36 mg as potassium iodate; Mn, 44 mg as manganese sulfate; Se, 0.3 mg as sodium selenite; Zn, 165 mg as zinc oxide.

Titanium dioxide was used as an indigestible marker in all diets. The diets were fed to the 12 pigs, providing 6 pigs per diet for 17 days. Pigs were allowed ad libitum intake of diets and water throughout the experiment. To minimize cross contamination of control pens with DFM, pens fed diets without DFM were fed first followed by DFM-treated pens. After feeding each treatment, feed delivery carts were completely cleaned. Pigs fed diets without DFM were also weighed and collected first before pigs fed DFM-containing diets.

Fecal samples were collected on d 12 via grab sampling and ileal samples were collected on d 13 and 14. Ileal samples were collected continuously for 9 h starting at 0800 on each collection day. Cannulas were opened and 225-mL plastic bags were attached to the cannula barrel using cable ties, which allowed digesta to flow from the cannula to the bag. Bags were changed whenever filled with digesta or at least once every 30 min. The pH in the digesta was measured in the first bag collected after 0900, 1100, 1300 and 1500 on each collection day. Following the final ileal collection, pigs were fed their respective experimental diets for 3 additional days. The morning meal (at 0700) that is fed on the day following the last ileal collection contained a green marker. During the following 36 h, ileal digesta and feces were scored every 30 min from all pigs, and the first time the marker appears at any of these sites were recorded and used as a measure of rate of passage for this particular diet.

At the conclusion of the experiment, samples were thawed and mixed within animal and diet and a sub-sample was collected for chemical analysis. All samples were lyophilized and ground prior to analysis. All samples were also analyzed for dry matter (DM), acid detergent fiber (ADF), neutral detergent fiber (NDF), and lignin.

Values for apparent ileal (AID) and total tract (ATTD) digestibility of nutrients were calculated as described previously (Stein et al., 2007). Homogeneity of variances was confirmed and outliers were tested using the UNIVARIATE procedure (SAS Institute Inc., Cary, N.C.). No outliers were detected. Data were analyzed using the MIXED procedure. The model included dietary treatment as fixed effect whereas pig was the random effect. Least square means were calculated for each independent variable. The pig was the experimental unit for all calculations, and the a level used to determine significance and tendencies between means was 0.05 and ≤0.10, respectively.

Ileal pH was lower (P=0.03) in pigs fed the diet containing the Bacillus DFM compared to the ileal pH of control pigs (Table 28). Rate of passage and fecal pH were not affected by dietary treatment. Although ADF and NDF were not affected, the addition of the Bacillus DFM to the diet resulted in improved (P<0.03) AID (Table 29) and ATTD (Table 30) of lignin compared to the control diet.

These data indicate the Bacillus DFM lowers the pH of ileal digesta and improves the digestibility of lignin in high fibrous, by-product based diets.

TABLE 28

Effect of Bacillus DFM on pH and rate of passage of ileal digesta and feces in growing pigs fed corn-soybean meal diets containing 40% DDGS[1]

| Item | Control | Bacillus DFM | SEM | P value |
|---|---|---|---|---|
| pH | | | | |
| Ileal digesta | 6.78 | 6.64 | 0.04 | 0.03 |
| Feces | 6.05 | 6.14 | 0.08 | 0.48 |
| Rate of passage, h | | | | |
| Ileal digesta | 5.29 | 4.82 | 0.25 | 0.19 |
| Feces | 30.67 | 29.29 | 1.03 | 0.36 |

TABLE 29

Effect of Bacillus DFM on apparent ileal digestibility (AID, %) of fibrous nutrients in growing pigs fed corn-soybean meal diets containing 40% DDGS[1]

| | Control | Bacillus DFM | SEM | P value |
|---|---|---|---|---|
| ADF | 10.0 | 6.5 | 2.6 | 0.35 |
| NDF | 25.4 | 19.7 | 2.7 | 0.80 |
| Lignin | 30.9 | 37.0 | 1.8 | 0.02 |

[1]Data are least squares means of 6 observations for all treatments.

TABLE 30

Effect of Bacillus DFM on apparent total tract digestibility (ATTD, %) of fibrous nutrients in growing pigs fed corn-soybean meal diets containing 40% DDGS[1]

| | Control | Bacillus DFM | SEM | P value |
|---|---|---|---|---|
| ADF | 32.4 | 32.8 | 2.5 | 0.92 |
| NDF | 42.2 | 39.3 | 2.3 | 0.39 |
| Lignin | 10.4 | 28.5 | 3.0 | <0.001 |

[1]Data are least squares means of 6 observations for all treatments.

Example 13

Anti-Inflammatory Effects of Bacillus Strains in a Chicken HD11 Macrophage Cell Line The chicken macrophage cell line HD11 was used to determine the inflammatory response to LPS and determine the potential of direct-fed microbial Bacillus strains to alleviate inflammation associated with a gram negative bacterial infection. Bacillus strains were screened in a cell culture assay to determine changes in inflammatory cytokine gene expression responses to LPS and each of the Bacillus strains (Bacillus subtilis AGTP BS1013 (NRRL B-50509), Bacillus subtilis AGTP BS3BP5 (NRRL B-50510), and *Bacillus subtilis* AGTP BS944 (NRRL B-50548).

Figure 22:
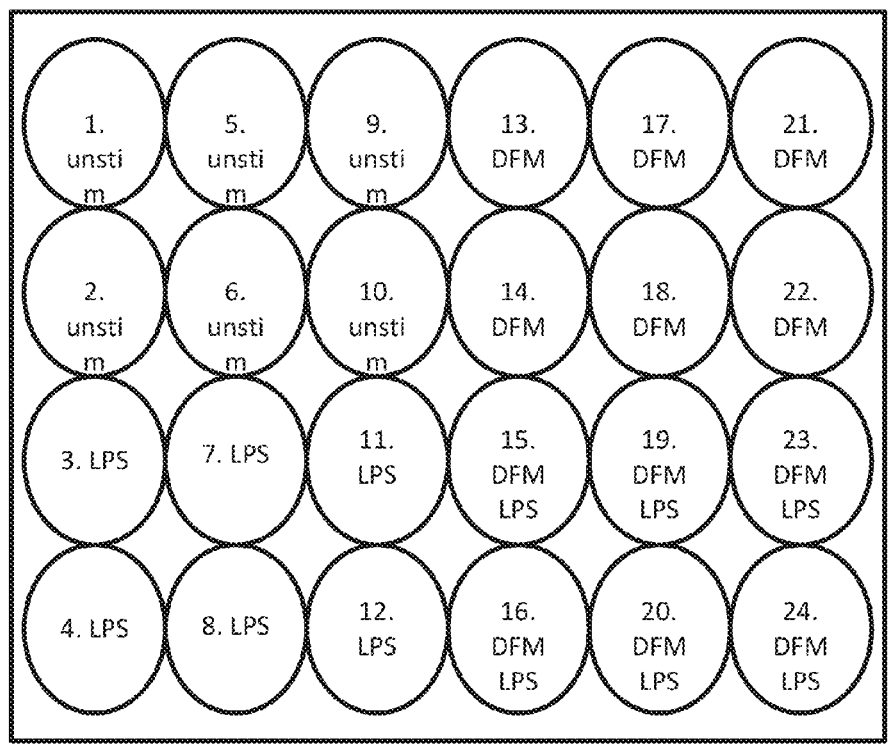
FIG. 22 is a representative schematic of a cell culture plate design for screening *Bacillus* strains for anti-inflammatory effects. LPS was used to induce the inflammatory response but any agent that induces the inflammatory response may be used.

HD11 cells were incubated either: (1) alone (unstimulated); (2) with LPS; (3) with each *Bacillus* strain, and (4) with LPS+*Bacillus* strain. The plate template design is illustrated in FIG. 22.

HD11 cells were grown to confluence and plated in 24-well tissue culture plates with antibiotic free Roswell Park Memorial Institute 1640 (RPMI) media containing 10% fetal bovine serum (FBS; Atlanta Biologicals, Inc., Lawrenceville, Ga.). Once confluent, media was removed and the treatments were administered in antibiotic free media and were then incubated for 1 hour at 41° C. After the incubation, cells were washed twice with PBS and were incubated in 380 µL TRIzol (Invitrogen, Life Technologies Corp., Carlsbad, Calif.) for 5 minutes. Samples were removed from plates, placed in 2 mL microcentrifuge tubes, snap frozen, and stored at −80° C. until RNA isolation. To separate RNA from the organic phase, 2 ml heavy phase lock gel tubes were used (Five Prime, Inc., Gaithersburg, Md.). RNA cleanup was done using the RNeasy mini kit (Qiagen, Inc., Valencia, Calif.) and DNase digestion was done using the RNase-Free DNase kit (Qiagen). cDNA was synthesized using the qScript cDNA SuperMix (VWR, Radnor, Pa.) immediately following the RNA isolation.

Real-time PCR was used to determine gene expression of the HD11 cells using primer sets displayed in Table 31. β-actin was used as a reference gene. One-way ANOVA was performed using Proc Mixed procedure of SAS (v. 9.1.3, SAS Institute, Inc., Cary, N.C.). Means were separated by Student-Newman-Keuls test, significance level $\alpha=0.10$.

TABLE 31

Chicken specific primer sets used in screening assay

| Primer Name | Primer Sequence | PCR Product (bp) |
|---|---|---|
| IL-1β | F: 5'-AGGTCAACATCGCCACCTAC-3' (SEQ ID NO. 7) R: 5'-CAACGGGACGGTAATGAAAC-3' (SEQ ID NO. 8) | 196 |
| IL-8 | F: 5'-GCTCTGTCGCAAGGTAGGAC-3' (SEQ ID NO. 9) R: 5'-GGCCATAAGTGCCTTTACGA-3' (SEQ ID NO. 10) | 231 |
| β-actin | F: 5'-ATGAAGCCCAGAGCAAAAGA-3' (SEQ ID NO. 11) R: 5'-GGGGTGTTGAAGGTCTCAAA-3' (SEQ ID NO. 12) | 223 |

Figure 23:
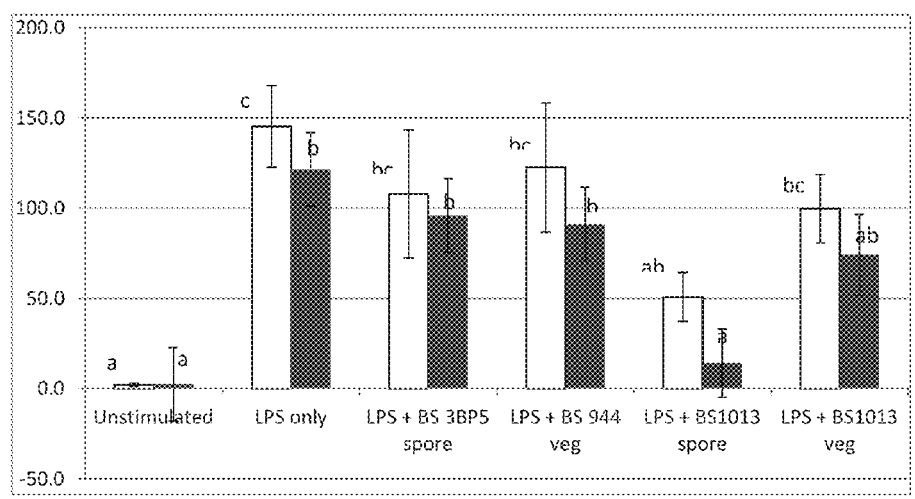
FIG. 23 is a bar graph depicting the anti-inflammatory effects of *Bacillus* strains as shown in a representative macrophage cell line (chicken HD11). The agent used to induce the inflammatory response was LPS. The effects on IL-1β gene expression are shown by the white bars (P<0.01). The effects on IL-8 gene expression are shown by the black bars (P<0.01). Differing letters (a, b, c) indicate means differ statistically (P<0.01).

Lipopolysaccharide challenge in the HD11 chicken macrophage cell line resulted in an increase (P<0.01) in gene expression of the inflammatory cytokines, Interleukin (IL)-1β and IL-8, compared to unstimulated HD11 cells (FIG. 23). When strain AGTP BS1013 was added to the HD11 cells with LPS in spore state, this *Bacillus* strain decreased (P<0.01) the gene expression of the inflammatory cytokines, IL-1β and IL-8, resulting from the administration of LPS alone and was more similar to the gene expression profile of unstimulated HD11 cells. Furthermore, chicken cell response to LPS in presence of vegetative *Bacillus* strain BS1013 was numerically lower, as were *Bacillus* strain AGTP BS3BP5 in spore state, and the spores and vegetative cells of *Bacillus* strain AGTP BS944.

These data demonstrate the efficacy of *Bacillus* DFM strains for alleviating inflammation associated with a bacterial infection, and their effectiveness in avian species. The *Bacillus* DFM strains can be used to alleviate macrophage inflammation. In addition, the *Bacillus* DFM strains can be used to alleviate gram negative bacterial infections, and the effects of these bacterial infections.

Example 14

Anti-Inflammatory Effects of *Bacillus* Strains in a Rat Intestinal Epithelial Cell Line (IEC-6)

The rat intestinal epithelial cell line IEC-6 was used to determine the inflammatory response to LPS and determine the potential of direct-fed microbial *Bacillus* strains to alleviate inflammation associated with a gram negative bacterial infection. *Bacillus* strains were screened in a cell culture assay to determine changes in inflammatory cytokine gene expression responses to LPS and each of the *Bacillus* strains (*Bacillus subtilis* AGTP BS1013 (NRRL B-50509), *Bacillus subtilis* AGTP BS3BP5 (NRRL B-50510), and *Bacillus subtilis* AGTP BS944 (NRRL B-50548), *Bacillus subtilis* AGTP BS1069 (NRRL B-50544), *Bacillus subtilis* AGTP BS 442 (NRRL B-50542), *Bacillus subtilis* AGTP BS521 (NRRL B-50545), and *Bacillus subtilis* AGTP BS918 (NRRL B-50508)). Additional *Bacillus* strains could be used including but not limited to *Bacillus pumilus* AGTP BS1068, (NRRL B-50543) and *Bacillus pumilus* KX11-1 (NRRL B-50546).

Figure 24:
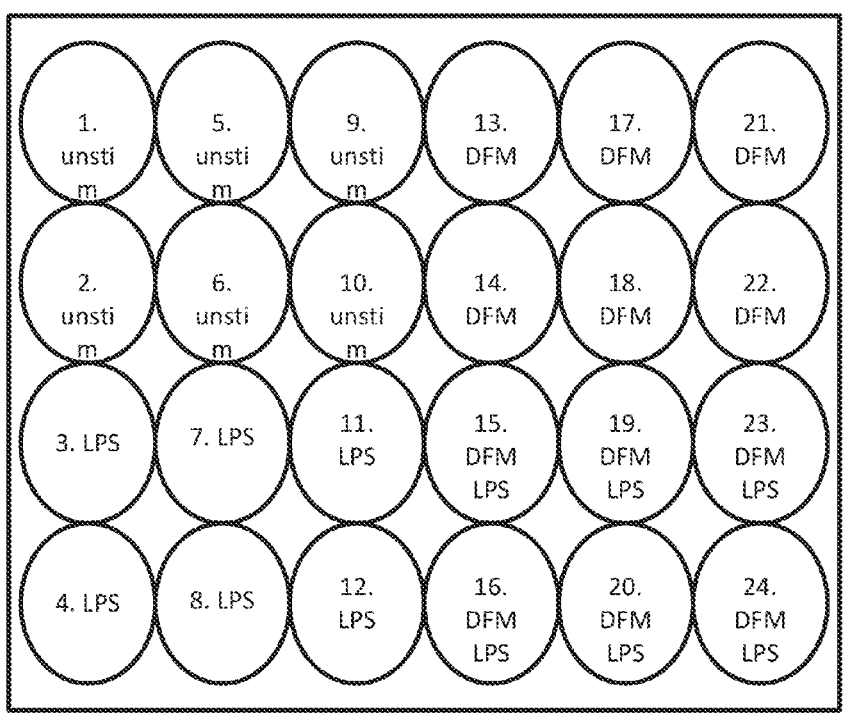
FIG. 24 is a representative schematic of a plate design for cell culture screening for a candidate direct-fed microbial. LPS was used as the agent to induce the inflammatory response.

IEC-6 cells were incubated either: (1) alone (unstimulated); (2) with LPS; (3) with each DFM *Bacillus* strain, and (4) with LPS+*Bacillus* strain. The plate template design is illustrated in FIG. 24.

IEC-6 cells were grown to confluence and plated in 24-well tissue culture plates with Dulbecco's Modified Eagle's Medium (DMEM) (Invitrogen, Life Technologies Corp., Carlsbad, Calif.) containing 10% FBS (Atlanta Biologicals, Inc., Lawrenceville, Ga.) and 1% antibiotic-antimycotic (Atlanta Biologicals). Once the plates were confluent, IEC-6 cells were washed three times with phosphate buffered saline (PBS). The treatments were administered in antibiotic free media and were then incubated for 1 hour at 37° C. After the incubation, cells were washed twice with PBS and were incubated in 380 µL TRIzol (Invitrogen) for 5 minutes.

Samples were removed from plates, placed in 2 mL microcentrifuge tubes, snap frozen, and stored at −80° C. until RNA isolation. To separate RNA from the organic phase, 2 ml heavy phase lock gel tubes were used (Five Prime, Inc., Gaithersburg, Md.). RNA cleanup was done using the RNeasy mini kit (Qiagen, Inc., Valencia, Calif.) and DNase digestion was done using the RNase-Free DNase kit (Qiagen). cDNA was synthesized using the qScript cDNA SuperMix (VWR, Radnor, Pa.) immediately following the RNA isolation.

Real-time PCR was used to determine gene expression of the IEC-6 cells using primer sets displayed in Table 32. β-actin was used as a reference gene. One-way ANOVA was performed using Proc Mixed procedure of SAS (v. 9.1.3, SAS Institute, Inc., Cary, N.C.). Means were separated by Student-Newman-Keuls test, significance level $\alpha=0.10$.

TABLE 32

Rat specific primer sets used in screening assay.

| Primer Name | Primer Sequence | PCR Product (bp) |
|---|---|---|
| TNF-α | F: 5'-GGCAGCCTTGTCCCTTGAAGAG-3' (SEQ ID NO. 13) R: 5'-GTAGCCCACGTCGTAGCAAACC-3' (SEQ ID NO. 14) | 171 |
| β-actin | F: 5'-TGACGAGGCCCAGAGCAAGA-3' (SEQ ID NO. 15) R: 5'-ATGGGCACAGTGTGGGTGAC-3' (SEQ ID NO. 16) | 331 |

Figure 25:
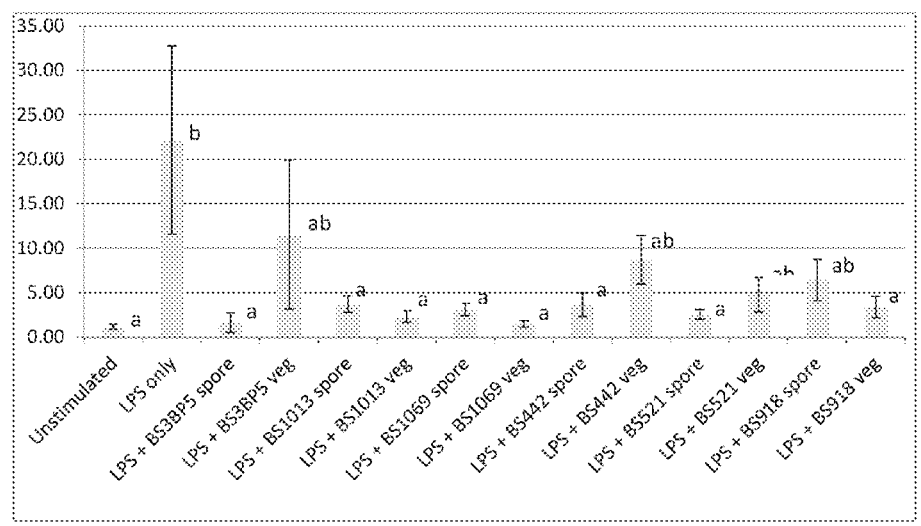
FIG. 25 is a bar graph depicting the anti-inflammatory effects of *Bacillus* strains in a mammalian cell line (rat intestinal epithelial cell line (IEC-6)). LPS was used to induce the inflammatory response. Tumor necrosis factor-α (TNF-α) gene expression was measured. Differing letters (a or b) indicate means differ statistically (P<0.10).

Lipopolysaccharide challenge in the IEC-6 rat intestinal epithelial cell line resulted in an increase (P<0.01) in gene expression of the inflammatory cytokine, TNF-α, compared to unstimulated IEC-6 cells (FIG. 25). *Bacillus* strains BS1013 and BS1069 decreased (P<0.10) the gene expression of TNF-α resulting from the administration of LPS alone when in either spore or vegetative states. *Bacillus* strains BS3BP5, BS442, and BS521 also decreased (P<0.10) the gene expression of TNF-α resulting from the administration of LPS alone, but only when in spore form. Conversely, *Bacillus* strain BS918 decreased (P<0.10) the gene expression of TNF-α resulting from the administration of LPS alone, but only in its vegetative form.

These data demonstrate the efficacy of *Bacillus* DFM strains for alleviating inflammation associated with a bacterial infection, and their effectiveness in a mammalian species. The *Bacillus* DFM strains can be used to alleviate macrophage inflammation. In addition, the *Bacillus* DFM strains can be used to alleviate gram negative bacterial infections, and the effects of these bacterial infections.

Example 15

Efficacy of a *Bacillus* DFM to Reduce Foam Formation in Commercial Deep Pit Swine Manure Storage Systems Deep swine manure pit systems are common in the US Midwest and have high potential for foaming. This is believed to be the result of the steadily increasing inclusion of fibrous by-products in swine feed and the resulting shifts in microbial ecology and fermentation characteristics in the stored manure. The efficacy of a three-strain *Bacillus* DFM was assessed to determine if its application in swine manure pits could positively alter the manure pit microbial fermentation profile and provide a tool for pit foam control. Five production sites each with three identical grow-finish barns (1400 head each) over individual deep pit systems were selected for evaluation. All sites were traditionally at high risk for foam production based on high inclusion levels of dried distillers grains containing solubles (DDGS) and other fibrous by-product ingredients in diets and from past historical incidences of foaming.

For each of the 3 pits per site, a baseline sampling was established prior to trial start using a 1∝ PVC pipe fitted with a ball valve to trap the sample. For each sampling, liquid depth and foam depth were measured and liquid:foam ratio calculated to accommodate varying pit volumes throughout the duration of the study since pit volumes varied tremendously after 21 day sampling. The tested product consisted of equal proportions of strains AGTP BS918 (NRRL B-50508), AGTP BS1013 (NRRL B-50509) and AGTP BS3BP5 (NRRL B-50510) as for examples 9 and 10. Other *Bacillus* strains can be used including but not limited to *Bacillus subtilis* AGTP BS442, *Bacillus subtilis* AGTP BS521, and *Bacillus subtilis* AGTP BS1069, and *Bacillus subtilis* AGTP 944, *Bacillus pumilus* AGTP BS1068 and *Bacillus pumilus* KX11-1.

Two *Bacillus* product inclusion rates were applied directly to the manure pit and tested against untreated control pits. The *Bacillus* pit inoculant was applied at a rate of $5.3 \times 10^4$ cfu/mL manure to be equivalent to the inoculation rate if fed to the animal at $1.5 \times 10^5$ cfu/g of feed and a 2.5-fold increased dose (2.5x) applied to the manure pit at a rate of $1.3 \times 10^6$ cfu/mL manure. The *Bacillus* product was re-applied every 60 days over the complete trial duration of 170 days. Data were analyzed using one-way ANOVA via Proc Mixed procedure of SAS (v. 9.1.3, SAS Institute, Inc., Cary, N.C.) with repeated measures for detection over time. Significance level α=0.10, averages were separated using Least Square Difference (LSD) test.

Figure 26:
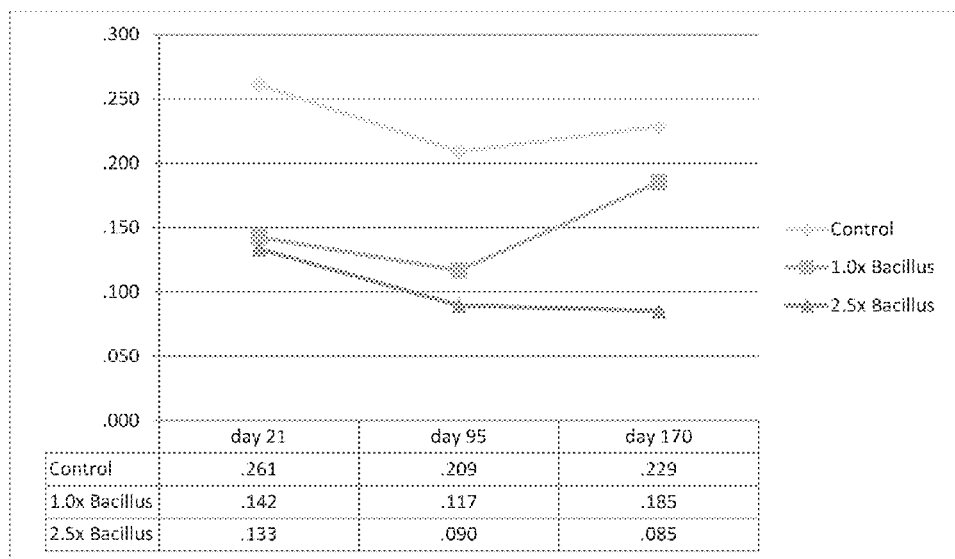
FIG. 26 is a line graph showing foam characteristics in a pit over 3 samplings within 170 day trial period.

There was no difference in foam depth, liquid depth, or foam:liquid ratio between the pits at the sites identified for the test (Table 33). However, three weeks after the treatment applications, foam depth was decreased (P=0.03) in pits treated with the *Bacillus* pit inoculant at either application rate compared to the untreated pits. Liquid depth did not differ between the three treatments three weeks after application of the *Bacillus* pit inoculant, resulting in a decrease (P=0.01) foam:liquid ratio when the *Bacillus* pit inoculant was applied at either application rate compared to untreated pits. Foam:liquid ratio was also reduced (P<0.10) with *Bacillus* inoculant at either application rate compared to control pits, when values were averaged over all three sampling points in the course of the 170 day trial (Table 34). Data indicate that the higher inclusion rate of the *Bacillus* inoculant resulted in more consistent reduction of foam over the course of the study (FIG. 26).

These data indicate that the use of a three-strain *Bacillus* inoculant applied directly to deep pit swine manure storage facilities controls accumulation of foam.

TABLE 33

Comparison of foam characteristics between baseline and 21 day sampling averaged over 5 sites only

| | before application | | | Day 21 after 1st application | | |
|---|---|---|---|---|---|---|
| Pit Treatment | foam depth (ft) | liquid depth (ft) | foam:liquid | foam depth (ft) | liquid depth (ft) | foam:liquid |
| Control | 0.41 | 1.94 | 0.21 | $1.16^b$ | 2.92 | $0.26^b$ |
| 1.0x *Bacillus* | 0.22 | 1.83 | 0.12 | $0.70^a$ | 2.87 | $0.14^a$ |
| 2.5x *Bacillus* | 0.17 | 2.08 | 0.09 | $0.60^a$ | 2.99 | $0.13^a$ |
| P-value | 0.378 | 0.856 | 0.311 | 0.031 | 0.945 | 0.011 |
| SEM[1] | 0.08 | 0.09 | 0.04 | 0.10 | 0.14 | 0.02 |

$^{a,b}$averages with differing superscripts were significantly different (P ≤ 0.10), means were separated using LS standard error of the mean.

TABLE 34

Comparison of foam characteristics averaged over 3 samplings within 170 day trial period.

| Pit Treatment | Average Foam: Liquid |
|---|---|
| Control | $0.23^b$ |
| 1.0x Bacillus | $0.15^a$ |
| 2.5x Bacillus | $0.10^a$ |
| P-value | 0.049 |
| $SEM^1$ | 0.03 |

$a, b$ averages with differing superscripts were significantly different (P ≤ 0.10), means were separated using LS standard error of the mean.

Example 16

Direct Application of Bacillus Product to Manure Pits on Commercial Grow-Finish Sites Alters Manure Characteristics To compare the efficacy of a three strain *Bacillus* pit product containing strains AGTP BS918 (NRRL B-50508), AGTP BS1013 (NRRL B-50509) and AGTP BS3BP5 (NRRL B-50510) in equal proportions to a current commercial swine manure waste treatment product (MicroSource S®; DSM), the three-strain *Bacillus* product was directly applied to the manure pits of three commercial production sites in the US Midwest that were currently feeding MicroSource S®. Other *Bacillus* strains can be used including but not limited to *Bacillus subtilis* AGTP BS442, *Bacillus subtilis* AGTP BS521, and *Bacillus subtilis* AGTP BS1069, and *Bacillus subtilis* AGTP 944, *Bacillus pumilus* AGTP BS1068 and *Bacillus pumilus* KX11-1.

The *Bacillus* product was tested at three production sites for one 60 day period to determine if it could improve manure management characteristics above the effect from MicroSource S® administration in the swine feed. Each site consisted of two identical rooms with individual manure pits and a capacity for 2250 market hogs. Per site, one barn was used as untreated control whereas the other barn received *Bacillus* pit treatment. For treated pits, *Bacillus* product inclusion rate was based on manure volume, with an application rate of $5.3 \times 10^4$ cfu/mL manure. Initial volume of the swine manure pits on test was estimated to be 120,000 gallons of manure, therefore a total of $2.4 \times 10^{13}$ cfu of *Bacillus* product was applied directly to the pit.

Control and treatment pits were sampled before and 60 days after *Bacillus* product application. Sampling over the entire pit depth was accomplished using a 1' PVC pipe fitted with a ball valve to trap the sample. Test indicator of improved manure characteristics was determined to be reduced % solids after 60 days of treatment. One-tailed Jonckheere-Terpstra non-parametric test with exact statistics and significance level α=0.10 was performed using SPSS statistical software (v. 17.0, IBM Corp., Armonk, N.Y.), to analyze difference between % solids before and after treatment application testing the mean differences.

There was no difference on average manure solids between any of the sites on test, in which MicroSource S® was included as standard operating procedure in all (Table 35). However, there was a 24.3% reduction (P=0.10) in solids over the 3 sites monitored when the three-strain *Bacillus* inoculant was added to the manure pit. These data indicate that application of the three-strain *Bacillus* inoculant improves manure management characteristics as indicated by reduction in percent solids beyond the MicroSource S® commercial product.

TABLE 35

Solid reduction after 60 days past *Bacillus* pit product application to treatment manure pits compared to control manure pit at the same production site.

| | | Solids (%) | | |
|---|---|---|---|---|
| Site - Barn | Treatment | before application | 60 days after application | % difference (before vs. after) |
| 1 - North | Control | 9.58 | 10.02 | +4.6 |
| 1 - South | Bacillus | 10.21 | 5.70 | −44.2 |
| 2 - North | Control | 7.03 | 7.68 | +9.3 |
| 2 - South | Bacillus | 8.31 | 8.35 | +0.5 |
| 3 - North | Control | 8.44 | 7.27 | −13.9 |
| 3 - South | Bacillus | 7.26 | 5.14 | −29.2 |
| Average | Control | | | $+/-0.0^a$ |
| | Bacillus | | | $-24.3^b$ |
| P-value ($SEM^1$) | | | | 0.100 (8.60) |

$^1$SEM, Standard error of the mean.

Example 17

Comparison of the Effect of a Three-Strain Bacillus Direct Fed Microbial and Microsource S® on Growth Performance of Growing Pigs A study was conducted to compare the efficacy of a novel three-strain *Bacillus* DFM and MicroSource S® (DSM) for improving growth performance of growing pigs. A total of 144 pigs (initial body weight: approximately 23 kg) were placed on test and penned in 36 pens with four pigs/pen in an environmentally controlled grower pig facility. One of three dietary treatments was assigned to each pen (12 replicates/treatment) and fed for the 6-week duration of the study. Treatments consisted of a control basal diet, a three-strain *Bacillus* direct-fed microbial (DFM), and MicroSource S® (DSM), which is a *Bacillus*-based commercial swine waste treatment DFM.

The basal diet was formulated to contain 50% by-product (35% DDGS and 15% wheat middlings; Table 36). Phytase (500 FTU/kg) was added to all diets. The novel *Bacillus* DFM consisted of equal proportions of *Bacillus subtilis* strains AGTP BS918 (NRRL B-50508), AGTP BS1013 (NRRL B-50509) and AGTP BS3BP5 (NRRL B-50510) summing to a guaranteed $3.0 \times 10^8$ cfu/g of DFM product, included at a rate of 0.25 lb/ton of feed resulting in a concentration of $3.75 \times 10^4$ cfu/g in the diet. Other *Bacillus* strains can be used including but not limited to *Bacillus subtilis* AGTP BS442, *Bacillus subtilis* AGTP BS521, and *Bacillus subtilis* AGTP BS1069, and *Bacillus subtilis* AGTP 944, *Bacillus pumilus* AGTP BS1068 and *Bacillus pumilus* KX11-1.

TABLE 36

Basal diets Compositions

| Ingredients, % | |
|---|---|
| Corn, % | 26.510 |
| DDGS, % | 35.00 |
| Wheat middlings | 15.00 |
| SBM, 48% | 19.00 |
| HP DDG | 0.00 |
| Soy bean oil | 1.00 |
| Corn starch | 1.00 |
| Limestone | 1.25 |
| DCP | 0.00 |
| Lysine HCL | 0.45 |
| DL-Met | 0.04 |

TABLE 36-continued

Basal diets Compositions

| | |
|---|---|
| L-Threonine | 0.03 |
| L-Tryptophan | 0.00 |
| Salt | 0.40 |
| Vit min-mix | 0.30 |
| Phytase | 0.02 |
| Total | 100.00 |
| Calculated composition, % | |
| ME, kcal/kg | 3315 |
| CP | 23.20 |
| Dig Lys | 1.17 |
| Dig Met | 0.39 |
| Dig M + C | 0.74 |
| Dig Thr | 0.73 |
| Dig Tryp | 0.20 |
| Ca | 0.63 |
| Total P | 0.61 |
| Dig P | 0.35 |

MicroSource S® was included in the diet at 1 lb/ton of feed, resulting in $7.5 \times 10^4$ cfu/g in the diet. Pig body weight gain and pen feed intake were determined on d 21 and d 42 of the trial, and average daily gain (ADG), average daily feed intake (ADFI), and gain:feed (G:F) were calculated.

Pigs fed diets supplemented with the novel *Bacillus* DFM had greater ADG from d 0 to 21 of the trial than pigs fed the control diets or diets supplemented with the commercial DFM, Microsource S® (Table 37). This increase in daily gain tended to result in greater (P<0.10) body weight in pigs fed the novel *Bacillus* DFM on d 21 of the study compared to the other two treatments. These data indicate that the novel *Bacillus* DFM improves body weight gain in growing pigs compared to an existing commercial *Bacillus*-based DFM (MicroSource S®).

TABLE 37

Growth performance of pigs fed a novel *Bacillus* DFM compared to MicroSource S ®.

| | Diet | | | | |
|---|---|---|---|---|---|
| Item | Control | Bacillus DFM | Microsource S ® | SEM | P-value |
| d 0-21 | | | | | |
| Initial BW, kg | 23.89 | 23.87 | 23.77 | 1.04 | 0.6317 |
| ADG, kg | 0.77[b] | 0.82[a] | 0.77[b] | 0.02 | 0.0435 |
| ADFI, kg | 1.47 | 1.53 | 1.43 | 0.05 | 0.0640 |
| G: F, kg/kg | 0.53 | 0.54 | 0.54 | 0.02 | 0.1602 |
| Final BW, kg | 40.09[d] | 41.09[c] | 39.94[d] | 1.19 | 0.0673 |
| d 21-42 | | | | | |
| ADG, kg | 0.96 | 0.94 | 0.88 | 0.04 | 0.4593 |
| ADFI, kg | 1.45 | 1.38 | 1.23 | 0.12 | 0.5022 |
| G: F, kg/kg | 0.66 | 0.69 | 0.75 | 0.05 | 0.6712 |
| Final BW, kg | 60.17 | 60.75 | 58.32 | 1.64 | 0.2348 |

[a,b]Means without common superscripts are different, P < 0.05.
[c,d]Means without common superscripts are different, P < 0.10.

Example 18

Identification of Enzymatic Activities of Novel *Bacillus* Strains

In vitro assays were conducted to test for enzyme activity of novel *Bacillus* strains against fibrous feed substrates commonly found in feed ingredients used to formulate swine and poultry diets. High-throughput screening of these test strains was performed by replicate spot plating of 2 microliters liquid culture onto 15.0 ml of various substrate media types of interest in 100×100×15 mm grid plates. Cellulase, xylanase, and β-mannanase activities were determined based on specific substrate utilization by the individual strains.

Media components used to assay the substrate utilization properties from enzymatic activity of the environmentally derived strains are described in Table 38. Assay plates were left to dry for 30 minutes following culture application, and then incubated at 32° C. for 24 hours. Enzymatic activities for each strain were determined by measuring the zone of substrate degradation in millimeters, as indicated by clearing of the surrounding edge of colony growth. Mean values from replicate plates were recorded.

TABLE 38

Media components used to assay the enzymatic activities illustrated by substrate utilization properties of environmentally derived *Bacillus*.

| Plate Assay | Media Composition | Extra Visualization Requirements |
|---|---|---|
| Cellulase | 0.1% Ammonium Sulfate, 0.1% Potassium Phosphate Dibasic, 0.1% Yeast Extract, 1.0% Polypeptone, 1.5% Agar, 0.75% Carboxymethyl Cellulose (CMC) | 30 minute 0.05% Congo Red Dye stain, follwed by 1M NaCl rinse. |
| Xylanase | Nutrient Agar, 2% Xylan | None; Measure Zone of Clearing in opaque media |
| β-Mannanase | Nutrient Agar, 0.6% Locust Bean Gum | 0.05% Iodine Stain Solution |

The fibrolytic degrading enzyme activities of several *Bacillus subtilis* and *Bacillus pumilus* strains are reported in Table 39. All strains exhibit degrading activity against at least two of the three fibrous substrates evaluated. These data indicate that these novel *Bacillus* strains have enzyme degrading capacity against cellulose, xylan, and β-mannose.

TABLE 39

Cellulase, xylanase, and β-mannanase activities of *Bacillus* strains.

| Isolate Name | CMCase (Cellulase) | Xylanase | β-Mannanase |
|---|---|---|---|
| BS3BP5 | 3.3 | 3.0 | N/A |
| BS442 | 1.8 | 2.5 | 2.0 |
| BS521 | 6.0 | 4.0 | 2.0 |
| BS918 | 4.0 | 5.5 | 3.3 |
| BS1013 | 6.5 | 4.0 | 2.5 |
| BP1068 | 3.0 | 6.0 | 4.5 |
| BS1069 | 4.0 | 4.0 | 2.5 |
| BS944 | 6.5 | 3.5 | 1.0 |
| KXII-1 | 2.5 | 5.0 | N/A |

Example 19

The Effect of Supplementation of a *Bacillus* Direct-Fed Microbial (DFM) in Feed on Residual Bacterial Load after Washing in Commercial Grow-Finish Facility To determine the growth performance of pigs fed commercial corn-soy based diets with increasing amounts of by-product, a grow-to-finish study was conducted. A total of 1040 pigs were weaned at approximately 3 weeks of age and weaned using standard commercial starter diet. Animals were separated by gender, distributed over 40 pens on trial and phase fed. From day 42 on, a direct-fed microbial consisting of equal proportions of *Bacillus subtilis* strains AGTP BS918 (NRRL B-50508), AGTP BS1013 (NRRL B-50509) and AGTP BS3BP5 (NRRL B-50510) summing to a guaranteed $3.0 \times 10^8$ cfu/g of DFM product, was included at a rate of 1 lb/ton in feed, resulting in a concentration of $1.5 \times 10^5$ cfu/g in the diet (Table 40). Other *Bacillus* strains can be used including but not limited to *Bacillus subtilis* AGTP BS442, *Bacillus subtilis* AGTP BS521, and *Bacillus subtilis* AGTP BS1069, and *Bacillus subtilis* AGTP 944, *Bacillus pumilus* AGTP BS1068 and *Bacillus pumilus* KX11-1.

TABLE 40

Feeding phases and diet composition.[1]

| Ingredient (%) | Phase | | | | | |
|---|---|---|---|---|---|---|
| | 3) Early Grower | 4) Late Grower | 5) Early Finish | 6) Mid Finish | 7) Late Finish | 8) Withdrawal |
| Duration (Days) | 42-63 | 63-84 | 84-105 | 105-126 | 126-151 | 151+ |
| Corn | 28.2 | 31.9 | 35.4 | 37.4 | 41.0 | 71.5 |
| SBM (46.5% CP) | 18.2 | 14.5 | 11.3 | 9.4 | 5.8 | 6.0 |
| Spray dried whey | 0.0 | 0.0 | 0.0 | 0.0 | 0.0 | 0.0 |
| Sel. menh. fishmeal | 0.0 | 0.0 | 0.0 | 0.0 | 0.0 | 0.0 |
| cDDGS | 35.0 | 35.0 | 35.0 | 35.0 | 35.0 | 20.0 |
| Wheat Midds | 15.0 | 15.0 | 15.0 | 15.0 | 15.0 | 0.0 |
| Fat | 1.000 | 1.000 | 1.000 | 1.000 | 1.000 | 0.050 |
| MCP (21% P) | 0.000 | 0.000 | 0.000 | 0.000 | 0.000 | 0.550 |
| Limestone (CaCO$_2$) | 1.475 | 1.470 | 1.450 | 1.415 | 1.400 | 1.150 |
| Salt | 0.350 | 0.350 | 0.350 | 0.350 | 0.350 | 0.300 |
| Vitamin premix | 0.090 | 0.090 | 0.075 | 0.150 | 0.150 | 0.150 |
| Mineral premix | 0.125 | 0.125 | 0.085 | 0.150 | 0.150 | 0.150 |
| Lysine HCl | 0.470 | 0.400 | 0.350 | 0.200 | 0.200 | 0.150 |
| DL-Methionine | 0.000 | 0.000 | 0.000 | 0.000 | 0.000 | 0.000 |
| L-Threonine | 0.055 | 0.020 | 0.000 | 0.000 | 0.000 | 0.000 |
| Phyzyme 2500TPT | 0.020 | 0.020 | 0.020 | 0.020 | 0.020 | 0.020 |

[1]SBM, soybean meal; CP, crude protein; cDDGS, corn dried distiller's grains with solubles with ~10% oil content; treatment included to the expense of corn.

Figure 27:
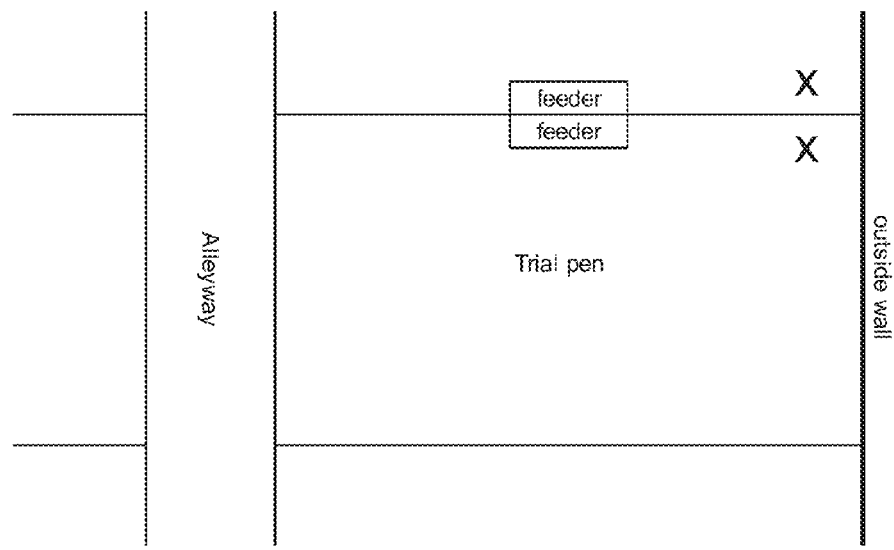
FIG. 27 is a representative schematic of a BioLuminescence measure in each pen in the area marked with an "x."

After animal load-out, washing and 24 hour air drying of the facility, residual bacterial load was determined as indicator for pen cleanliness. Samples were collected in the laying area in the back of each pen in the corner closest to the feeder, approximately 1 foot from side and end panel (FIG. 27).

A 16 in$^2$ area of the facility flooring was swabbed using a pre-moistened sterile swab (PocketSwab Plus, Charm Sciences, Lawrence, Mass.). The sample area was passed 10 times for each swab and analyzed in triplicate. Within 15 seconds following the swabbing procedure, the swab was placed in LUMT Bioluminescence reader (Charm Sciences, Lawrence, Mass.). The resulting relative light unit (RLU) values were recorded and averaged by pen before statistical analysis.

Data was analyzed using NPAR1WAY procedure of SAS (v. 9.1.3, SAS Institute, Inc., Cary, N.C.) with significance level $\alpha=0.05$. Data indicated significantly reduced (P<0.05) bacterial load in pens fed diets containing DFM compared with control diets after pen load-out, washing and drying (Table 41).

TABLE 41

Comparison of relative light unit (RLU) indicating residual bacterial load in commercial pens fed control diets or diets with direct-fed microbial (DFM) inclusion after washing and air-drying of barn.

| Treatment | RLU |
|---|---|
| Control | 558,324[b] |
| DFM | 421,388[a] |
| P-value | 0.025 |
| SEM[1] | 39,231 |

[a, b]averages with differing superscripts were significantly different (P ≤ 0.05);
[1]SEM, standard error of the mean.

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations that operate according to the principles of the invention as described. Therefore, it is intended that this invention be limited only by the claims and the equivalents thereof. The disclosures of patents, references and publications cited in the application are incorporated by reference in their entirety herein.

BIBLIOGRAPHY

Association of Analytical Chemists (AOAC) (2007). Official methods of analysis, 18th ed. AOAC, Washington, D.C.

Liu K. 2011. Chemical composition of distillers grains, a review. J. Agric. Food CheM 59:1508-1526.

Metzler-Zebeli, B. U., Hooda, S., Pieper, R., Zijlstra, R. T., Van Kessel, A. G., Mosenthin, R. and G. Gänzle (2010). Polysaccharides Modulate Bacterial Microbiota, Pathways for Butyrate Production, and Abundance of Pathogenic *Escherichia coli* in the Pig Gastrointestinal Tract; *J Appl Env Microbiol* 76(11), 3692-3701.

NRC. 1998. Nutrient Requirements of Swine. 10th rev. ed. Natl. Acad. Press, Washington, D.C.

Stein, H. H. and G. C. Shurson. 2009. The use and application of distillers dried grains with solubles in swine diets. J. Anim. Sci. 87:1292-1303.

Stein, H. H., B. Seve, M. F. Fuller, P. J. Moughan, and C. F. M. de Lange. 2007. Invited review: Amino acid bioavailability and digestibility in pig feed ingredients: Terminology and application. J. Anim. Sci. 85:172-180.

Spence, C., Whitehead, T. R. and M. A. Cotta (2008). Development and comparison of SYBR Green quantitative real-time PCR assays for detection and enumeration of sulfate reducing bacteria in stored swine manure. *J Appl Microbiol* 105, 2143-2152.

Yegani M., and D. R. Korver. 2008. Factors affecting intestinal health in poultry. Poult. Sci 87:2052-2063.

Yu, Y., Lee, C., Kim, J. and S. Hwang (2005). Group-Specific Primer and Probe Sets to Detect Methanogenic Communities Using Quantitative Real-Time Polymerase Chain Reaction. *Biotechnol Bioeng* 89, 670-679.

What is claimed is:

1. A biologically pure *Bacillus* strain in the form of a pellet having enzymatic activity selected from the group consisting of: *Bacillus subtilis* AGTP BS3BP5 (NRRL B-50510), *Bacillus subtilis* AGTP BS442 (NRRL B-50542), *Bacillus subtilis* AGTP BS521 (NRRL B-50545), *Bacillus subtilis* AGTP BS918 (NRRL B-50508), *Bacillus subtilis* AGTP BS1013 (NRRL B-50509), *Bacillus subtilis* AGTP BS1069 (NRRL B-50544), *Bacillus subtilis* AGTP 944 (NRRL B-50548), *Bacillus pumilus* AGTP BS1068 (NRRL B-50543), and *Bacillus pumilus* KX11-1 (NRRL B-50546).

2. The strain of claim 1, wherein the enzymatic activity is selected from the group consisting of cellulase activity, α-amylase activity, xylanase activity, esterase, β-mannanase, lipase activity, protease activity, and combinations thereof.

3. The strain of claim 1, wherein the enzymatic activity is selected from the group consisting of zeinase activity and soy protease activity, and combinations thereof.

4. The strain of claim 1, wherein, when the strain is administered to an animal, the strain provides an improvement in at least one of the following: body weight, average daily gain, average daily feed intake, feed efficiency, carcass characteristics, nutrient digestibility and manure waste problems.

5. The strain of claim 1, wherein, when the strain is administered to an animal, the strain provides an improvement in at least one of the following: body weight, average daily gain, average daily feed intake, feed efficiency, carcass characteristics, nutrient digestibility and manure waste problems by at least 2% compared to a control.

6. The strain of claim 4, wherein the animal is poultry or pig.

7. The strain of claim 1, wherein the *Bacillus* strain is *Bacillus subtilis* AGTP BS3BP5 (NRRL B-50510).

8. The strain of claim 1, wherein the *Bacillus* strain is *Bacillus subtilis* AGTP BS442 (NRRL B-50542).

9. The strain of claim 1, wherein the *Bacillus* strain is *Bacillus subtilis* AGTP BS521 (NRRL B-50545).

10. The strain of claim 1, wherein the *Bacillus* strain is *Bacillus subtilis* AGTP BS918 (NRRL B-50508).

11. The strain of claim 1, wherein the *Bacillus* strain is *Bacillus subtilis* AGTP BS1013 (NRRL B-50509).

12. The strain of claim 1, wherein the *Bacillus* strain is *Bacillus pumilus* AGTP BS1068 (NRRL B-50543).

13. The strain of claim 1, wherein the *Bacillus* strain is *Bacillus subtilis* AGTP BS1069 (NRRL B-50544).

14. The strain of claim 1, wherein the *Bacillus* strain is *Bacillus subtilis* B AGTP 944 (NRRL B-50548).

15. The strain of claim 1, wherein the *Bacillus* strain is *Bacillus pumilus* KX11-1 (NRRL B-50546).

16. A biologically pure freeze-dried *Bacillus* strain selected from the group consisting of: *Bacillus subtilis* AGTP BS3BP5 (NRRL B-50510), *Bacillus subtilis* AGTP BS442 (NRRL B-50542), *Bacillus subtilis* AGTP 1BS521 (NRRL B-50545), *Bacillus subtilis* AGTP BS918 (NRRL B-50508), *Bacillus subtilis* AGTP BS1013 (NRRL B-50509), *Bacillus subtilis* AGTP BS1069 (NRRL B-50544), *Bacillus subtilis* AGTP 944 (NRRL B-50548), *Bacillus pumilus* AGTP BS1068 (NRRL B-50543), and *Bacillus pumilus* KX11-1 (NRRL B-50546).

17. A composition comprising a growth medium and an enzyme producing bacterial strain in the form of a pellet, wherein the bacterial strain is selected from the group consisting of: *Bacillus subtilis* AGTP BS3BP5 (NRRL B-50510), *Bacillus subtilis* AGTP BS442 (NRRL B-50542), *Bacillus subtilis* AGTP BS521 (NRRL B-50545), *Bacillus subtilis* AGTP BS918 (NRRL B-50508), *Bacillus subtilis* AGTP BS1013 (NRRL B-50509), *Bacillus subtilis* AGTP BS1069 (NRRL B-50544), *Bacillus subtilis* AGTP 944 (NRRL B-50548), *Bacillus pumilus* AGTP BS1068 (NRRL B-50543), and *Bacillus pumilus* KX11-1 (NRRL B-50546).

* * * * *